(12) United States Patent
Goble et al.

(10) Patent No.: US 10,426,565 B2
(45) Date of Patent: Oct. 1, 2019

(54) KNEE INSTRUMENTS AND METHODS

(71) Applicant: E. Marlowe Goble, Logan, UT (US)

(72) Inventors: E. Marlowe Goble, Logan, UT (US);
Carlyle J. Creger, Wellsville, UT (US);
Daniel J. Triplett, Providence, UT (US)

(73) Assignee: E. Marlowe Goble, Logan, UT (US)

( * ) Notice: Subject to any disclaimer, the term of this patent is extended or adjusted under 35 U.S.C. 154(b) by 0 days.

(21) Appl. No.: 15/081,828

(22) Filed: Mar. 25, 2016

(65) Prior Publication Data

US 2016/0278938 A1    Sep. 29, 2016

Related U.S. Application Data

(60) Provisional application No. 62/138,307, filed on Mar. 25, 2015, provisional application No. 62/302,787, filed on Mar. 2, 2016.

(51) Int. Cl.
*A61B 17/17* (2006.01)
*A61B 90/00* (2016.01)
(Continued)

(52) U.S. Cl.
CPC ............ *A61B 90/06* (2016.02); *A61B 17/155* (2013.01); *A61B 17/1675* (2013.01); *A61B 17/1764* (2013.01); *A61B 2090/067* (2016.02)

(58) Field of Classification Search
CPC .................................................. A61B 17/155
See application file for complete search history.

(56) References Cited

U.S. PATENT DOCUMENTS

| 3,949,428 A | 4/1976 | Cavendish |
| 4,187,559 A | 2/1980 | Grell |

(Continued)

FOREIGN PATENT DOCUMENTS

| EP | 2145590 | 5/2012 |
| EP | 2626044 | 12/2016 |

(Continued)

OTHER PUBLICATIONS

Insall, John N. Surgery of the Knee. New York: Churchill Livingstone, 1984. pp. 631-365.
(Continued)

*Primary Examiner* — Samuel S Hanna
(74) *Attorney, Agent, or Firm* — Maywood IP Law; G. Jo Hays; David W. Meibos

(57) ABSTRACT

Knee arthroplasty instrument systems directly reference and align with the anterior distal with the anterior distal femoral cortex, the mechanical axis of the leg, and Whiteside's line. The anterior femoral resection is aligned in the same plane as the anterior distal femoral cortex. The center of the femoral head, the medial/lateral center of the distal femur, the medial/lateral center of the proximal tibia, and the second toe, medial/lateral center of the ankle, or anterior tibial spine are all aligned to the mechanical axis of the leg while the leg is in full extension and the knee joint is distracted. Whiteside's line is referenced while the distal femur is intact, before any distal femoral resection, and the anterior and posterior femoral resections and chamfer cuts are aligned to this reference using a jig. Methods of using the instrument systems are disclosed.

13 Claims, 78 Drawing Sheets

(51) Int. Cl.
*A61B 17/16* (2006.01)
*A61B 17/15* (2006.01)

(56) References Cited

U.S. PATENT DOCUMENTS

| | | | |
|---|---|---|---|
| 4,242,758 A | 1/1981 | Amis | |
| 4,364,389 A | 12/1982 | Keller | |
| 4,426,071 A | 1/1984 | Klevstad | |
| 4,457,307 A | 7/1984 | Stillwell | |
| 4,502,474 A | 3/1985 | Comparetto | |
| 4,509,511 A | 4/1985 | Neufeld | |
| 4,524,766 A | 6/1985 | Petersen | |
| 4,565,192 A | 1/1986 | Shapiro | |
| 4,566,448 A | 1/1986 | Rohr, Jr. | |
| 4,567,885 A | 2/1986 | Androphy | |
| 4,567,886 A | 2/1986 | Petersen | |
| 4,624,250 A | 11/1986 | Saunders | |
| 4,627,425 A | 12/1986 | Reese | |
| 4,677,973 A | 7/1987 | Slocum | |
| 4,703,751 A | 11/1987 | Pohl | |
| 4,718,414 A | 1/1988 | Saunders | |
| 4,722,330 A | 2/1988 | Russell | |
| 4,736,737 A | 4/1988 | Fargie | |
| 4,759,350 A | 7/1988 | Dunn | |
| 4,773,407 A | 9/1988 | Petersen | |
| 4,892,093 A | 1/1990 | Zarnowski | |
| 4,893,619 A | 1/1990 | Dale | |
| 4,907,578 A | 3/1990 | Petersen | |
| 4,926,847 A | 5/1990 | Luckman | |
| 4,938,762 A | 7/1990 | Wehrli | |
| 4,944,756 A | 7/1990 | Kenna | |
| 4,944,760 A | 7/1990 | Kenna | |
| 4,952,213 A | 8/1990 | Bowman | |
| 5,002,545 A | 3/1991 | Whiteside | |
| 5,007,912 A | 4/1991 | Albrektsson | |
| 5,021,055 A | 6/1991 | Burkinshaw | |
| 5,037,423 A | 8/1991 | Kenna | |
| 5,049,149 A * | 9/1991 | Schmidt | A61B 17/15 606/87 |
| 5,053,037 A | 10/1991 | Lackey | |
| 5,053,039 A | 10/1991 | Hofmann | |
| 5,062,852 A | 11/1991 | Dorr | |
| 5,395,377 A | 3/1995 | Petersen | |
| 5,472,415 A | 12/1995 | King | |
| 5,514,143 A | 5/1996 | Bonutti | |
| 5,601,563 A | 2/1997 | Burke | |
| 5,624,444 A * | 4/1997 | Wixon | A61B 17/155 606/88 |
| 5,688,281 A * | 11/1997 | Cripe | A61B 17/155 606/88 |
| 5,709,689 A | 1/1998 | Ferrante | |
| 5,749,876 A | 5/1998 | Duvillier | |
| 5,925,049 A * | 7/1999 | Gustilo | A61B 17/155 606/82 |
| 6,013,081 A * | 1/2000 | Burkinshaw | A61B 17/155 606/102 |
| 6,022,332 A | 2/2000 | Nelson | |
| 6,234,173 B1 | 5/2001 | Hajianpour | |
| 6,258,096 B1 * | 7/2001 | Seki | A61B 17/155 606/102 |
| 6,852,115 B2 | 2/2005 | Kinnett | |
| 7,104,997 B2 | 9/2006 | Lionberger | |
| 7,547,307 B2 | 6/2009 | Carson | |
| 7,621,920 B2 | 11/2009 | Claypool | |
| 7,641,660 B2 | 1/2010 | Lakin | |
| 7,658,741 B2 | 2/2010 | Claypool | |
| 7,665,167 B2 | 2/2010 | Branch | |
| 7,780,672 B2 | 8/2010 | Metzger | |
| 7,947,862 B2 | 5/2011 | Livorsi | |
| 8,052,692 B2 | 11/2011 | Lionberger | |
| 8,070,752 B2 | 12/2011 | Metzger | |
| 8,382,766 B2 | 2/2013 | Warkentine | |
| 8,518,051 B2 | 8/2013 | Shoham | |
| 9,005,207 B2 | 4/2015 | Dodds | |
| 9,572,586 B2 | 2/2017 | van der Walt | |
| 2002/0173797 A1 | 11/2002 | Van Zile | |
| 2005/0149037 A1 | 7/2005 | Steffensmeier | |
| 2007/0197944 A1 | 8/2007 | Bruce | |
| 2009/0088768 A1 | 4/2009 | Grant | |
| 2010/0016858 A1 | 1/2010 | Michel | |
| 2011/0245835 A1 | 10/2011 | Dodds | |
| 2012/0136359 A1 | 5/2012 | Grunder | |
| 2012/0316564 A1 | 12/2012 | Serbousek | |
| 2014/0114319 A1 | 4/2014 | Wilkinson | |
| 2014/0243991 A1 | 8/2014 | Collazo | |
| 2015/0157337 A1 | 6/2015 | Wolf | |
| 2015/0305754 A1 | 10/2015 | Metzger | |
| 2016/0051268 A1 | 2/2016 | Seitlinger | |
| 2016/0287238 A1 | 10/2016 | DeMayo | |
| 2016/0361178 A1 | 12/2016 | Budhabhatti | |
| 2017/0100132 A1 | 4/2017 | Collazo | |
| 2017/0290597 A1 | 10/2017 | Goble | |
| 2018/0280038 A1 | 10/2018 | Goble | |
| 2018/0296232 A1 | 10/2018 | Nielsen | |

FOREIGN PATENT DOCUMENTS

| | | |
|---|---|---|
| EP | 3273877 | 1/2018 |
| WO | WO2016154606 | 9/2016 |
| WO | WO2017223353 | 12/2017 |

OTHER PUBLICATIONS

DePuy Synthes. P.F.C. Sigma Knee Systems. Surgical Technique. 2013. pp. 19-23.

Tiftikçi U, Serbest S, Burulday V. Can Achilles tendon be used as a new distal landmark for coronal tibial component alignment in total knee replacement surgery? An observational MRI study. Therapeutics and Clinical Risk Management. 2017:13. pp. 81-86.

* cited by examiner

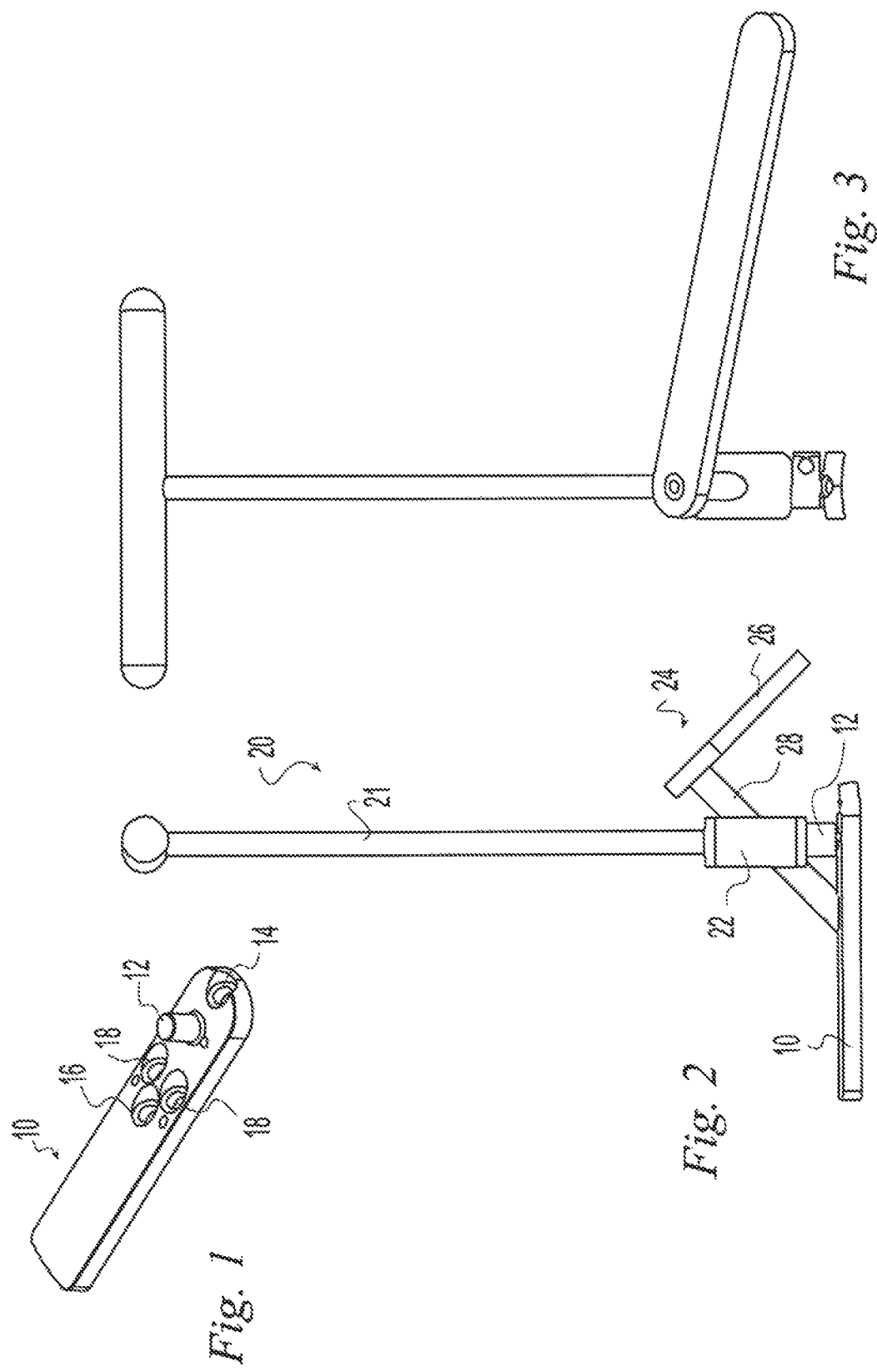

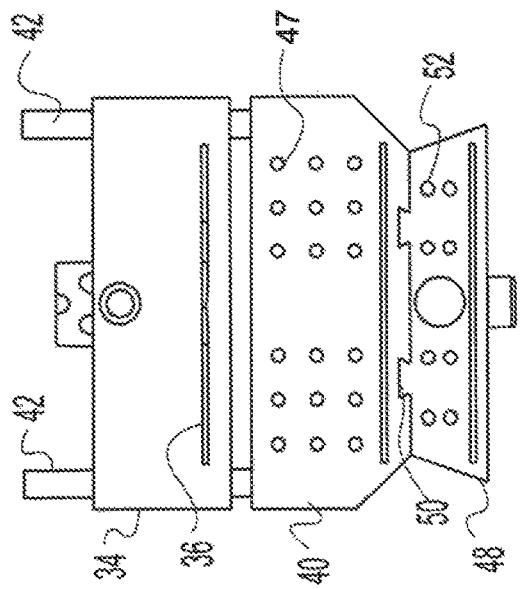
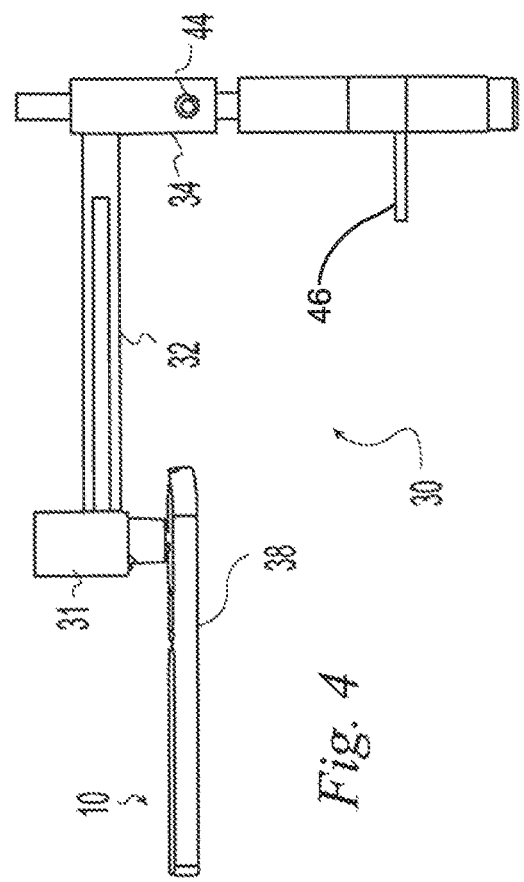
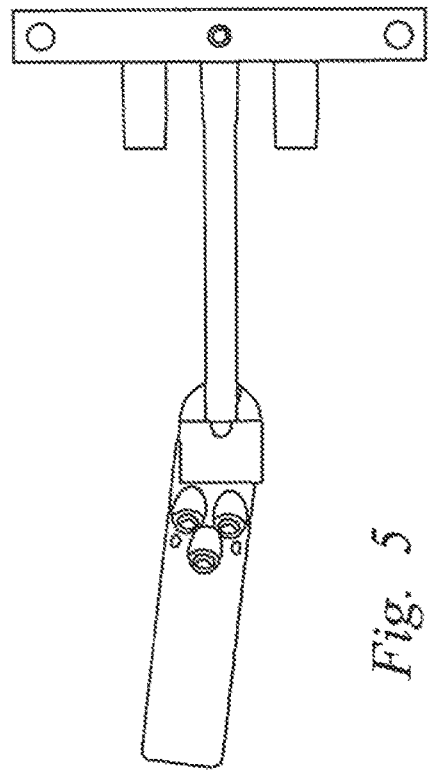
Fig. 6
Fig. 4
Fig. 5

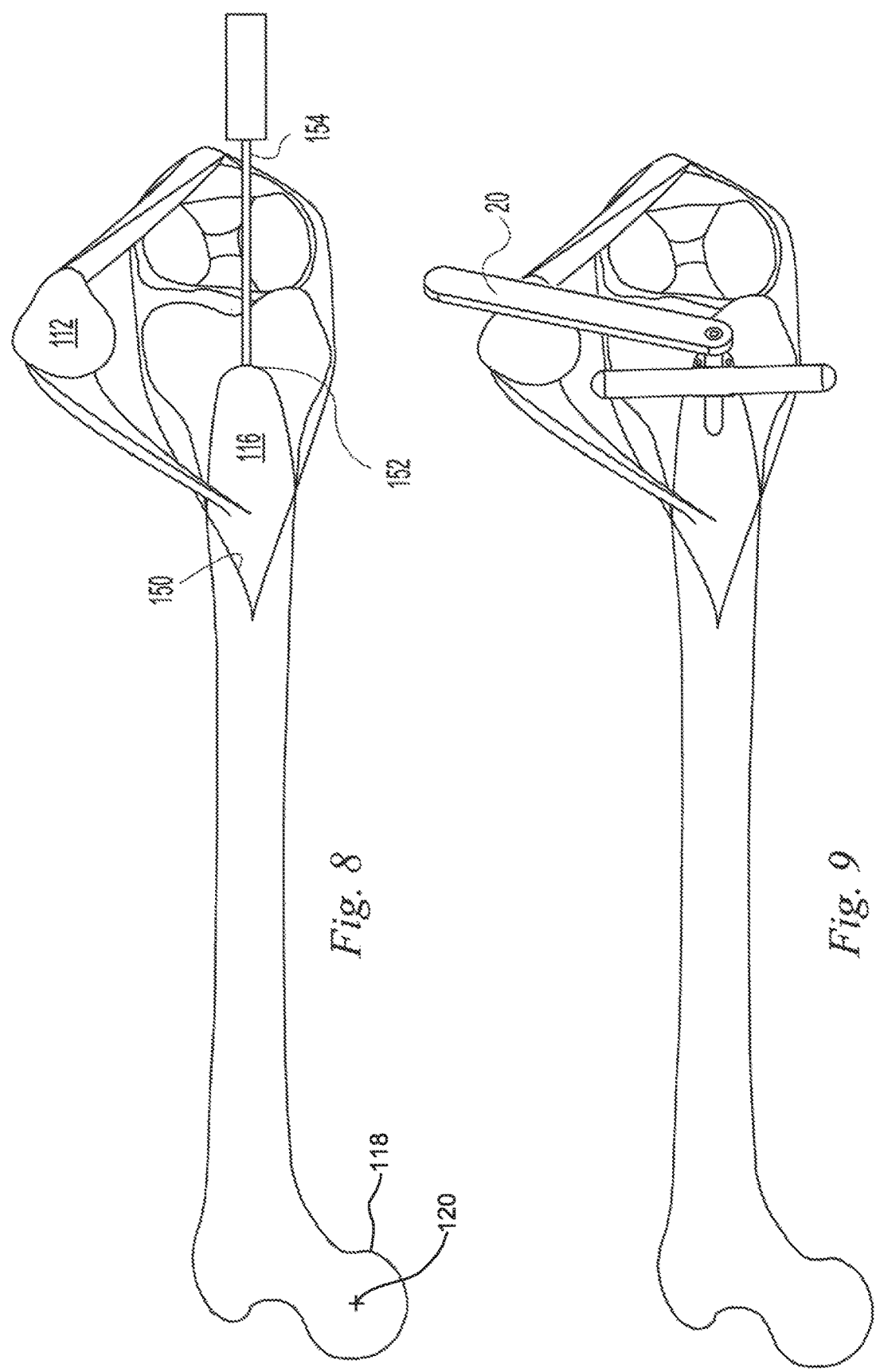

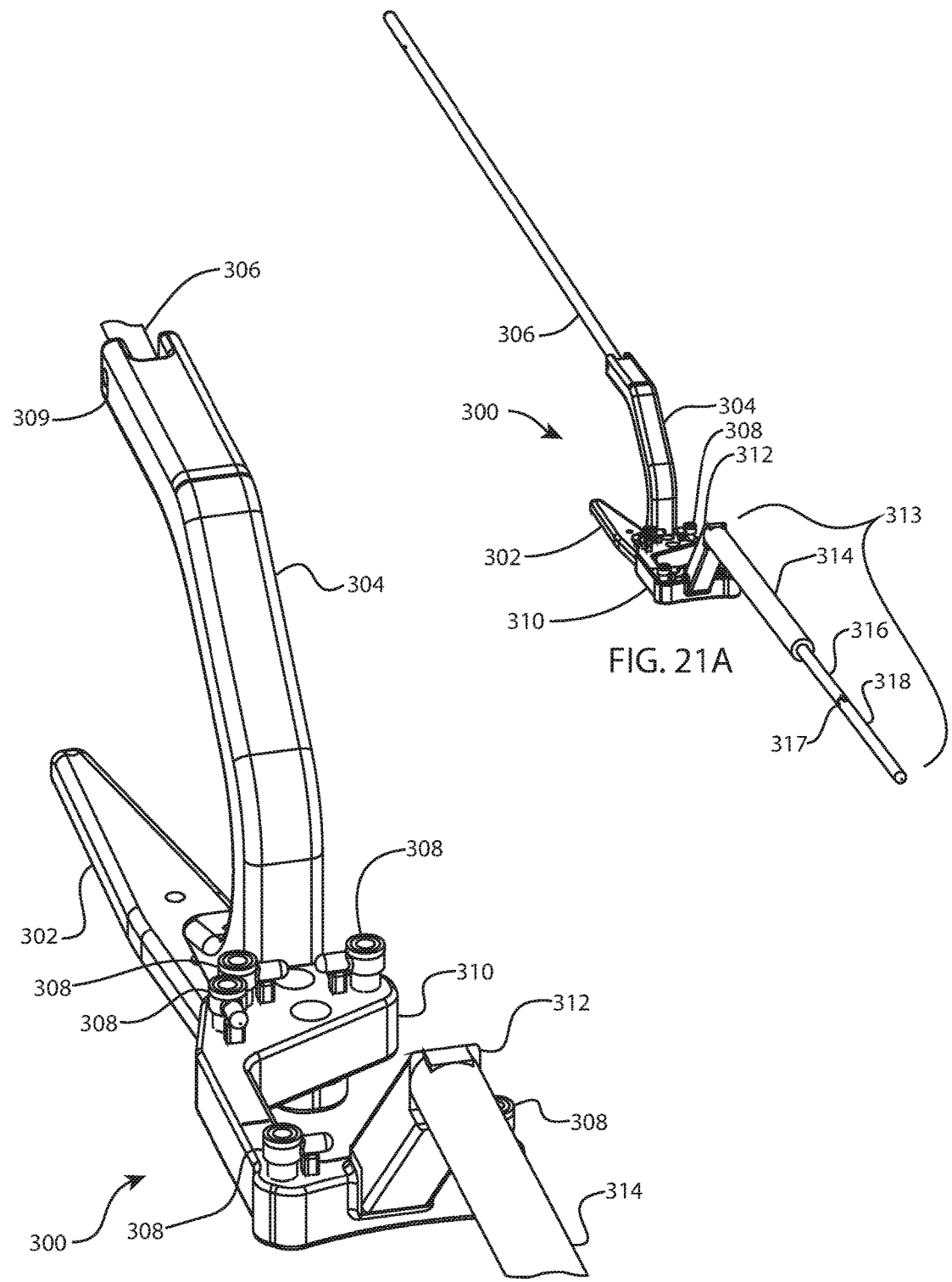

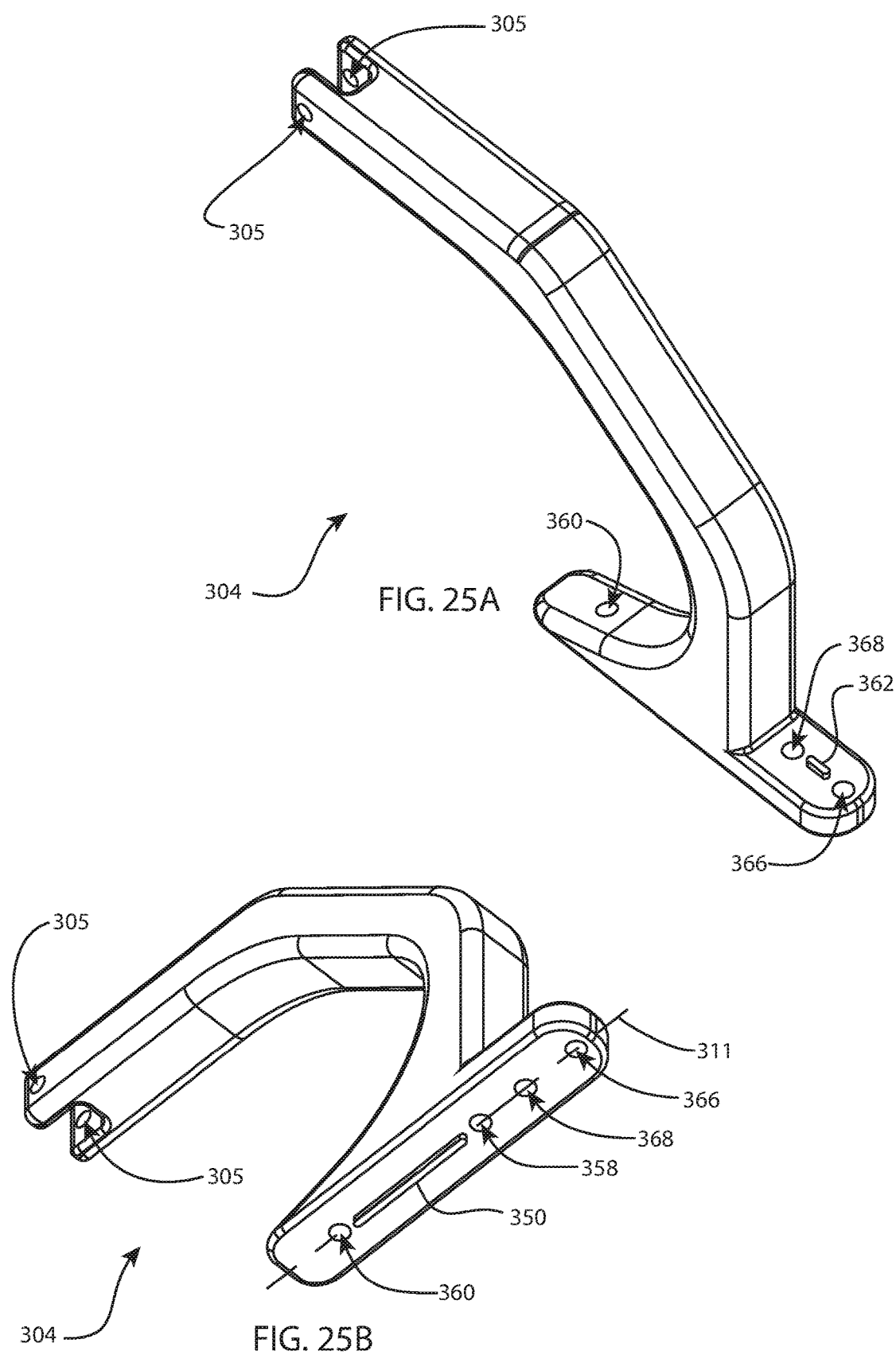

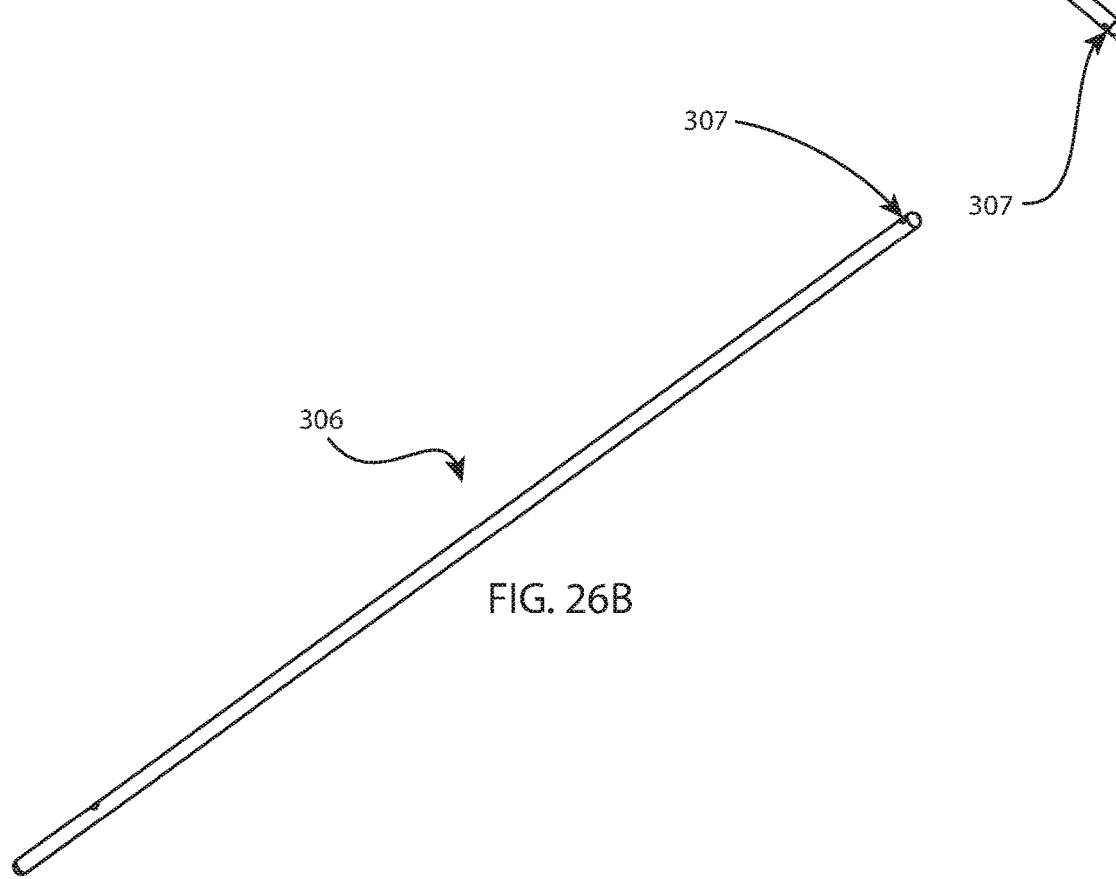

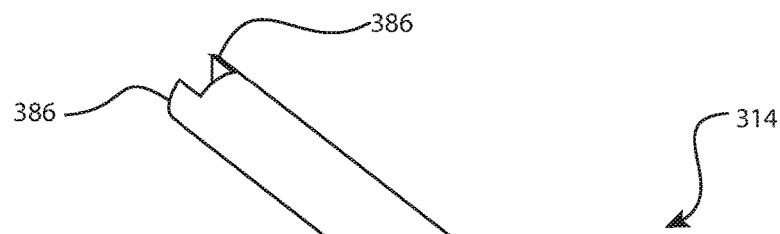
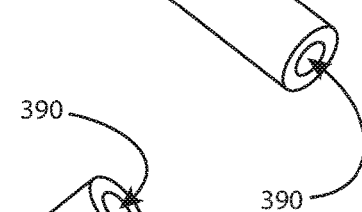
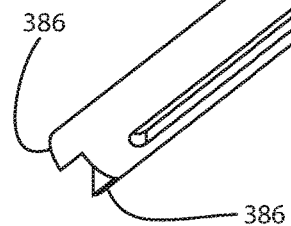
FIG. 30A
FIG. 30B

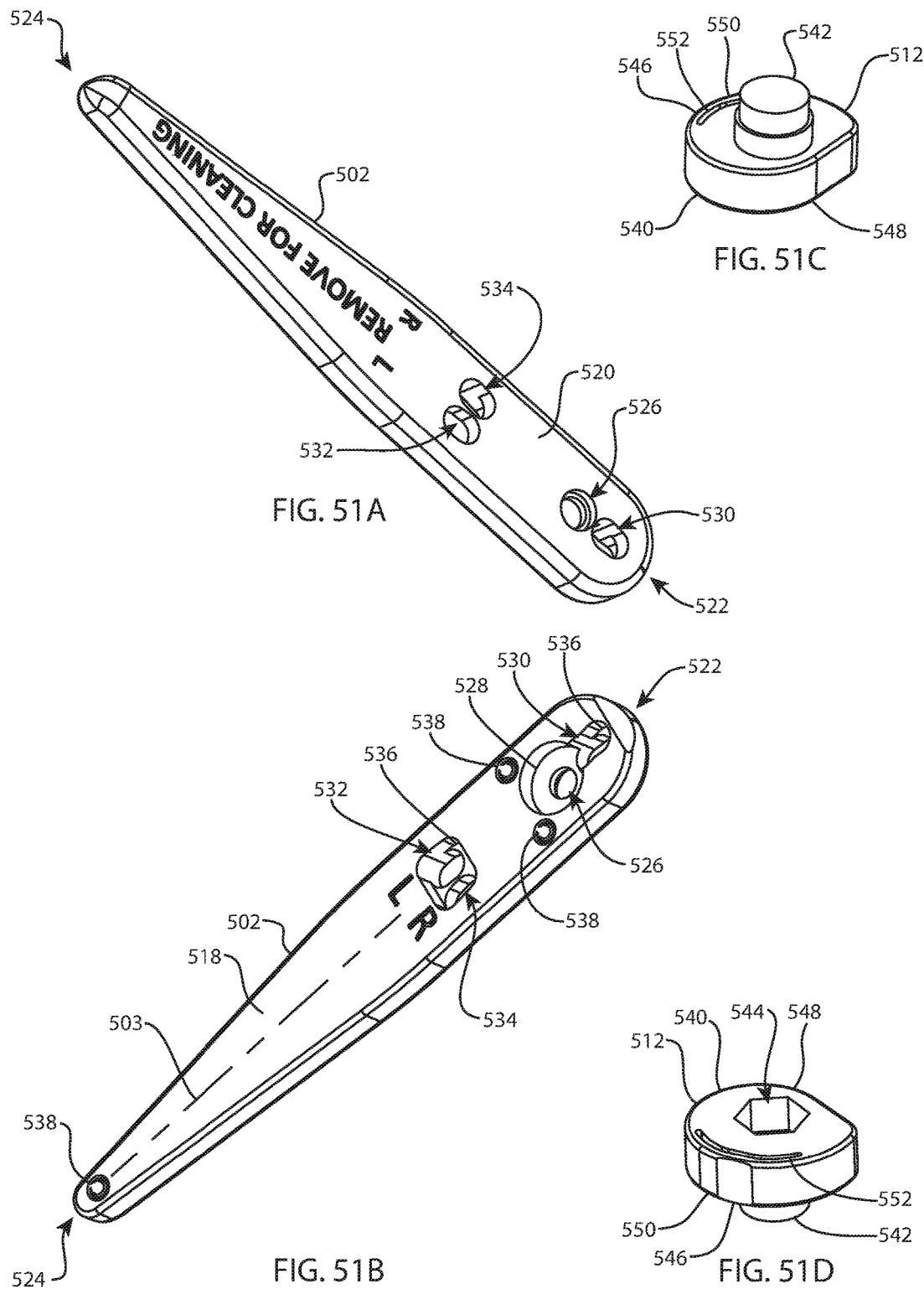

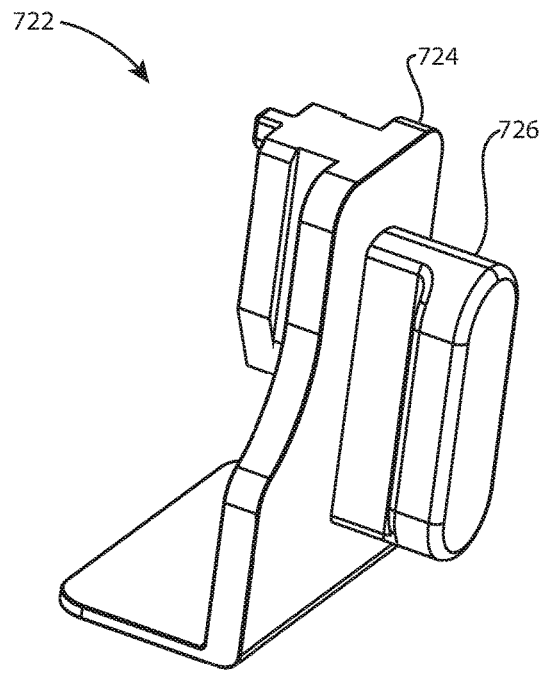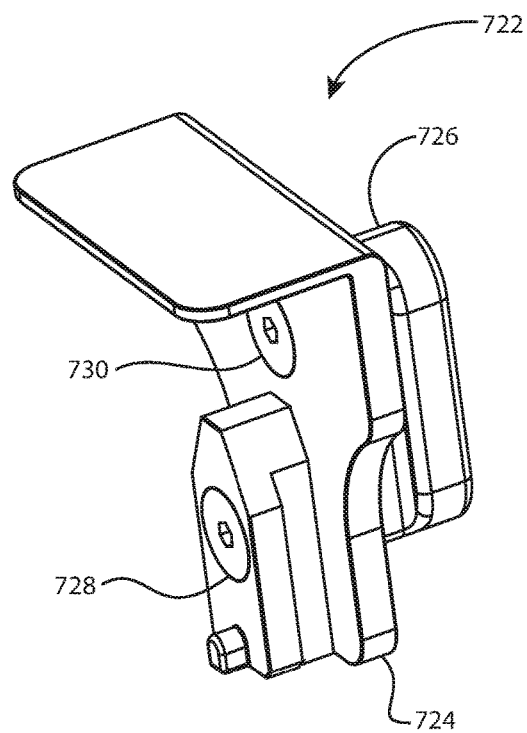
FIG. 59A   FIG. 59B
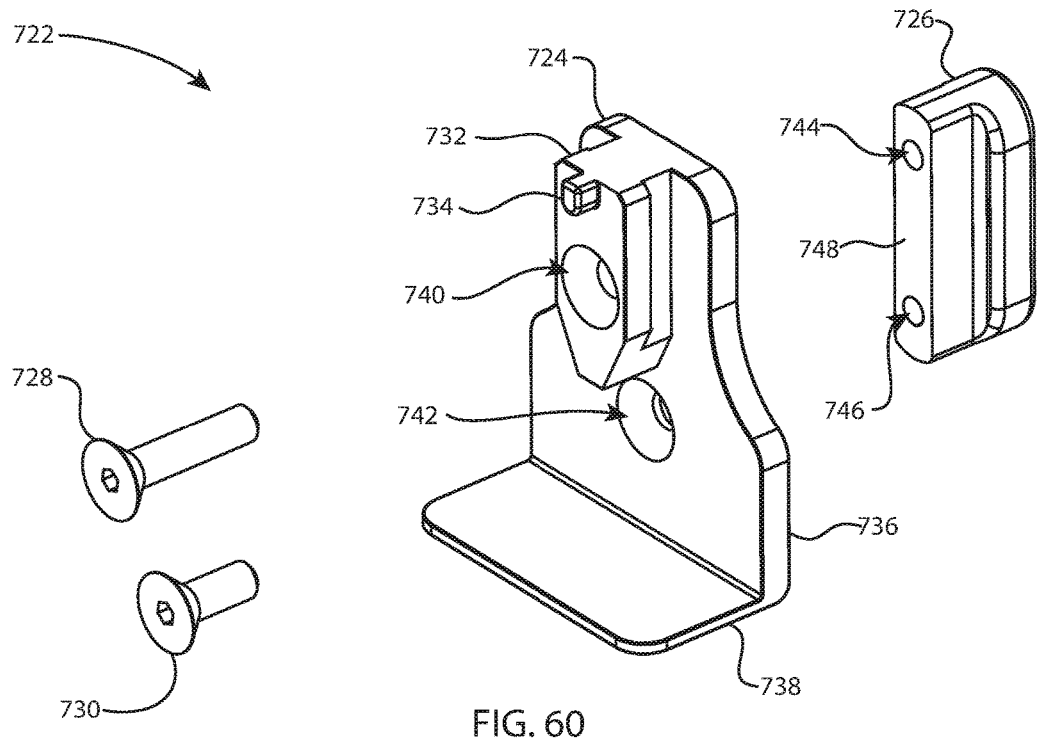
FIG. 60

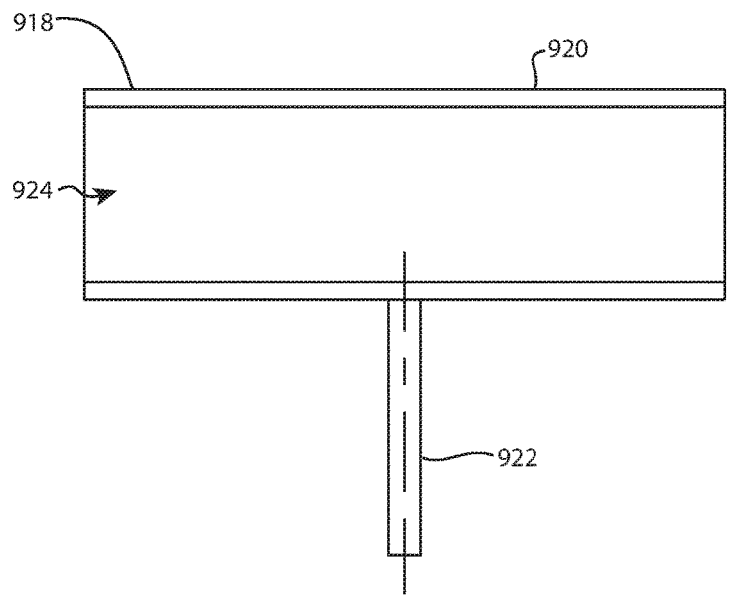
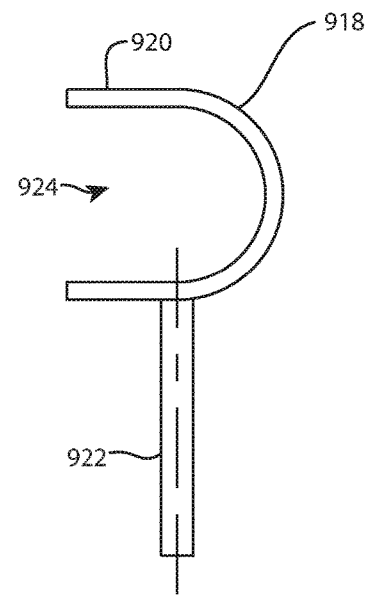
FIG. 86A    FIG. 86B
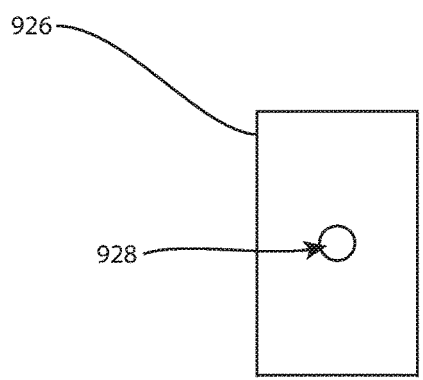
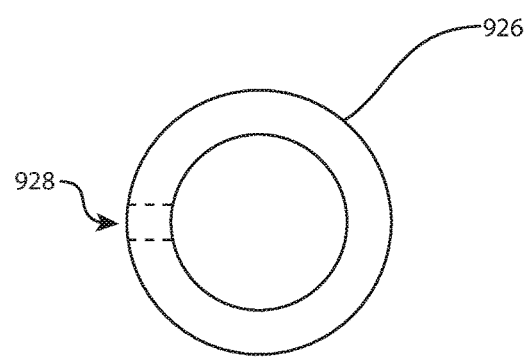
FIG. 87A    FIG. 87B

KNEE INSTRUMENTS AND METHODS

CROSS-REFERENCE TO RELATED APPLICATIONS

The present application claims the benefit of:

U.S. Provisional Application Ser. No. 62/138,307, entitled KNEE INSTRUMENTS AND METHODS, which was filed on Mar. 25, 2015; and U.S. Provisional Application Ser. No. 62/302,787, entitled KNEE INSTRUMENTS AND METHODS, which was filed on Mar. 2, 2016.

The foregoing are incorporated by reference as though set forth herein in their entirety.

TECHNICAL FIELD

The present disclosure relates to instruments and methods to improve femoral and tibial alignment during knee arthroplasty. More specifically, the present disclosure relates to instruments and methods to reference and align with the anterior distal femoral cortex, the mechanical axis of the leg, and Whiteside's line (while intact, prior to any distal femoral resection). While this disclosure is made in the context of knee arthroplasty, the principles are applicable to alignment during other arthroplasty procedures.

BACKGROUND

Traditional total knee arthroplasty instruments utilize intramedullary instruments to determine proper distal femur saw cut alignment, and extramedullary instruments to align the saw cut for the proximal tibia. Therefore it is acceptable to prepare the distal femur separate from the proximal tibia. There exists no conjoined effort to cut the distal femur and the proximal tibia as the single lower extremity body part which constitutes the knee joint.

This contemporary instrumentation process violates the principles established by Insall in the 1970s. Popular total knee arthroplasty instruments teaches this inexact intramedullary instrument process because it is simpler to teach, understand and utilize by most surgeons.

This disclosure teaches bony and soft tissue preparation of the knee joint utilizing instruments and techniques consistent with proven total knee arthroplasty instruments principles.

SUMMARY

The various systems and methods of the present technology have been developed in response to the present state of the art, and in particular, in response to the problems and needs in the art that have not yet been fully solved by currently available knee arthroplasty instrument systems and methods. The systems and methods of the present technology may provide more objective, repeatable alignment relative to important biomechanical features, compared to current systems and methods.

More specifically, the present disclosure relates to instruments and methods to reference and align with the anterior distal femoral cortex, the mechanical axis of the leg, and Whiteside's line (while intact, prior to any distal femoral resection). The anterior femoral resection is aligned in the same plane as the anterior distal femoral cortex. The center of the femoral head, the medial/lateral center of the distal femur, the medial/lateral center of the proximal tibia, and the second toe, medial/lateral center of the ankle, or anterior tibial spine or crest are all simultaneously aligned to the mechanical axis of the leg while the leg is in full extension and the knee joint is distracted. The distal femoral and proximal tibial resections are aligned relative to the mechanical axis of the leg. Since the distal femoral and proximal tibial resections may be made with the leg in full extension, a much smaller incision may be required, particularly in the quadriceps region. An eight to ten inch long incision, typical of the current state of the art, may be shortened to about six inches, with most of the savings occurring proximally in the quadriceps region. Whiteside's line is referenced while the distal femur is intact, before any distal femoral resection, and the anterior and posterior femoral resections and chamfer cuts are aligned to this reference using a jig.

The systems and methods disclosed herein provide a simple and fast way to objectively and precisely align the knee joint during arthroplasty procedures. This is inherently advantageous because malalignment predisposes a reconstructed knee to premature failure. This is particularly advantageous for those surgeons who must perform knee arthroplasty from time to time, but whose knee arthroplasty procedure volume is low. Eighty percent of knee arthroplasty procedures are performed by surgeons who do no more than two knee arthroplasty procedures per month.

The systems disclosed herein provide a cost-effective mechanical alternative to surgical navigation systems, particularly because the disclosed systems include components that are readily made as disposable items. The femoral and tibial alignment components, for example, are contemplated to be disposable items.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 1 is a perspective view of an instrument base;

FIG. 2 is a side view of the base of FIG. 1 assembled with a handle and a drill guide;

FIG. 3 is a front view of the assembly of FIG. 2;

FIG. 4 is a side view of the base of FIG. 1 assembled with a cut guide assembly;

FIG. 5 is a top view of the assembly of FIG. 4;

FIG. 6 is a front view of the assembly of FIG. 4;

FIG. 8 is a top view of a step in a surgical procedure, elevating the suprapatellar fat pad;

FIG. 9 is a top view of a step in a surgical procedure, inserting the base of FIG. 1 against the anterior distal femoral cortex;

FIG. 21A is a perspective view of another instrument system; and FIG. 21B is an enlarged detail view of a portion of the instrument system of FIG. 21A;

FIG. 25A is a perspective view of a femoral riser, or handle, of the instrument system of FIG. 21A; and FIG. 25B is another perspective view of the femoral riser of FIG. 25A from a different direction;

FIG. 26A is a perspective view of a femoral extension rod of the instrument system of FIG. 21A; and FIG. 26B is another perspective view of the femoral extension rod of FIG. 26A from a different direction;

FIG. 30A is a perspective view of a tibial outer extension rod of the instrument system of FIG. 21A; and FIG. 30B is another perspective view of the tibial outer extension rod of FIG. 30A from a different direction;

FIG. 51A is a perspective view of the base of FIG. 50A; FIG. 51B is another perspective view of the base of FIG. 51A from a different direction; FIG. 51C is a perspective view of a cam for use with the base of FIG. 50A; and FIG. 51D is another perspective view of the cam from a different direction;

FIG. 59A is a perspective view of a cut guide mounting block assembly for use with the angle block assembly of FIG. 56A; and FIG. 59B is another perspective view of the cut guide mounting block assembly of FIG. 59A from a different direction;

FIG. 60 is an exploded perspective view of the cut guide mounting block assembly of FIG. 59A;

FIG. 86A is a bottom view of a femoral head finder; and FIG. 86B is a side view of the femoral head finder of FIG. 86A;

FIG. 87A is a front view of a collar; and FIG. 87B is a side view of the collar of FIG. 87A.

DETAILED DESCRIPTION

Figure 7:
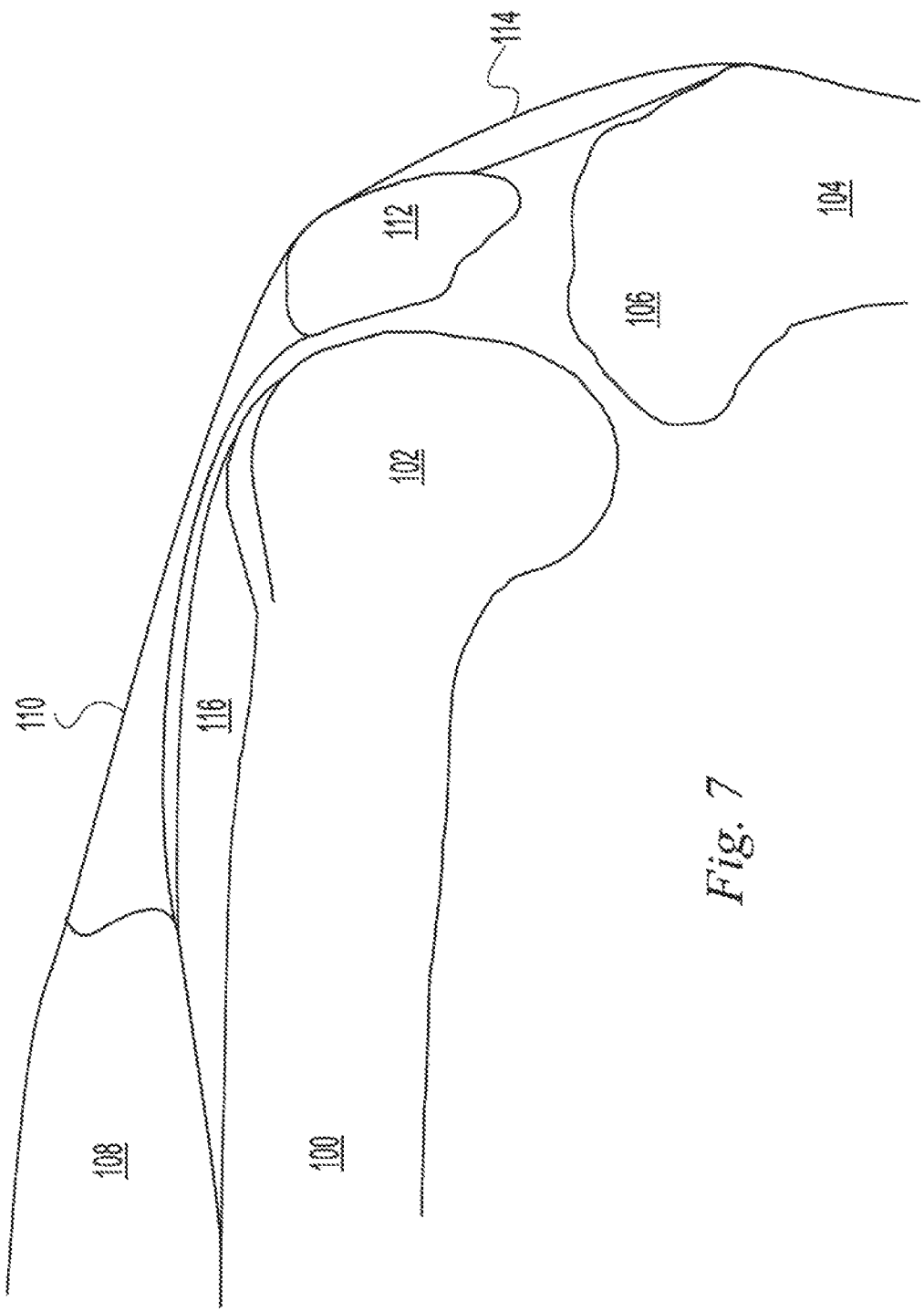
FIG. 7 is a side view of certain anatomical structures of the human knee in cross section.

Exemplary embodiments of the technology will be best understood by reference to the drawings, wherein like parts are designated by like numerals throughout. It will be readily understood that the components of the system, as generally described and illustrated in the figures herein, could be arranged and designed in a wide variety of different configurations. Thus, the following more detailed description of the embodiments of the apparatus, system, and method is not intended to limit the scope of the invention, as claimed in this or any other application claiming priority to this application, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A midsagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Standard terminology related to knee arthroplasty is employed in this specification. Varus means deviation of the distal part of the leg below the knee inward, resulting in a bowlegged appearance. Valgus means deviation of the distal part of the leg below the knee outward, resulting in a knock-kneed appearance.

ABBREVIATIONS AND NOMENCLATURE

TKAI Total Knee Arthroplasty Instruments, Instrumentation
I Instruments, Instrumentation, or the like
AL Alignment
Fe Femur, Femoral, or Femur-related
Ti Tibia, Tibial, or Tibia-related
EG Extension Gap
FG Flexion Gap
FR Femoral Rotation
TS Tibial Slope
PS Posterior Stabilized
CR Cruciate Retaining
Kn Knee
AIS Anterior Iliac Spine
FeHe Femoral Head
IM Intramedullary
EM Extramedullary
DAFe Distal Anterior Femur Traditional TKAI utilizes IM I to determine proper distal femur saw cut alignment, and EM I to align the saw cut for the proximal tibia. Therefore it is acceptable to prepare the distal femur separate from the proximal tibia. There exists no conjoined effort to cut the distal femur and the proximal tibia as the single lower extremity body part which constitutes the knee joint.

This contemporary instrumentation process violates the principles established by Insall in the 1970s. (Insall, John N. Surgery of the Knee. New York: Churchill Livingstone, 1984. Pages 631-365. Entire book incorporated by reference in its entirety.) Popular TKAI teaches this inexact IM I process because it is simpler to teach, understand and utilize by most surgeons. This contradiction is best illustrated by examining the long time relationship of Zimmer, Inc. and one of its premier consultants, Dr. Bob Booth (Philadelphia). Dr. Booth successfully and famously performs exact TKAI utilizing his mentor's (Dr. Insall's) principles. However, Zimmer does not commercialize Dr. Booth's instruments and techniques because the technique proves too technically difficult for most surgeons.

This disclosure teaches bony and soft tissue preparation of the knee joint utilizing instruments and techniques consistent with proven TKAI principles.

Technique

A longitudinal incision 150 is made from proximal to distal with its mid point over the anterior knee. A medial arthrotomy is performed in standard fashion. The patella 112 is everted and dislocated laterally as the knee is flexed to 90 degrees. The medial and lateral supporting ligaments of the knee are balanced as needed.

The proximal tibia 106 is resected at a right angle to the long axis of the tibia 104, removing approximately 6 mm to 10 mm of bone (in traditional fashion utilizing a tibial cut guide referencing the anterior tibial spine). However, this may be a provisional resection that removes 3 mm to 5 mm of bone to increase the working space inside the knee joint.

The lower extremity (and knee) is now positioned in full extension (0 degrees flexion). The full extension of the knee relaxes the extensor mechanism. The suprapatellar fat pad 116 is elevated from the anterior distal femur 102 with a small periosteal elevator 154 (elevating the fat layer from the anterior femur only—leaving the fat pad attached medial and lateral on the femur).

An instrument is now inserted, from distal to proximal, externally along the distal anterior femoral cortex under the suprapatellar fat pad 116. This instrument somewhat resembles a bone plate, having a (longitudinal) distal to proximal length longer than its medial to lateral length (width). This instrument is referred to as a base 10. Rising from the distal end of this unattached plate, residing on the anterior cortex of the distal femur 102, is an element containing a series of stacked directional holes 14, 16, 18 which align themselves with each axis of each hole pointing (proximal) toward the head 118 of the femur 100. The axis of each of these directional holes is 5 degrees valgus to the distal anterior femoral cortical plate or base 10, previously described. This 5 degree divergence angle varies in absolute direction (relative to mid line of the body) depending upon right or left knee undergoing this surgery.

In a design, a "hinged" rod is attached, through two of the longitudinal stacked holes so as to align the direction of this rod in the direction of the head 118 of the femur. The "hinged" rod is referred to as an alignment rod 156. The proximal end of the rod, once deployed, will be positioned over the mid portion of the head 118 of the femur, and preferably directly over the center 120 of the femoral head 118. This important reference point is determined to be 1) two finger breadths medial to the anterior superior iliac spine or, much better, 2) determined by fluoroscopy, radiographs, C-arm, or the like.

The significance of this reference rod 156 is 1) its attachment as part of the femoral "plate" or base 10 residing on the anterior surface of the distal femur. The medial/lateral position of the proximal end of the rod can be changed by simply and minimally moving the proximal end of the femoral "plate" medially (thus increasing the valgus of the distal femoral cut) or laterally (increasing the varus) to the midline of the distal anterior femoral cortex. Preferably, the distal end of the rod 156 is attached to the base 10 so that the rod passes directly over the medial/lateral center of the distal femur, and the proximal end of the rod 156 is moved medial/lateral until the rod passes directly over the center 120 of the femoral head 118.

Once alignment is obtained, 2 screws are driven into slots in the distal end of the femoral "plate" or base 10, in order to secure alignment. These 2 screws may be placed outside of the cutting path for the anterior femoral resection 214 so that the cut can occur without hitting the screws.

A parallel handle 21 is attached to the distal femur cortical "plate" which attaches these two parallel elements distally (but not proximally), and is anterior and separate to the soft tissues of the distal thigh. This parallel "plate" handle 21 permits compression to be applied to the distal femur cortical "plate" or base 10 by the surgeon in order to prevent movement (medial or lateral) of the plate from the desired alignment position (with respect to femoral head 118). Small, sharp "cleats" may be included on the bone-facing surface of the base 10 to increase friction contact of the "plate" to the distal anterior femoral bone.

Once femoral alignment is secured, the "hinged" rod is moved from (proximal) reference to the hip, to distal reference of the lower extremity, i.e. the anterior tibial spine or crest, ankle, and/or second toe of the foot. This mechanical connection of 1) alignment of the femur 100 to the 2) alignment of the tibia 104—through rotation of the "hinged" rod 156 from proximal extremity to distal extremity (while the knee remains unmoved and in full extension) permits direct alignment of the proximal extremity (femur 100) with the distal extremity (leg or tibia 104) along the mechanical axis 202 of the leg.

Now, the ankle/foot region of the lower extremity can simply be moved (lateral or medial) under the distal end of the "hinged" rod 156 to align the entire lower extremity (hip, knee, ankle) in an exact straight line along the mechanical axis 202 of the leg.

The "hinge" aspect of the rod 156 permits proximal alignment referencing the femoral head 118 without being adversely affected by obesity (the rod angles superiorly over a large mid section without compromising alignment with the femoral head 118).

The "hinged" rod 156 now rotated distally and placed exactly parallel with the lower extremity (through an articulation at the hinge point) (referencing the plane of the distal anterior femoral cortex), can allow proper attention and calibration for the (final) angle of cut for the proximal tibial cut (previously rough cut).

This means that the desired posterior slope of the tibial cut can now be referenced off of the exact alignment of the entire length of the lower extremity, through reference to the distal anterior femoral cortex making the distally positioned "hinged" rod parallel to the distal anterior femoral cortex by a short extension of the deployed "hinged" rod extending proximally parallel to the femoral cortex and finally reaching distally until referencing the ankle or 2nd toe of the foot.

Cutting guides for the distal femur and (simultaneously) proximal tibia are hung from the deployed "hinged rod" 156. While the "hinged" rod is overlying the entire tibia 104, the knee joint is distracted until the collateral ligaments of the knee are "very" taut (knee still in full extension) and the center of the ankle is under the distal rod 156. Once properly and fully distracted and aligned, a four point drill guide (attached at a right angle from the "hinged" rod) is positioned anterior to the knee joint.

The midpoint of this four point drill guide is positioned at the natural joint line. Now, each of the four points of the drill guide (positioned about 20+mm apart—equal to the sum width [thickness] of the intended tibial and femoral prostheses—in extension) are utilized to drill holes (2 each and [all] parallel) in the distal femur and the proximal tibia. Extended, shouldered studs are now placed in each of the drill holes in anticipation of saw guides being positioned by matching receiving holes in the cut plates (one for the distal femur and the other for the proximal tibia).

The distraction device is relaxed and removed from the knee. The cut guides are placed over the shouldered studs. The knee is now flexed (the "hinged" rod elevated and drawn proximally over the femur) and each of the two cuts are now made, aligned and properly angled (proximal tibia) by the two cut guides—femur and tibia.

The "hinged rod" attachment to the riser (on the femoral "plate") is now advanced distally by extension through the two stacked holes in the riser, so to match the end of the cut femur. The knee is flexed to 90 degrees. The "hinged" rod is now deployed distally and allowed to flex to 90 degrees at its riser hinge. At 90 degrees flexion the rod will now cross the cut surface of the femur and parallel the anterior spine of the tibia.

To adjust for femoral rotation, a technique is now employed. The "hinged" rod is made parallel to Whiteside's line (middle of anterior and distal femur extending through middle of cut surface of femur [from the bottom of the trochlear groove to the top of the intercondylar notch (trochlear notch), at right angles to the epicondylar axis, which is a line between the most prominent points of the medial and lateral epicondyles, or a line connecting the lateral epicondylar prominence and the medial sulcus of the medial epicondyle]), and then the femur adjusted on the tibia so that Whiteside's line and the anterior spine of the tibia are in perfect alignment.

A multi-cut guide is now deployed with a right angle rod attachment within the femoral anterior cortex "plate". This rod extension attached to the top of the multi-cut femoral guide will permit (for the first time) perfect reference to cutting the anterior and distal femur—by allowing the anterior cut slot to aim directly, proximal, to the base of the femoral "plate". The guide will allow anterior and posterior adjustment of up to 2 mm to allow surgeons to (mildly) notch the femur, or even rise anterior to the anterior cortex—the choice is made by the surgeon depending on his interest in the sight of the posterior femoral cut (more or less bone posteriorly).

As discussed in the above paragraphs, femoral rotation is adjusted relative to Whiteside's line and the tibial cut (right angle to it) and then the multi-cut guide is pinned to the distal femur, and all chamfer cuts and anterior and posterior cuts are thus made, directly related to and reference to, the companion member of the knee joint.

Instruments

Base 10 (datum) (FIG. 1) includes trunnion 12 and screw holes 14, 16, 18.

The base 10 may be modified so that one (lateral, medial, or posterior) side of the base registers on an anatomic ridge or other structure or detail of the distal anterior femur. More than one (lateral, medial, or posterior) side of the base may be modified to register on anatomic structures or details of the distal anterior femur. The anatomic structures or details may be protruding features, such as ridges, or recessed features, such as sulci, fossae, grooves, or other depressed features.

Drill guide assembly 20 (FIGS. 2-3) includes handle 21, socket end 22, drill guide 24, handle 26, and tube 28.

Cut guide assembly 30 (FIGS. 4-6) includes pivot block 31, arm 32, and anterior femoral cut guide 34. The anterior femoral cut guide 34 includes cut slot 36 aligned with posterior surface 38 of base 10 so that anterior femoral resection 214 is flush with the distal anterior femoral cortical surface on which the base is mounted. This means that the posterior surface 38, cut slot 36, and the anterior femoral resection 214 all lie in a common plane. The cut guide assembly 30 also includes posterior femoral cut guide 40; linked to anterior femoral cut guide 34; adjustable on rails 42 for A/P distance; locked with set screws 44; sizes may be etched on rails and/or size may be set with feeler gauges and the actual implant and/or with calipers; The posterior femoral cut guide 40 may include optional posterior condylar abutment tabs 46 or optional pin/screw fixation holes 47. The cut guide assembly 30 also includes proximal tibial cut guide 48, which mounts to the posterior femoral cut guide 40 and may be available in various sizes to match measured flexion gap. The proximal tibial cut guide 48 may mount to the posterior femoral cut guide 40 via dovetail engagement 50, with an optional locking screw. The proximal tibial cut guide 48 may include optional pin/screw fixation holes 52.

Anatomy

FIG. 7: femur 100, distal femur 102, tibia 104, proximal tibia 106, quadriceps muscle 108, patellar ligament 110, patella 112, patellar tendon 114, and suprapatellar fat pad 116. FIG. 8: femoral head 118 and center 120 of the femoral head 118.

Figures 18, 19:
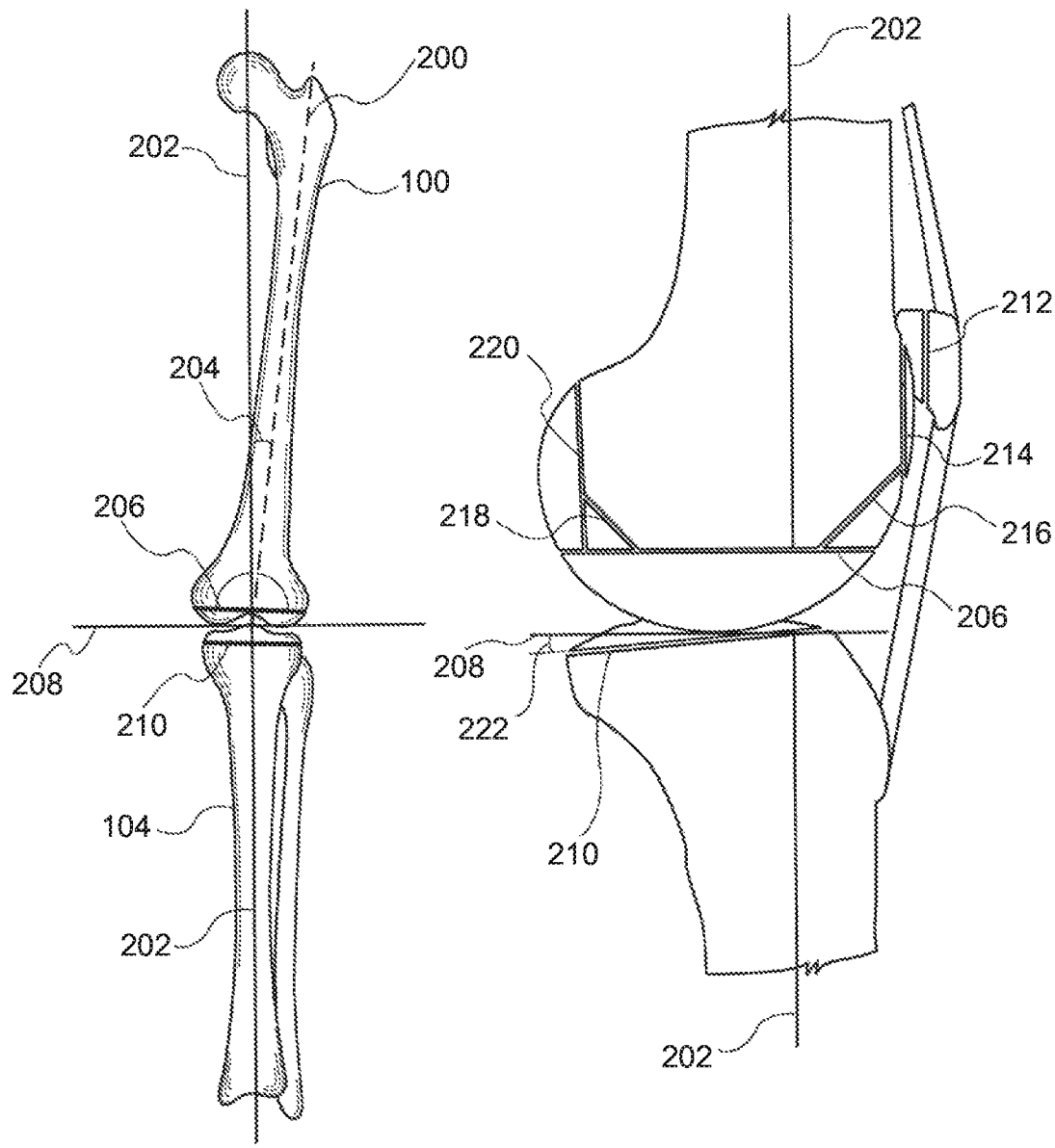
FIG. 18 is a front view of certain anatomical landmarks and geometry of the human knee and leg.
FIG. 19 is a side view of certain anatomical landmarks and geometry of the human knee.

FIG. 18: femoral shaft axis 200, mechanical axis 202 of the leg, angle 204 between femoral shaft axis 200 and mechanical axis 202 of the leg, distal femoral resection 206, knee joint line 208, proximal tibial resection 210.

FIG. 19: patellar resection 212, anterior femoral resection 214, anterior femoral chamfer cut 216, posterior femoral chamfer cut 218, posterior femoral resection 220, angle 222 between knee joint line 208 and proximal tibial resection 210.

Figure 20:
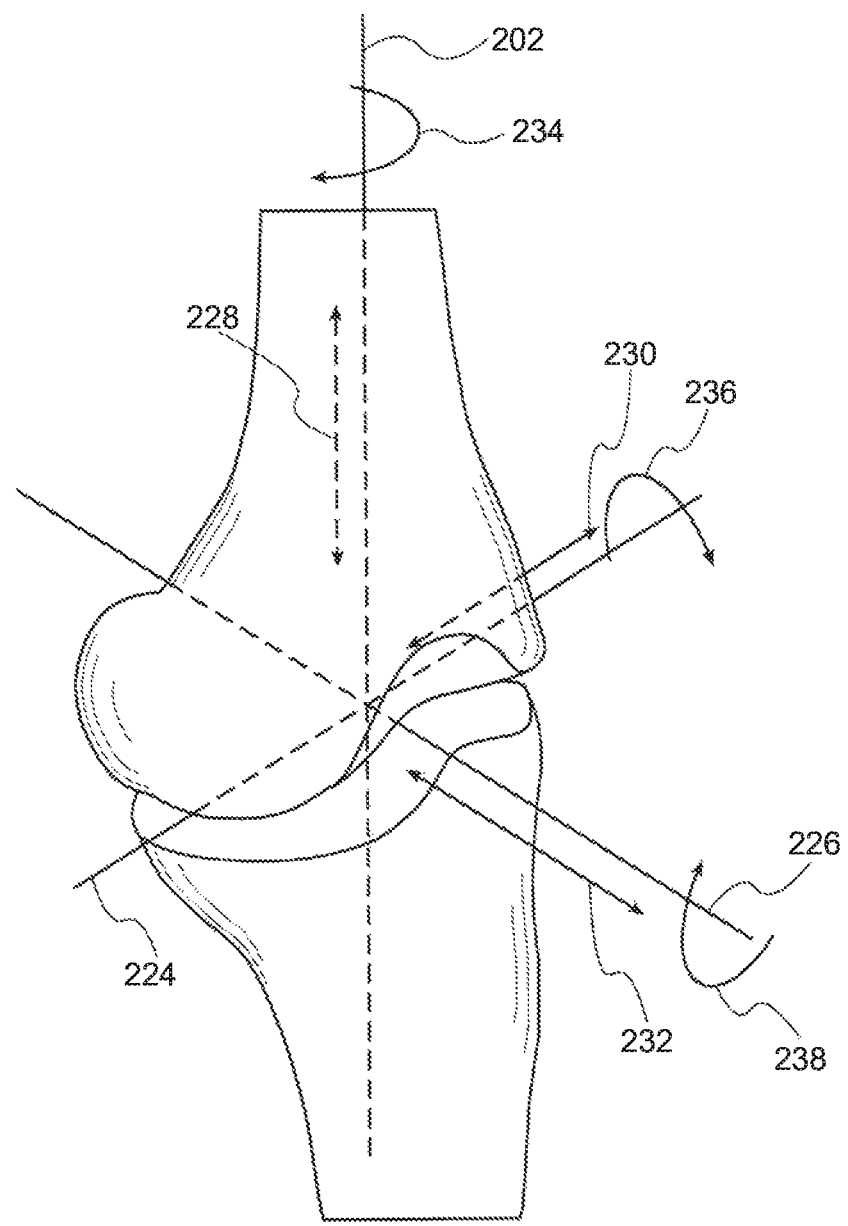
FIG. 20 is a perspective view of the femur and tibia of the human knee.
Figure 22A:
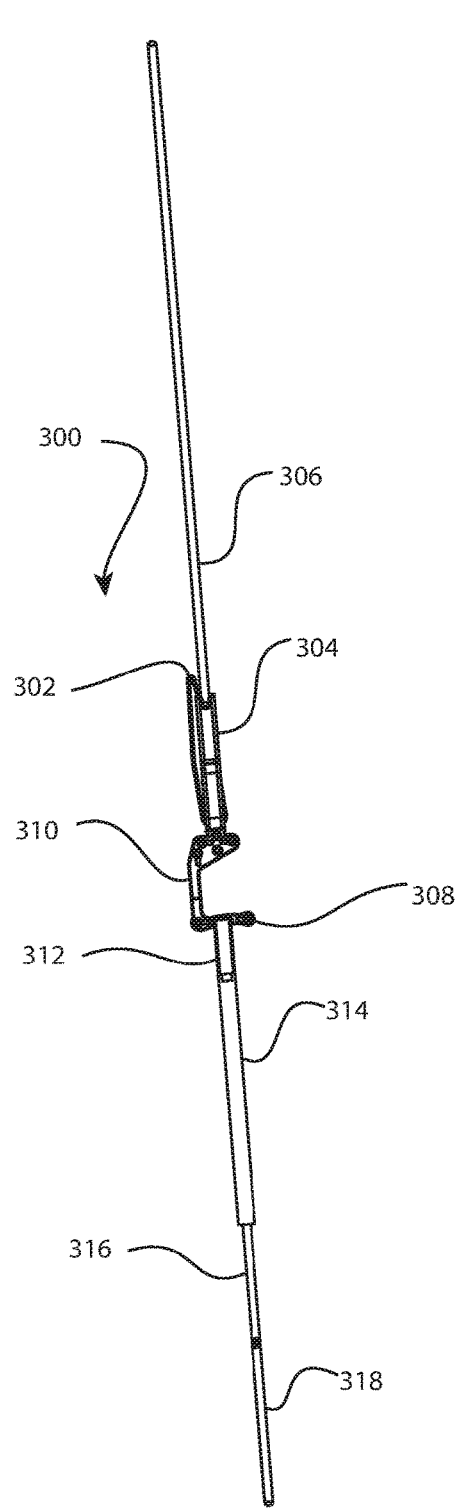
FIG. 22A is a top view of the instrument system of FIG. 21A.
Figure 22B:
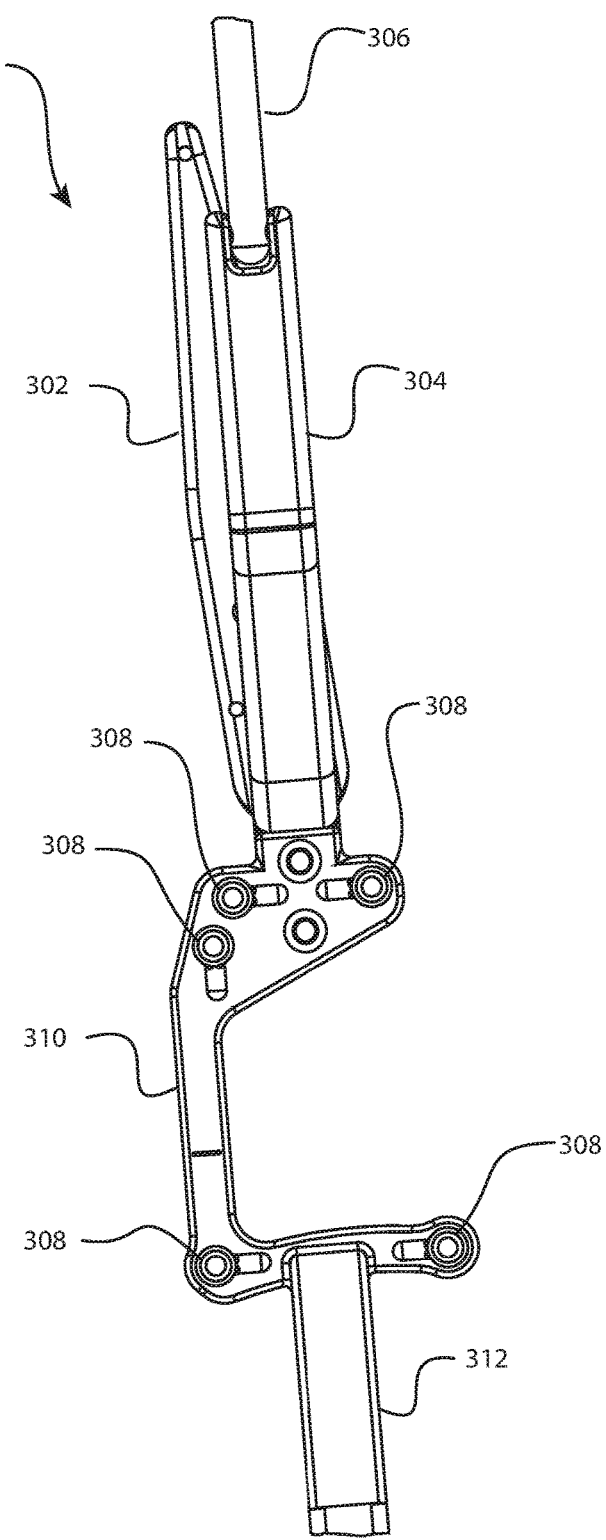
FIG. 22B is an enlarged detail view of a portion of the instrument system of FIG. 22A.

FIG. 20: transverse axis 224 of the knee (may also be the axis about which the knee flexes and extends), anterior-posterior axis 226 of the knee (may also be the axis about which the knee goes into varus and valgus), superior-inferior translation 228 along the mechanical axis 202 of the leg, medial-lateral translation 230 along the transverse axis 224 of the knee, anterior-posterior translation 232 along the anterior-posterior axis 226 of the knee, axial rotation 234 about the mechanical axis 202 of the leg, rotation 236 about the transverse axis 224 of the knee (also known as flexion and extension), rotation 238 about the anterior-posterior axis 226 of the knee (also known as varus-valgus rotation).

Method

Figure 10:
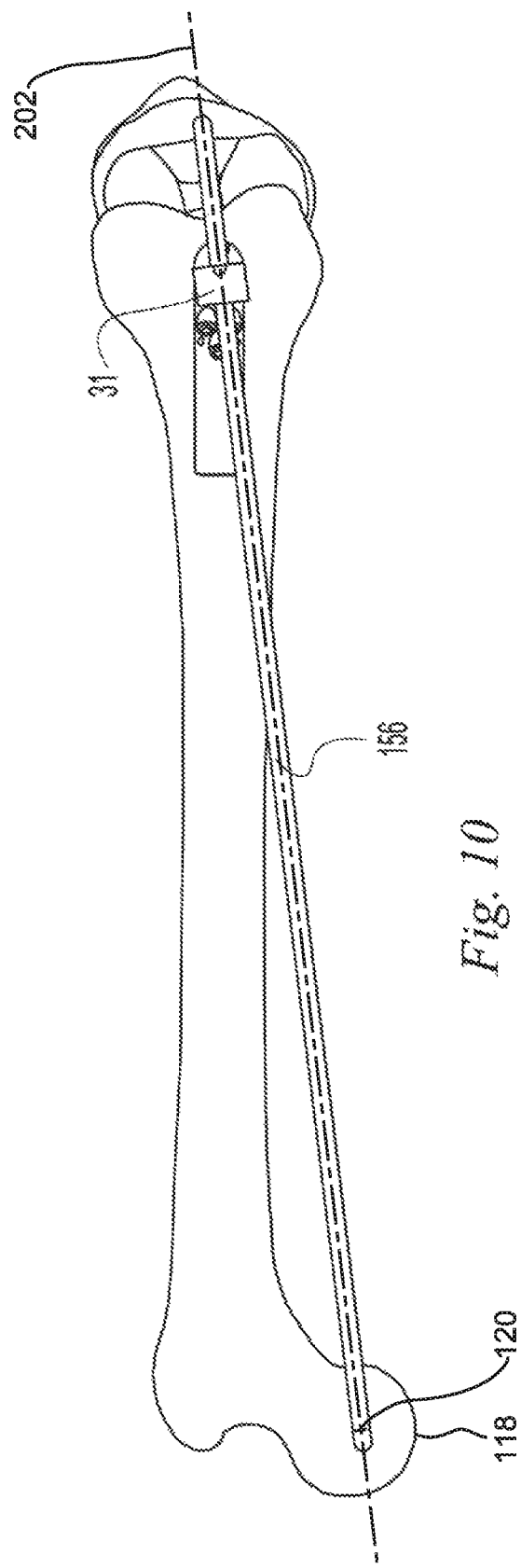
FIG. 10 is a top view of a step in a surgical procedure, aligning a femoral extension rod over the center of the femoral head and the medial/lateral center of the distal femur to establish a mechanical axis of the leg.

Mounting the base 10 to the distal anterior femoral cortex (FIGS. 8-10) may include the steps of making an incision 150, everting the patella 112, resecting the distal margin 152 of the fat pad 116, blunt dissection such as with an elevator 154 under the fat pad along the midline of the femoral shaft, inserting the base 10 under fat pad 116 with the base 10 aligned with the femoral shaft and centered in the medial/lateral width of the distal femur (epicondylar width), using drill guide 20 to drill two holes through base 10 into femur 100, drilling proximal hole through muscle and fat pad, tapping if desired/necessary, and anchoring base to femur with screws.

Aligning the pivot block 31 with the mechanical axis 202 of the leg (FIG. 10) may include the steps of using the alignment rod 156 and locking the pivot block 31. With the pivot block 31 unlocked so that it is free to rotate, the alignment rod 156 is positioned over the femoral head 118 and moved medial/lateral until the rod passes directly over the femoral head center 120. The pivot block 31 is then locked to prevent any further medial/lateral rotation. However, the alignment rod 156 is still free to swing between proximal and distal positions.

Figure 11:
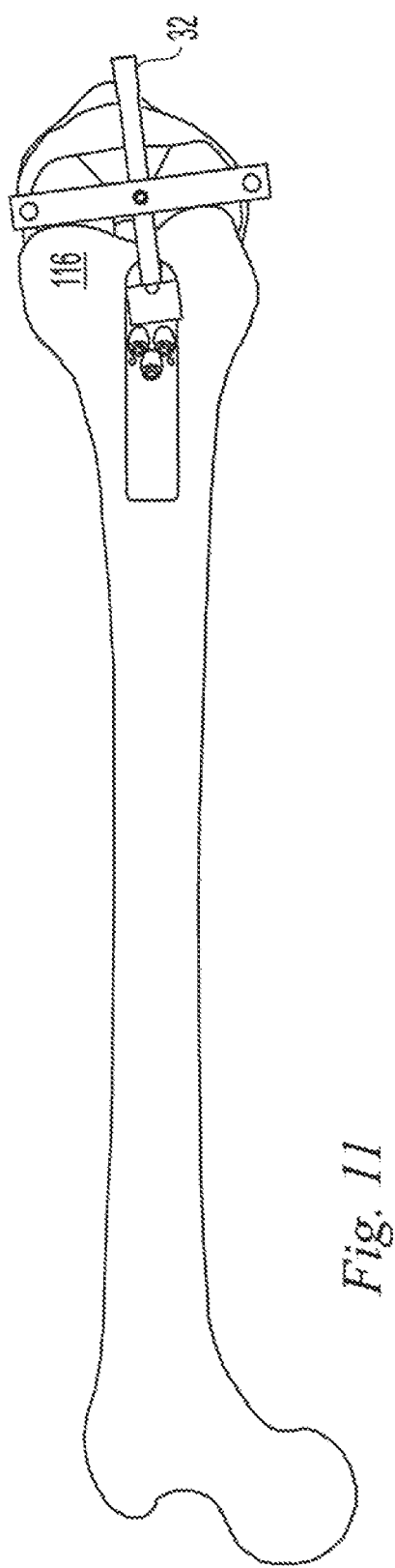
FIG. 11 is a top view of a step in a surgical procedure, aligning a femoral cut guide to the mechanical axis of the leg.
Figure 12:
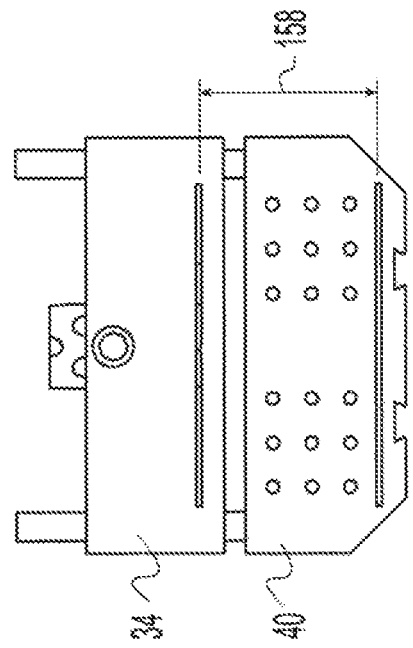
FIG. 12 is a front view of the cut guide assembly of FIG. 4 configured for making femoral cuts.
Figure 13:
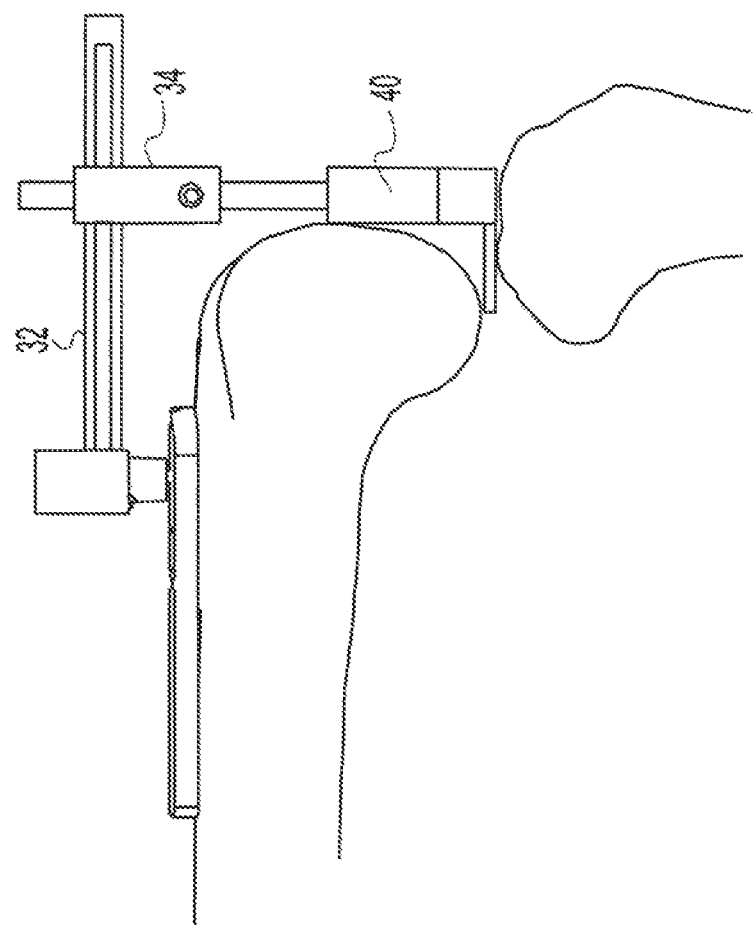
FIG. 13 is a side view of the surgical step of FIG. 11.
Figure 14:
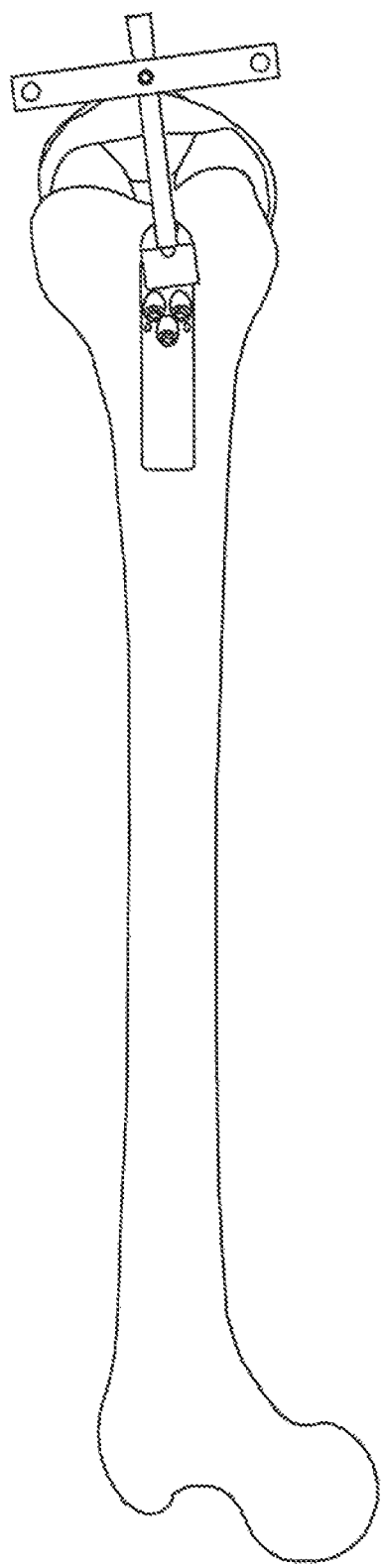
FIG. 14 is a top view of a step in a surgical procedure, aligning a tibial cut guide to the anterior tibia.
Figure 15:
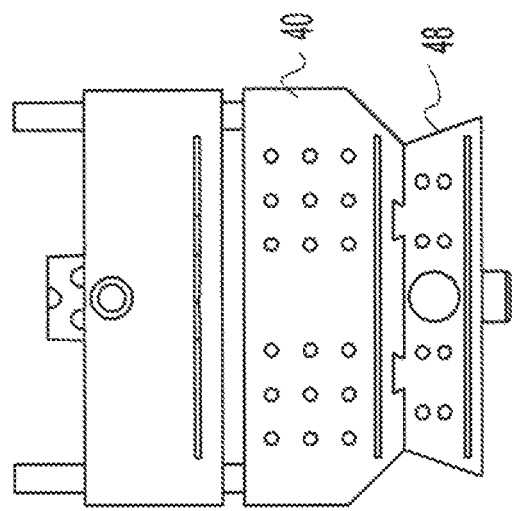
FIG. 15 is a front view of the cut guide assembly of FIG. 4 configured for making a tibial cut.

Making the femoral cuts (FIGS. 11-13) may include the steps of adjusting the femoral cut guides 34, 40 to match A/P femoral dimension 158 of templated femur size, flexing knee to 90 degrees, mounting arm 32 and femoral cut guides 34, 40 to pivot block 31, sliding cut guides into contact with distal femur, optionally adding pins or screws to secure posterior cut block to femur, and making anterior and posterior femoral cuts, e.g. with a powered oscillating saw or other cutting tool.

Figure 16:
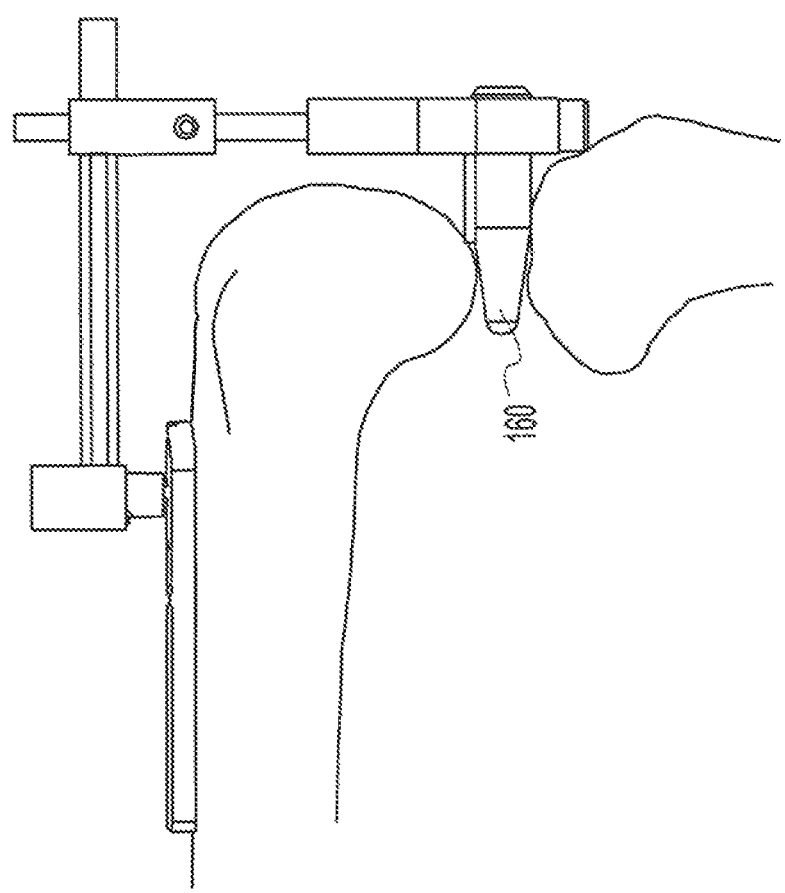
FIG. 16 is a side view of the surgical step of FIG. 14 illustrating the use of a joint distraction member.
Figure 17:
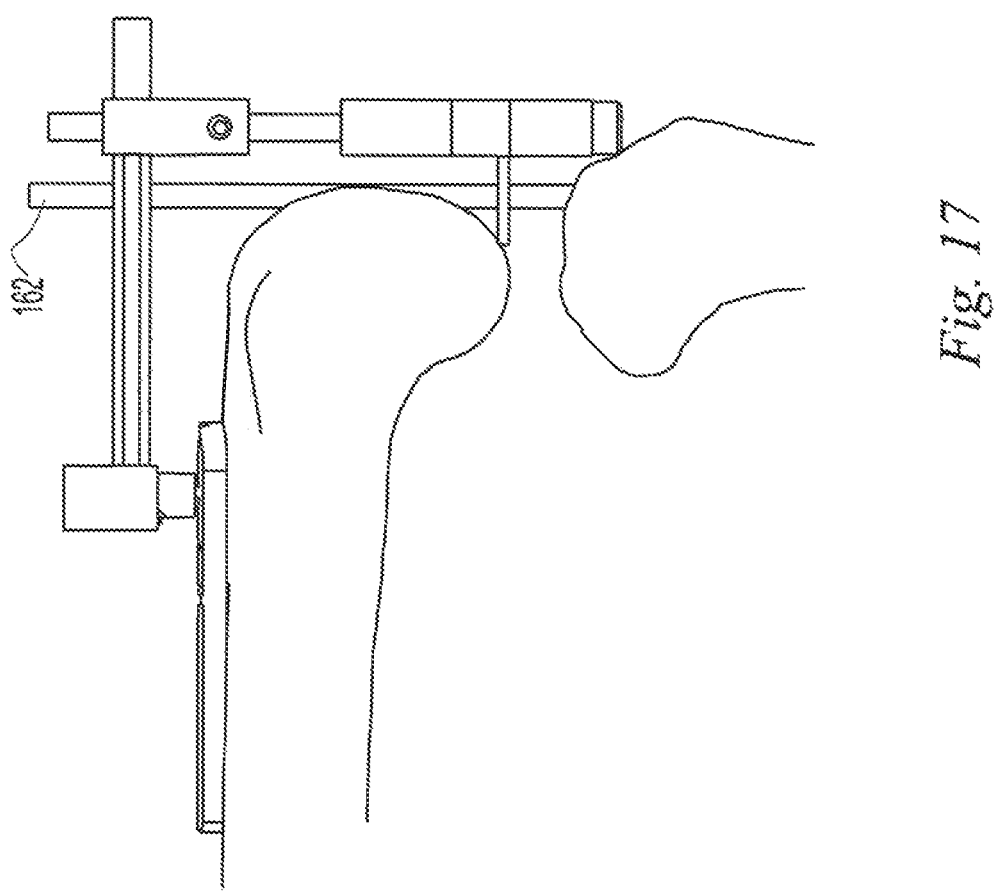
FIG. 17 is a side view of the surgical step of FIG. 14 illustrating the use of another joint distraction member.

Making the tibial cut (FIGS. 14-17) may include the steps of determining flexion gap with spacers (as is known in the art) to produce desired tension in flexion, selecting proximal tibial cut guide 48 to match measured gap, sliding femoral cut guides 34, 40 away from femur, mounting proximal tibial cut guide 48 to posterior femoral cut guide 40, sliding cut guides 40, 48 into contact with proximal tibia, tensioning joint (wedge 160 FIG. 16 or screw 162 through arm 32 FIG. 17), optionally adding pins or screws to secure proximal tibial cut block to tibia, and making proximal tibial cut.

Adjustments and remaining cuts may be made as known in the art, for example flexion and extension gap adjustments via soft tissue release or recutting bone, marginal osteophyte removal, distal femoral cut, and chamfer cuts.

Referring to FIGS. 21A-23B, another instrument system 300 is shown. This instrument system 300 is designed so that bone pins may be placed in the distal femur 102 and proximal tibia 106 while the knee joint is in full extension and maximally distracted, while referencing the distal anterior femoral cortex, and while the leg (femoral head center 120, distal femur 102, proximal tibia 106, and ankle/second toe/anterior tibial spine or crest) is properly aligned with the mechanical axis 202 of the leg. The bone pins serve as mounting fixtures for subsequent instruments, such as cut guides. The system 300 includes apparatus for referencing Whiteside's line while the distal femoral condyles are intact, before any femoral resection occurs, and locking this reference into the apparatus to guide later surgical steps. This design has advantages for, and may be used for, many types of knee arthroplasty, such as bicompartmental or bicondylar knee arthroplasty where the prosthetic components replace and extend across the medial and lateral compartments (with or without a prosthetic patellar component), or unicompartmental or unicondylar knee arthroplasty where the prosthetic components replace the medial or lateral compartment or a single condyle. This design may also be advantageous when replacing the medial and lateral compartments with independent medial and lateral unicompartmental prosthetic components, for example, to spare the anterior cruciate ligament (ACL).

The instrument system 300 may include a base 302, a femoral riser 304 (also known as a handle), a femoral extension rod 306, a tapered plug assembly 308, a tibial-femoral pin guide 310, a tibial riser 312, and a tibial extension rod 313. The instrument system 300 is shown with five tapered plug assemblies 308 (FIG. 21B) and a three-piece telescoping tibial extension rod 313 including a tibial outer extension rod 314, a first tibial inner extension rod 316, and a second tibial inner extension rod 318. The instrument system 300 may also include additional components as described below for FIGS. 21A-46.

Referring to FIGS. 24A-25B, the femoral riser 304, or handle, may be rigidly coupled to the base 302 in one or more orientations. FIGS. 24A-25B illustrate an arrangement in which the femoral riser 304 may be coupled to the base 302 in two orientations. The base 302 includes two slots 344, 346 recessed in a top surface 348 of the base. An acute angle 345 is formed between the slots 344, 346. The magnitude of the angle 345 may be related to the angle 204 between the femoral shaft axis 200, represented by a longitudinal axis 301 of the base 302, and the mechanical axis 202 of the leg (FIG. 18), represented by a longitudinal axis 311 of the femoral riser 304. In the illustrated example, angle 345 may be two times angle 204. The femoral riser 304 includes a ridge 350, or tab, which is received in one of the slots 344, 346 when the femoral riser 304 is coupled to the base 302. The base 302 also includes three holes 352, 354, 356 which are arranged adjacent to the ends of the slots 344, 346. In this example, three holes are sufficient since the slots intersect on the base 302; four holes would be more appropriate if the slots did not intersect on the base 302, and in general the number of holes varies according to the number and arrangement of slots on the base. The femoral riser 304 includes two holes 358, 360 which are arranged adjacent to the ends of the ridge 350. When the ridge 350 is inserted in slot 344, a fastener may be inserted through holes 358, 352, and another fastener may be inserted through holes 360, 356. When the ridge 350 is inserted in slot 346, a fastener may be inserted through holes 358, 352, and another fastener may be inserted through holes 360, 354.

Referring to FIGS. 25A-26B, the femoral extension rod 306 may be pivotally coupled, or hinged, to the femoral riser 304 by a pin, screw, or other fastener through holes 305, 307. Hinge 309 is shown in FIGS. 21B and 23B. The femoral extension rod 306 may remain coupled to the femoral riser 304 in service. In use, the femoral extension rod 306 is free to pivot about the hinge 309 to adjust to the patient's anatomy. The femoral extension rod 306 pivots in an anterior-posterior direction which is generally parallel to the sagittal plane. The femoral extension rod 306 is constrained against pivoting in a medial-lateral direction which is generally parallel to the coronal plane.

Referring to FIGS. 25A, 25B, 28A, and 28B, the tibial-femoral pin guide 310 may be rigidly coupled to the femoral riser 304 by engaging a tab 362 of the femoral riser 304 (FIG. 25A) in a slot 364 of the tibial-femoral pin guide 310 (FIG. 28B) and inserting fasteners through holes 366, 370 and holes 368, 372. Alternatively, the tibial-femoral pin guide 310 may be coupled to the femoral riser 304 by engaging the tab 362 in the slot 364 without using fasteners.

Figure 27A:
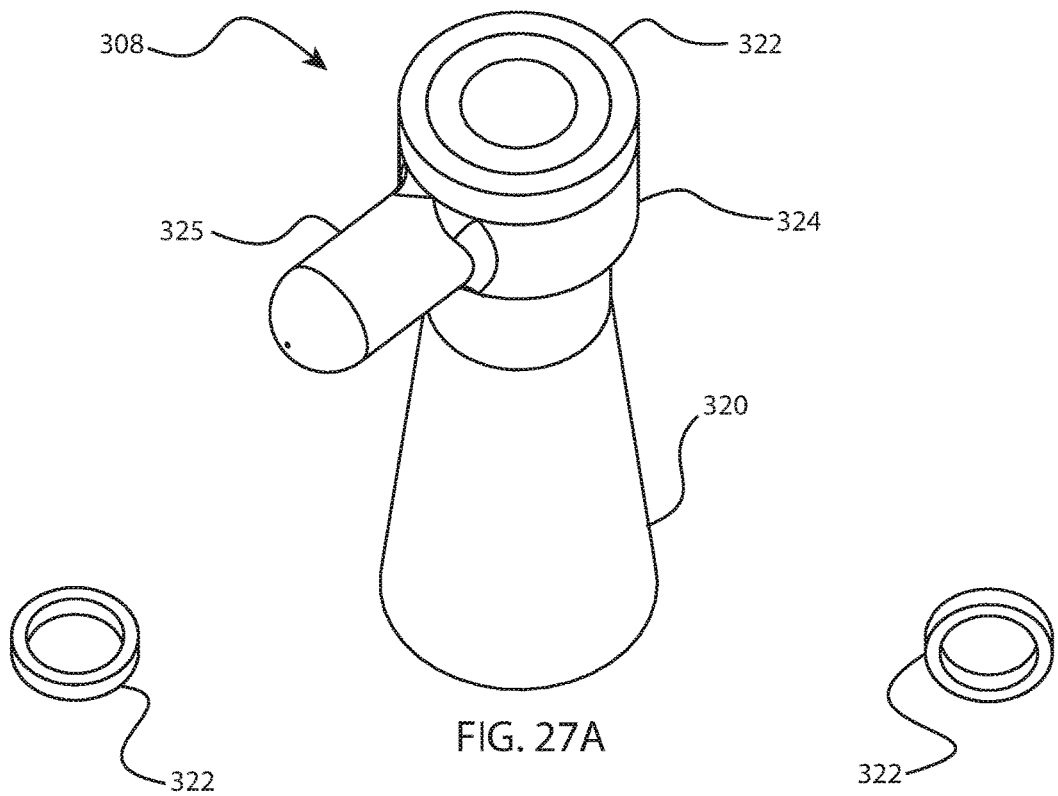
FIG. 27A is a perspective view of a tapered plug assembly of the instrument system of FIG. 21A.
Figure 27B:
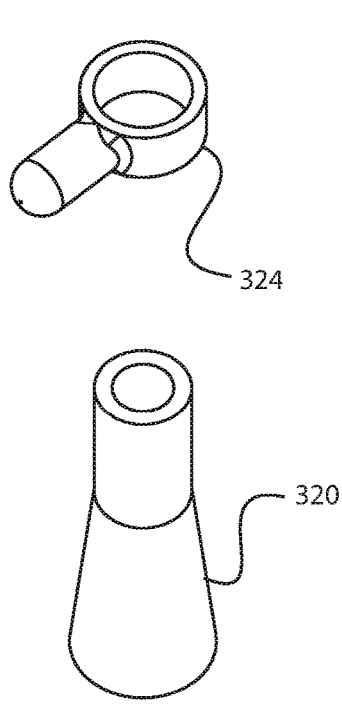
FIG. 27B is an exploded perspective view of the tapered plug assembly of FIG. 27A.
Figure 27C:
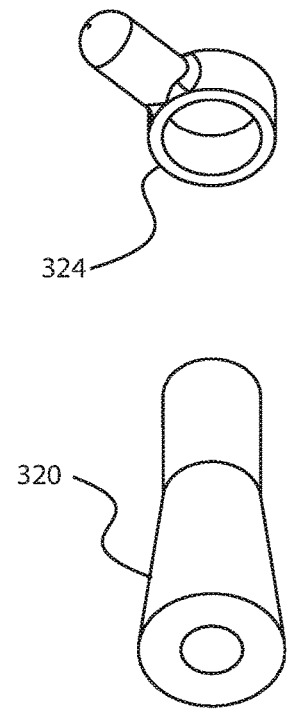
FIG. 27C is another exploded perspective view of the tapered plug assembly of FIG. 27A from a different direction.

Referring to FIGS. 27A-27C, the tapered plug assembly 308 may include a tapered plug 320, a cap 322, and a lock 324. The tapered plug assembly 308 may closely encircle the bone pin with minimal clearance, just enough clearance to permit the bone pin to be rotationally driven through the tapered plug assembly 308 while permitting little to no angular deviation of the bone pin. In an alternate embodiment, the tapered plug assembly 308 may move between a closed configuration and an open configuration. In the closed configuration, the tapered plug assembly 308 may fit closely around the bone pin. In the open configuration, the tapered plug assembly may fit loosely around the bone pin. The inside diameter through the tapered plug assembly 308 may be larger in the open configuration than in the closed configuration.

Referring to FIGS. 27A-28B, each tapered plug assembly 308 is received in a hole 374 of the tibial-femoral pin guide 310 so that the wide end of the tapered plug 320 is in the hole 374, the narrow end of the tapered plug 320 extends beside a boss 376 of the tibial-femoral pin guide 310, and an arm 325 of the lock 324 is adjacent to the boss 376. The hole 374 may have an internal taper corresponding to the external taper of the tapered plug 320. The tapered plug assembly 308 may be captive to the tibial-femoral pin guide 310 in service. When the arm 325 is over the boss 376 (FIGS. 21B, 22B) in a locked configuration, the tapered plug assembly 308 is held in tight engagement in the hole 374; when the arm 325 is rotated away from the boss 376 in an unlocked configuration, the tapered plug assembly 308 is free to drop down so as to fit more loosely in the hole 374. In the alternate embodiment, when the arm 325 is over the boss 376, the tapered plug assembly 308 is in the closed configuration; when the arm 325 is rotated away from the boss 376, the tapered plug assembly 308 is in the open configuration. The locked or closed configurations of the tapered plug assembly 308 provide precise, close-fitting holes while the bone pins are being driven, so that the pins are accurately positioned, mutually parallel to each other, and all perpendicular to the mechanical axis 202 of the leg. The unlocked or open configurations of the tapered plug assembly 308 provide a looser fit after the bone pins have been driven, so that the tibial-femoral pin guide 310 can be removed more easily. The unlocked configuration provides a looser fit between the hole 374 and the tapered plug 320, while the open configuration provides a looser fit between the tapered plug 320 and the bone pin.

Referring to FIGS. 28A-29B, the tibial riser 312 may be rigidly coupled to the tibial-femoral pin guide 310 by inserting boss 378 of the tibial-femoral pin guide 310 into notch 380 of the tibial riser 312 and inserting a fastener through holes 382, 384. Alternately, the tibial riser 312 may be permanently rigidly coupled to the tibial-femoral pin guide.

Referring to FIGS. 29A-30B, the tibial outer extension rod 314 may be permanently rigidly coupled to the tibial riser 312 by welding tabs 386 of the tibial outer extension rod 314 to a corresponding fitting 388 of the tibial riser 312. Any tibial extension rod may be coupled to the tibial riser 312 in the same way. Alternately, tibial outer extension rod 314 may be removably or hingedly coupled to the tibial riser 312.

Referring to FIGS. 30A-31B, the first tibial inner extension rod 316 may be telescopically coupled to the tibial outer extension rod 314 by inserting the first tibial inner extension rod 316 into a central longitudinal hole 390 of the tibial outer extension rod 314 and inserting a fastener through a slot 392 of the tibial outer extension rod 314 and into a hole 394 of the first tibial inner extension rod 316, so that the tibial inner extension rod 316 is slidable within, and captive to, the tibial outer extension rod 314. The fastener may be removable so that the first tibial inner extension rod 316 may be removed from the tibial outer extension rod 314.

Figure 23A:
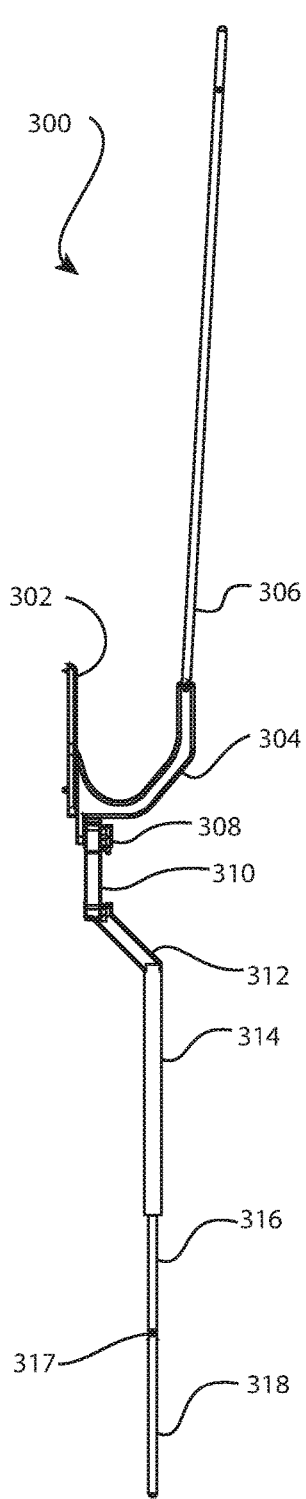
FIG. 23A is a side view of the instrument system of FIG. 21A.
Figure 23B:
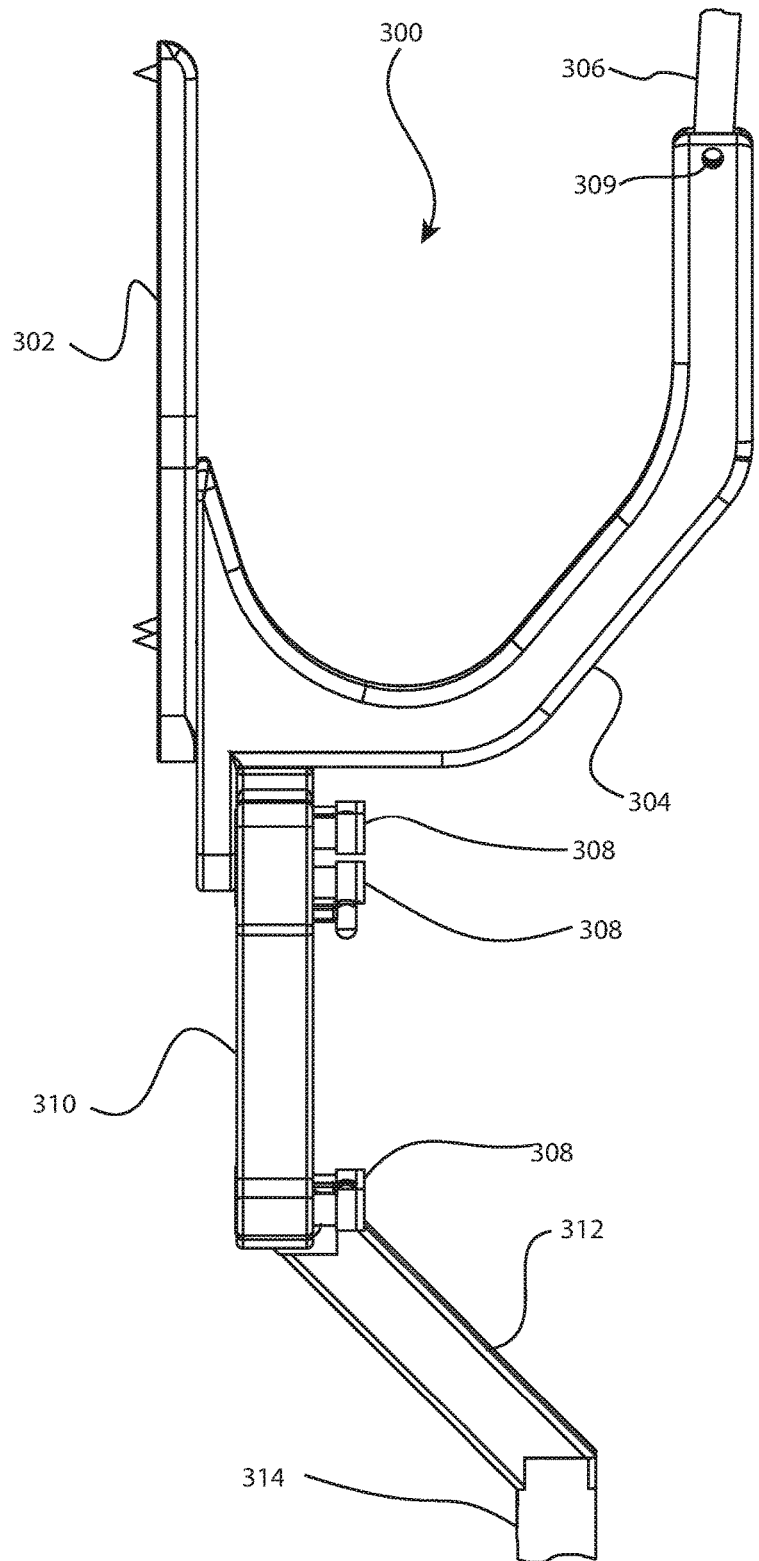
FIG. 23B is an enlarged detail view of a portion of the instrument system of FIG. 23A.
Figure 24A:
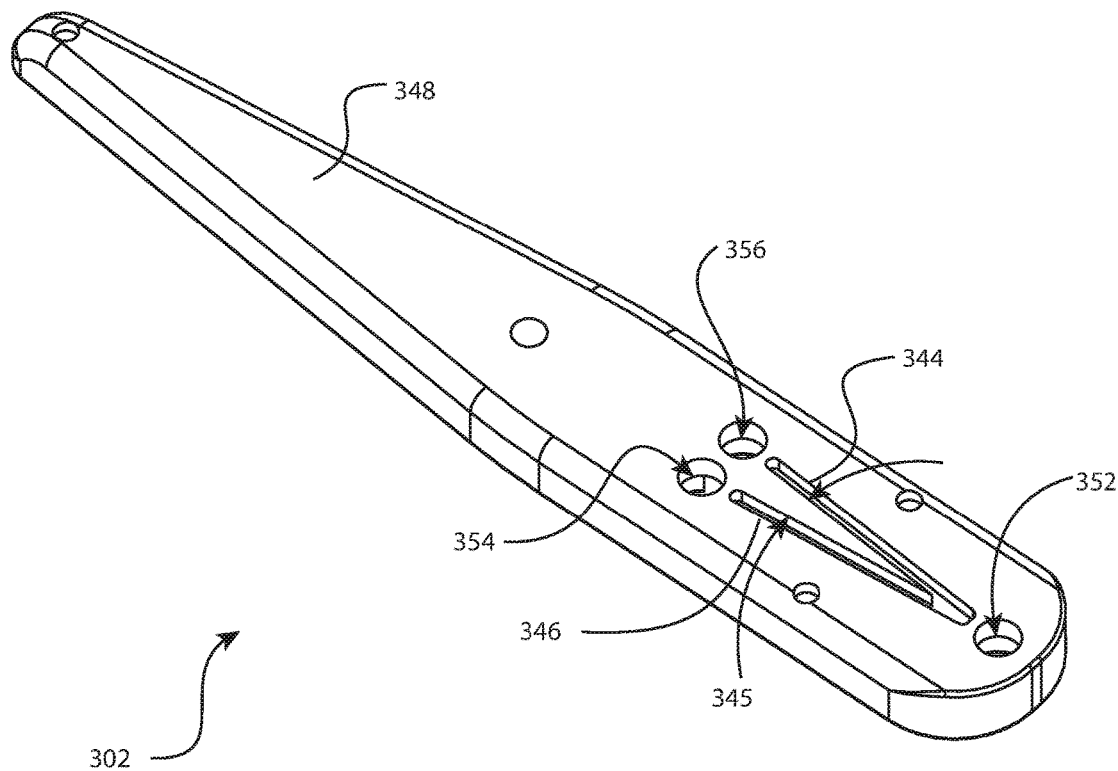
FIG. 24A is a perspective view of a base of the instrument system of FIG. 21A.
Figure 24B:
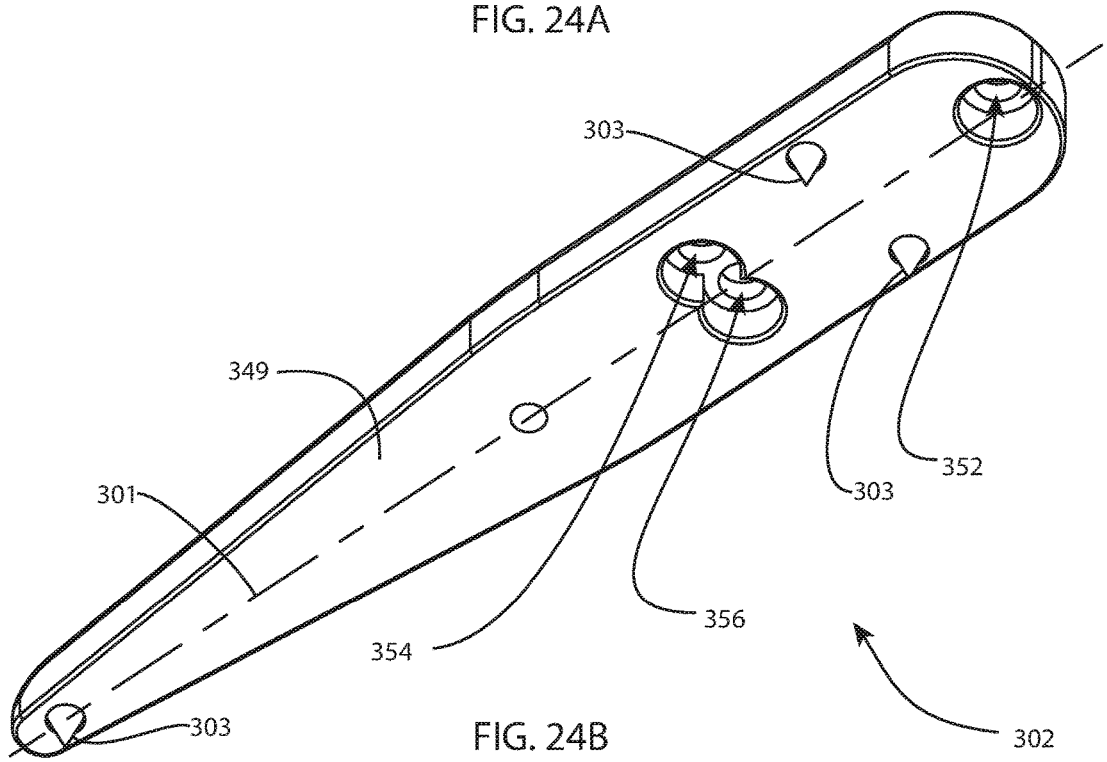
FIG. 24B is another perspective view of the base of FIG. 24A from a different direction.

Referring to FIGS. 31A-32B, second tibial inner extension rod 318 may be pivotally coupled to the first tibial inner extension rod 316 by inserting a fastener through holes 396, 398 to form a hinge 317 (FIGS. 21A and 23A). The second tibial inner extension rod 318 may remain coupled to the first tibial inner extension rod 316 in service. In use, the second tibial inner extension rod 318 is free to pivot about the hinge 317 to adjust to the patient's anatomy.

Prior to use, the base 302 and the femoral riser 304, with femoral extension rod 306, may be rigidly coupled together in an orientation appropriate to the surgical conditions, i.e., in a left orientation for a left knee, or in a particular angular orientation based upon pre-operative planning. Tapered plug assemblies 308 may be installed in the holes 374 of the tibial-femoral pin guide 310, and moved to the locked or closed configuration. The tibial riser 312, with tibial extension rod(s) 313, 314, 316, 318, may be rigidly coupled to the tibial-femoral pin guide 310. The tibial-femoral pin guide 310, with attached tibial riser 312 and tibial extension rod(s), may be rigidly coupled to the femoral riser 304.

Alternatively, the base 302, femoral riser 304, and femoral extension rod 306 may be coupled together as a femoral assembly, and the tibial-femoral pin guide 310, tapered plug assemblies 308 (locked or closed), tibial riser 312, and tibial extension rod(s) 313, 314, 316, 318 may be coupled together as a tibial assembly. Users may find that the femoral assembly is easier to manipulate without the tibial assembly attached, particularly when insinuating the base 302 between the suprapatellar fat pad 116 and the anterior distal femoral cortex. Users may prefer to couple the tibial assembly to the femoral assembly immediately before distracting the knee joint and aligning the tibia.

The base 302 may be inserted under the suprapatellar fat pad 116 and against the distal anterior femoral cortex in the manner described previously. The femoral riser 304 may rest against or within the trochlear groove. The femoral extension rod 306 may rest against the anterior aspect of the patient's thigh and hip. The proximal free end of the femoral extension rod 306 may be shifted medial-lateral until the femoral extension rod 306 passes over the center 120 of the femoral head 118. Proper alignment is achieved when the distal end of the femoral extension rod 306, base 302, and femoral riser 304 are centered in the medial/lateral width of the distal femur 102 while at the same time the proximal end of the femoral extension rod 306 passes over the femoral head center 120.

Shown later in this application, a target may be used in conjunction with the femoral extension rod 306 to precisely and objectively locate the center 120 of the femoral head 118. A target may be positioned over the anterior aspect of the patient's hip and/or over the center 120 of the femoral head 118 with fluoroscopic, radiographic, or C-arm imaging. Later, when the femoral extension rod 306 is positioned along the patient's thigh, the proximal free end of the rod 306 may be positioned relative to the target. The target may be a fork or "goal post," a ring, a reticle, "cross hairs," or the like, mounted to the free end of an adjustable arm whose base is stationary. In this application, a target may be "over the center of the femoral head" even if the target is actually superior or inferior to the femoral head, so long as the femoral extension rod passes over the center of the femoral head when the rod is aimed at the target. Alternatively, the proximal free end of the femoral extension rod 306 may be positioned relative to the anterior iliac crest.

Once the proximal free end of the femoral extension rod 306 is positioned over the center 120 of the femoral head 118, the base 302 may be pressed firmly against the distal anterior femoral cortex. An assistant may press down against the proximal portion of the femoral riser 304 with their palm. Optional spikes 303 (FIG. 24B) or other frictional elements may be included on the bone-facing side 349 of the base 302 to further stabilize the base against the bone. At this point, the base 302, the femoral riser 304, and the femoral extension rod 306 are aligned with the mechanical axis 202 of the leg (at least where it extends through the femur).

Certain ligaments may be at least partially released, or cut, at this stage or at another time in the procedure. For example, one or both of the cruciate ligaments may be cut at this stage in accordance with the design of the implants which will be used. One or both of the collateral ligaments may be released. At this stage, a provisional proximal tibial resection of about 3 mm to 5 mm to 6 mm (within surgical tolerances) may be made. The provisional proximal tibial resection increases the joint space so that a distractor, spreader, or other instrument may more easily fit between the distal femur and proximal (resected) tibia during a subsequent distraction step, and so that the knee joint (and lower limb) is more mobile during a subsequent lower limb positioning step. The provisional proximal tibial resection may also protect the posterior cruciate ligament (PCL) when a cruciate-retaining (CR) (or cruciate-sparing, CS) implant system is used.

The lower leg may now be distracted to the extent permitted by the existing ligamentous structures of the knee. A distractor, spreader, or other instrument may be used in the knee joint space to provide mechanical advantage. The distractor may indicate the applied distraction force. Alternatively, an assistant may manually distract the lower limb. As the distraction force is applied, the lower limb may be moved medial-lateral to align it with the distal free end of the tibial extension rod—in the example shown, the distal free end of extension rod 318. The alignment of the proximal free end of the femoral extension rod 306 may be monitored at this stage to ensure that it remains aligned over the center 120 of the femoral head 118 as the lower leg is brought into alignment with the distal free end of the tibial extension rod 318. The lower leg is properly aligned when the proximal end of the tibial extension rod 313 is centered in the medial/lateral width of the proximal tibia 106 and the distal free end of the tibial extension rod 318 is centered over the ankle and/or the second toe of the foot. This establishes the desired tibial varus/valgus rotation.

Once the knee joint is fully distracted, the proximal free end of the femoral extension rod 306 is positioned over the center 120 of the femoral head 118, the distal femur 102 and proximal tibia 106 are centered with respect to the femoral and tibial extension rods 306, 313, and the lower leg is aligned with the distal free end of the tibial extension rod 318, bone pins may be driven through the tapered plug assemblies 308 and the tibial-femoral pin guide 310. In the example shown, up to three pins may be driven into the distal femur 102, and up to two pins may be driven into the proximal tibia 106. All of the pins are parallel to each other and perpendicular to the mechanical axis 202 of the leg.

After the bone pins are driven, the tapered plug assemblies 308 may be moved to the unlocked or open configuration to provide a looser fit so that the tibial-femoral pin guide 310 can be removed more easily. The tibial-femoral pin guide 310 may be uncoupled from the femoral riser 304 and removed from the surgical site, along with the tapered plug assemblies 308, the tibial riser 312, and the tibial extension rods 313, 314, 316, 318. The base 302 may then be pulled distally out from under the suprapatellar fat pad 116, along with the femoral riser 304 and the femoral extension rod 306. Only the bone pins remain in the distal femur 102 and proximal tibia 106.

Referring to FIGS. 35-41B, a femoral base block assembly 330 may be included in the instrument system 300. The femoral base block assembly 330 may include a femoral base block 332, a translation bar 334, a knob 336, a top component 338, a bottom component 340, and a socket 342. The translation bar 334 includes two parallel shafts 335, 337 which slide within holes 339, 341, respectively, of the femoral base block 332.

The femoral base block 332 of the assembly 330 may be placed over the femoral bone pins after the rest of the components of system 300 have been removed and before any resections are made (other than the provisional tibial resection mentioned above). The femoral base block 332 may be oriented so that a tab 333 (FIG. 36B) contacts the distal anterior femoral cortex in or immediately adjacent to the former location of the distal portion of the base 302 (i.e., near the former location of hole 352). The tab 333 therefore contacts the distal anterior femoral cortex in the same plane as the base 302, providing direct referencing for a subsequent anterior femoral resection 214. A short shaft or rod (not shown) may be coupled in the socket 342 so that the short shaft extends posteriorly in the intercondylar notch (trochlear notch). The knee may be flexed to facilitate access and visualization of the intercondylar notch. The short shaft, socket 342, bottom component 340, top component 338, and knob 336 may be rotated about a post 400 of the translation bar 334 to align the short shaft with Whiteside's line. The short shaft may be locked in alignment with Whiteside's line, for example by tightening the knob 336, top component 338, bottom component 340, socket 342, or with a locking element (not shown). The femoral base block assembly 330 may then be removed from the femoral pins and the short shaft may be removed from the socket 342.

Figure 33A:
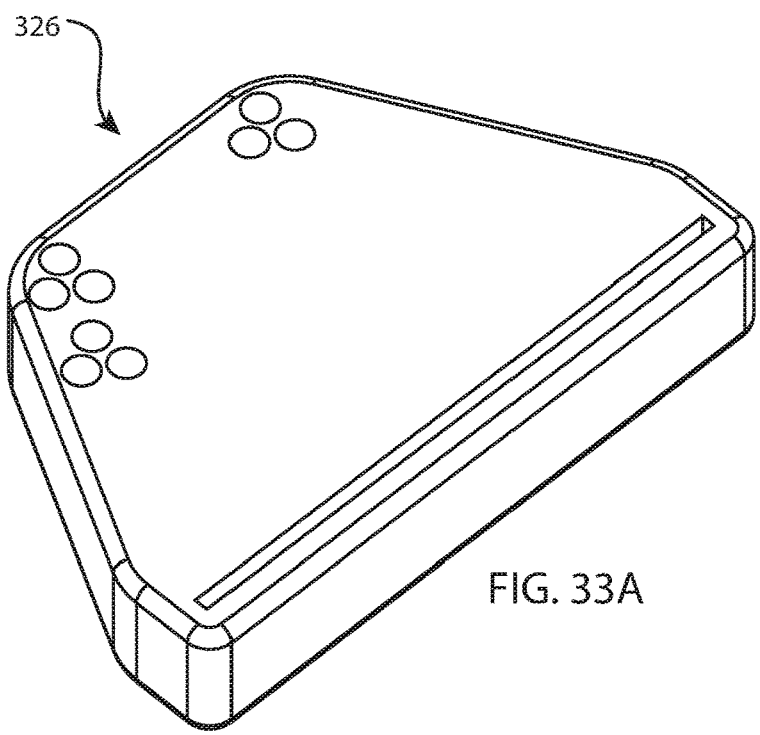
FIG. 33A is a perspective view of a femoral cut guide of the instrument system of FIG. 21A.
Figure 33B:
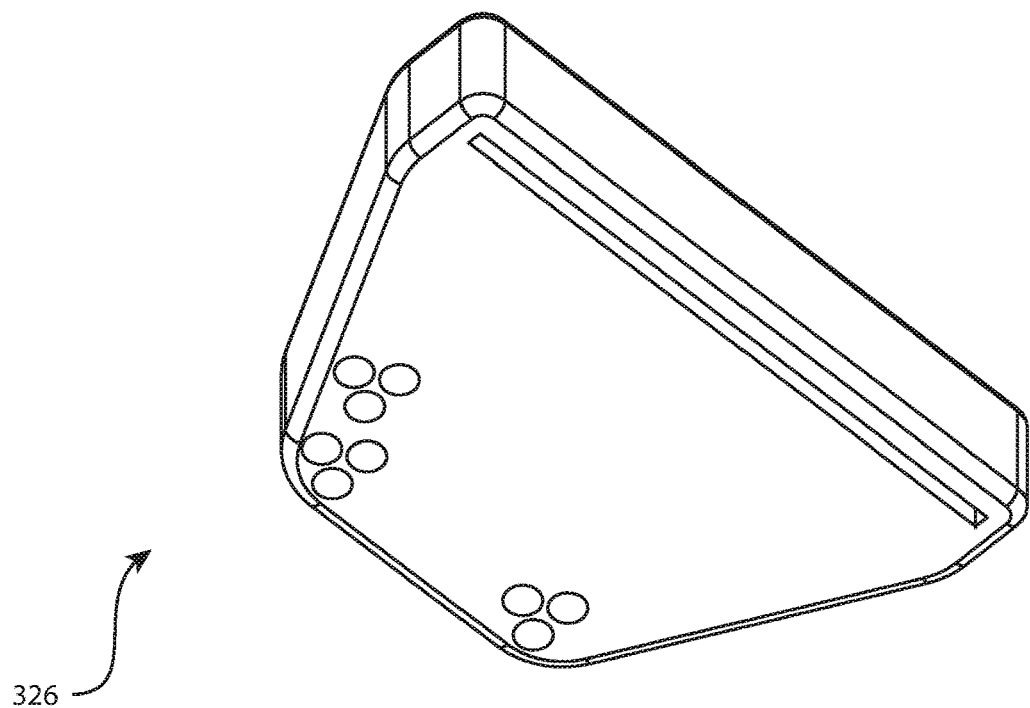
FIG. 33B is another perspective view of the femoral cut guide of FIG. 33A from a different direction.

Referring to FIGS. 33A-33B, a femoral cut guide 326 may be included in the instrument system 300. The femoral cut guide 326 may be placed over the femoral pins, and a saw used through the femoral cut guide to make a distal femoral resection 206.

The femoral base block 332 of the assembly 330 may be replaced over the femoral pins, and a femoral cutting block or four-in-one cut guide 750 (FIGS. 61A and 61B) may be coupled to the socket 342 so that the four-in-one cut guide rests against the distal femur in proper alignment with Whiteside's line due to the pre-set rotational position of the knob 336, top component 338, bottom component 340, and socket 342. The four-in-one cut guide 750 may guide multiple femoral cuts, such as the anterior femoral resection 214, the anterior femoral chamfer cut 216, the posterior femoral resection 220, and the posterior femoral chamfer cut 218. The anterior femoral resection 214 may be precisely aligned with the distal anterior femoral cortex as a result of the base 302 directly referencing the distal anterior femoral cortex and the femoral base block assembly 330 suspending the four-in-one cut guide 750 with its anterior resection slot 756 at the same level. The tab 333 of the femoral base block 332 contacts the distal anterior femoral cortex as did the base 302 to provide accurate positioning of the anterior resection slot of the femoral cutting block coupled to the femoral base block assembly 330.

Figure 34A:
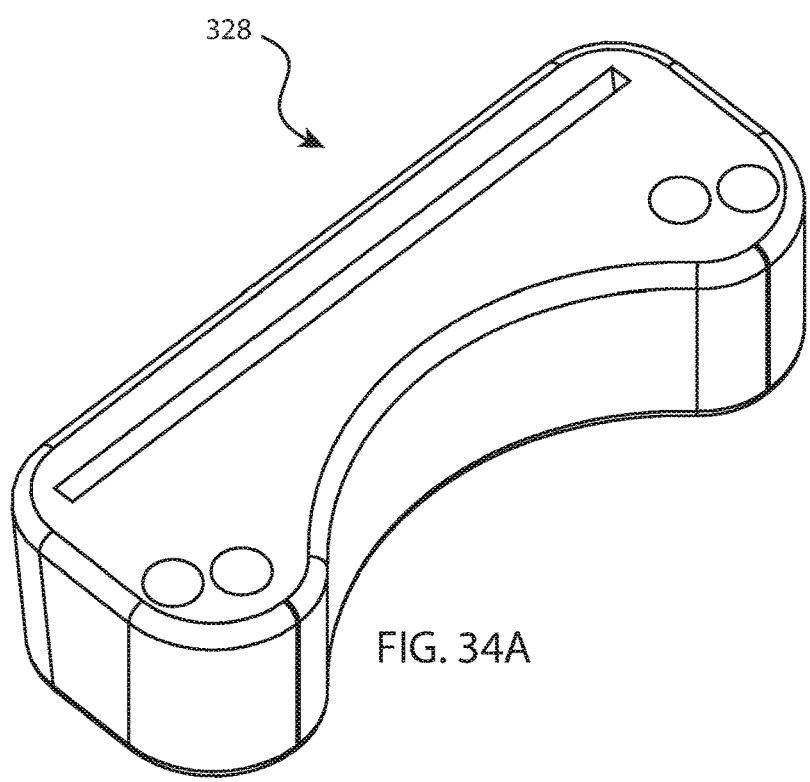
FIG. 34A is a perspective view of a tibial cut guide of the instrument system of FIG. 21A.
Figure 34B:
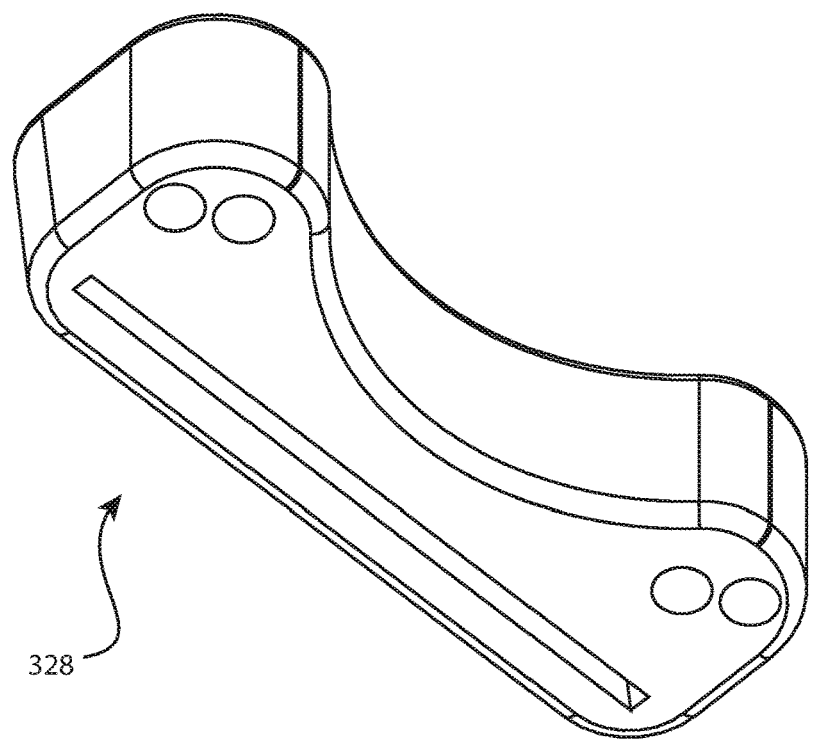
FIG. 34B is another perspective view of the tibial cut guide of FIG. 34A from a different direction.

Referring to FIGS. 34A-34B, a tibial cut guide 328 may be included in the instrument system 300. The tibial cut guide 328 may be placed over the tibial pins, and a saw used through the tibial cut guide to make a proximal tibial resection 210. The proximal tibial resection 210 may be made at the same time as, or immediately after, the distal femoral resection 206; it may also be made after all femoral resections are complete. The tibial cut guide 328 may be designed to produce a tibial resection 210 that is perpendicular to the mechanical axis 202 of the leg, which may be referred to as a zero degree resection. The tibial cut guide 328 may be designed to produce a tibial resection 210 that forms an angle other than 90 degrees with the mechanical axis. For example, the tibial cut guide 328 may produce a tibial resection 210 that slopes posteriorly and inferiorly. A sloping tibial resection 210 may be referred to by its angle relative to a perpendicular resection. For example, a six degree tibial resection slopes from anterior-superior to posterior-inferior, making a six degree angle with a theoretical perpendicular resection. Multiple posterior resection angles are contemplated herein, for example, zero degrees and six degrees.

Figure 35:
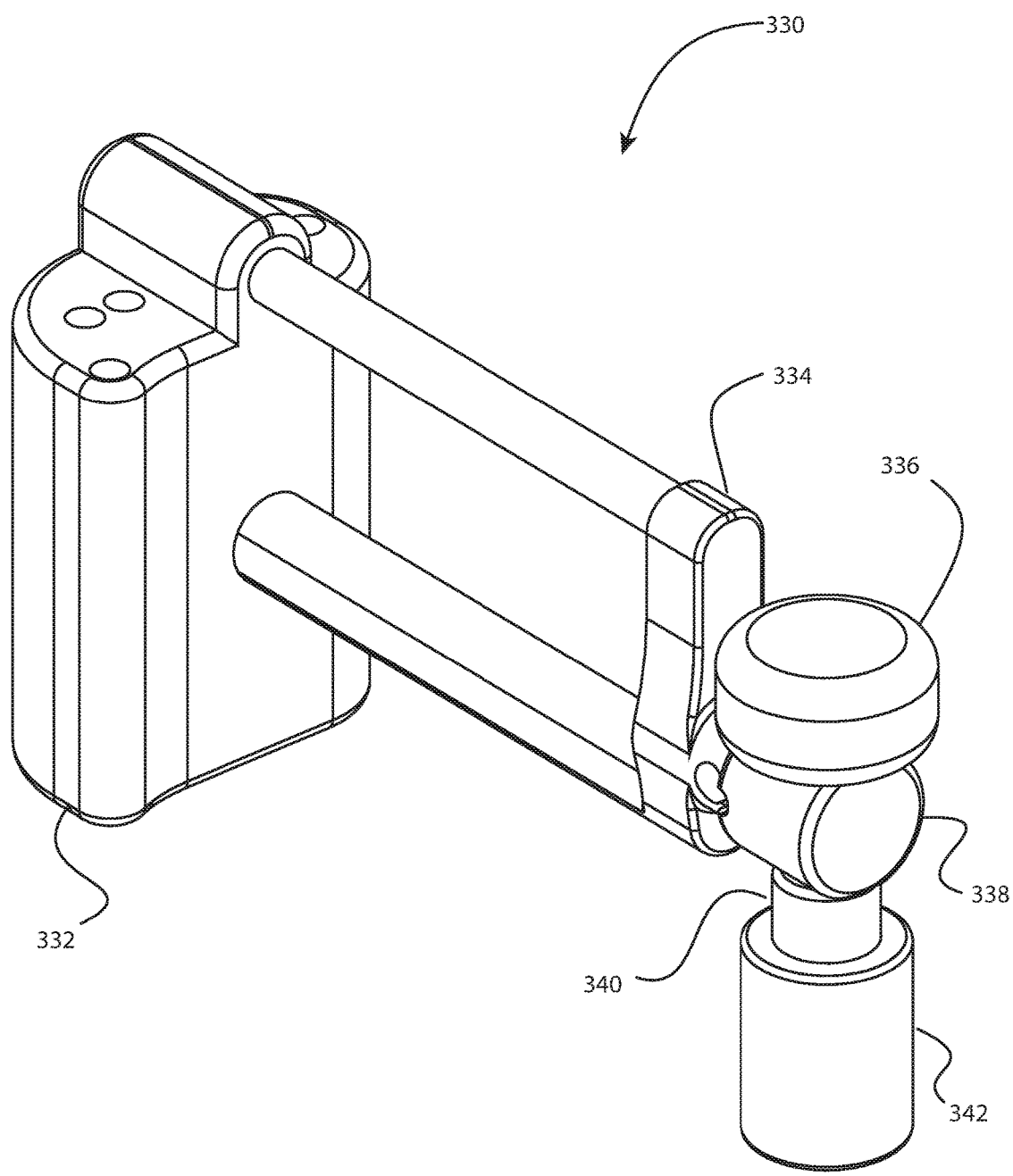
FIG. 35 is a perspective view of a femoral base block assembly.
Figures 36A, 36B:
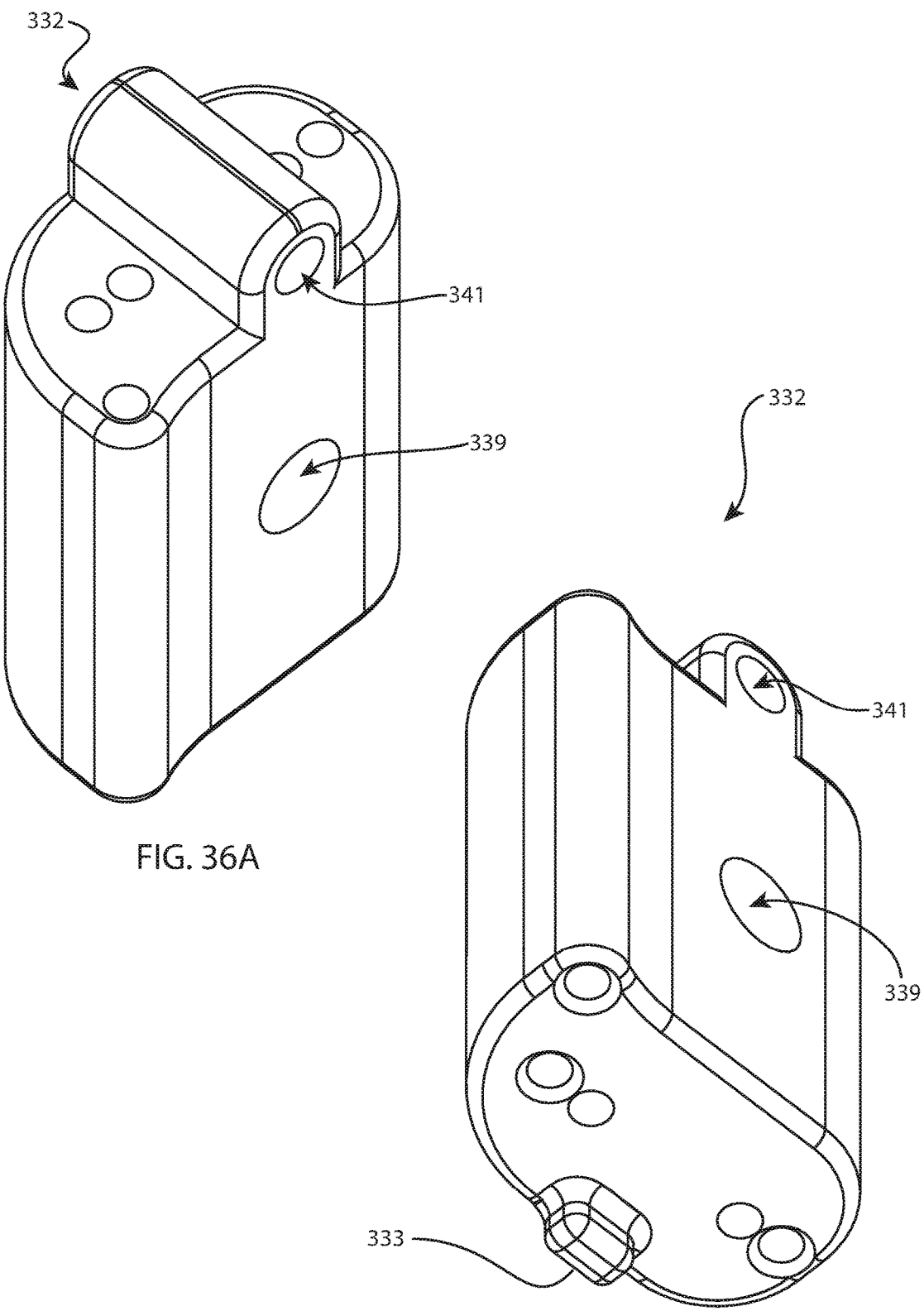
FIG. 36A is a perspective view of a femoral base block of the femoral base block assembly of FIG. 35.
FIG. 36B is another perspective view of the femoral base block of FIG. 36A from a different direction.
Figure 37:
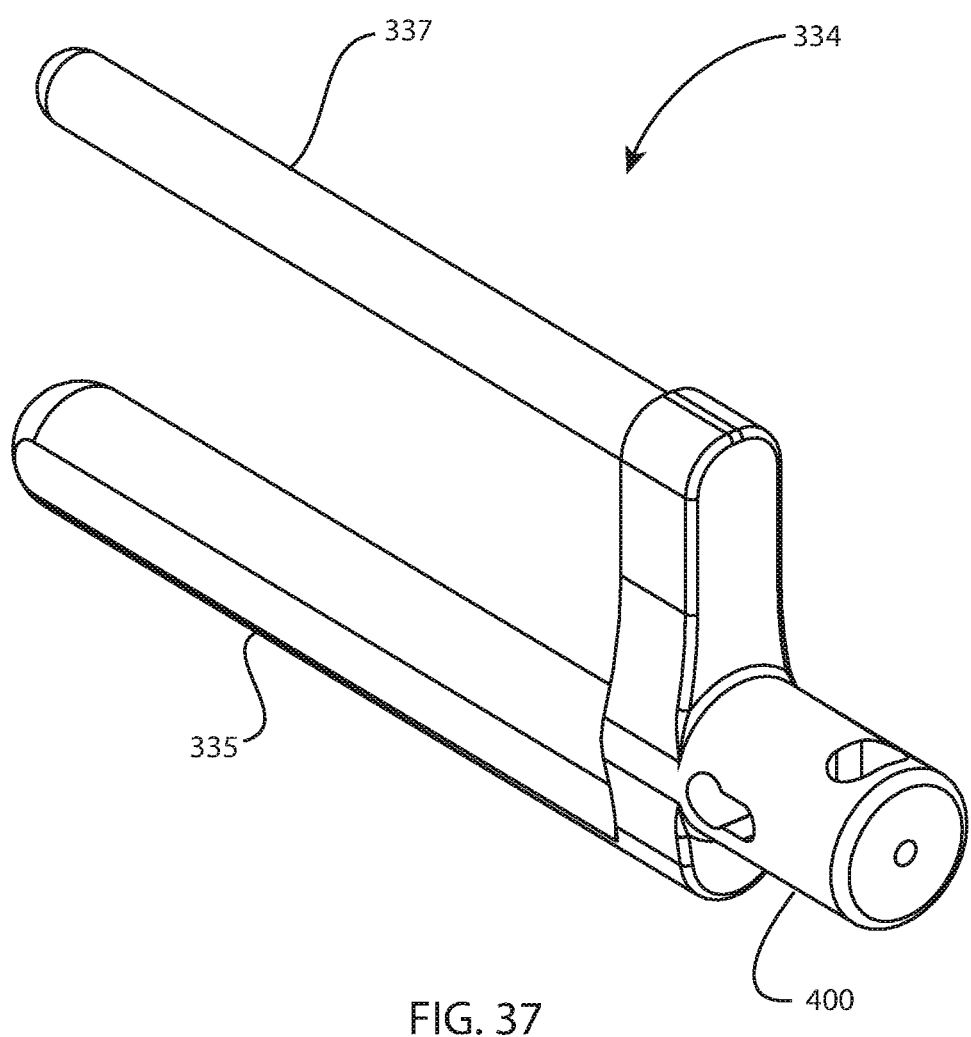
FIG. 37 is a perspective view of a translation bar of the femoral base block assembly of FIG. 35.
Figure 38A:
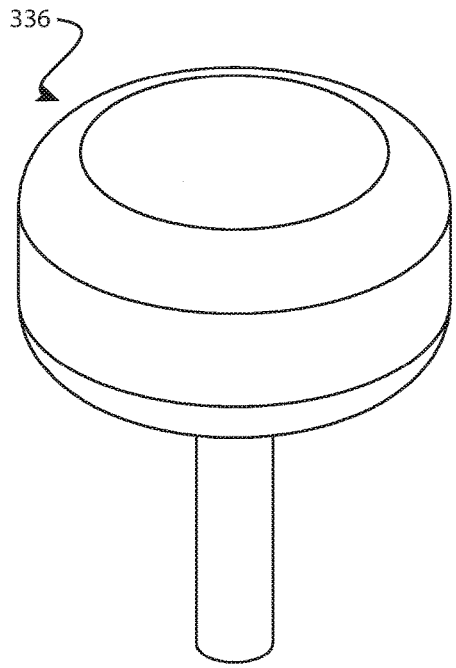
FIG. 38A is a perspective view of a knob of the femoral base block assembly of FIG. 35.
Figure 38B:
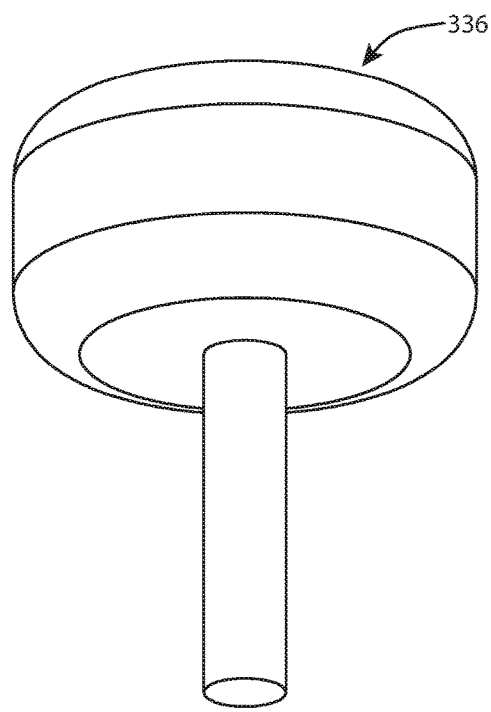
FIG. 38B is another perspective view of the knob of FIG. 38A from a different direction.
Figure 39A:
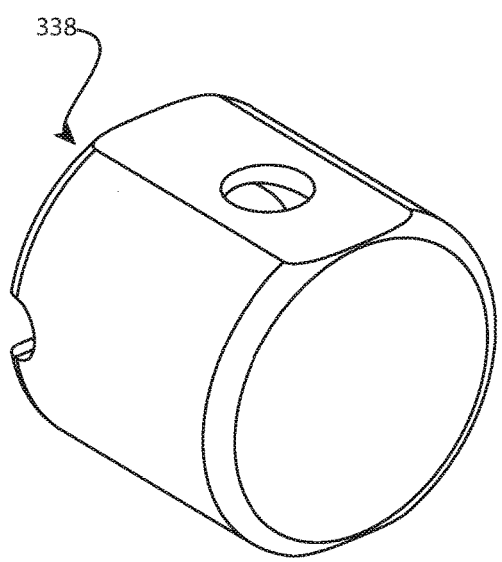
FIG. 39A is a perspective view of a top component of the femoral base block assembly of FIG. 35.
Figure 39B:
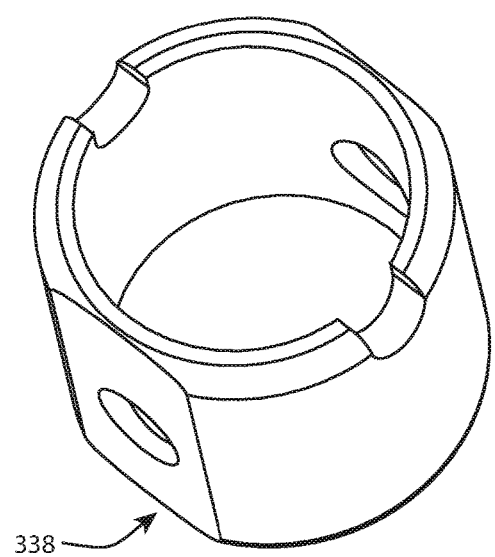
FIG. 39B is another perspective view of the top component of FIG. 39A from a different direction.
Figure 40A:
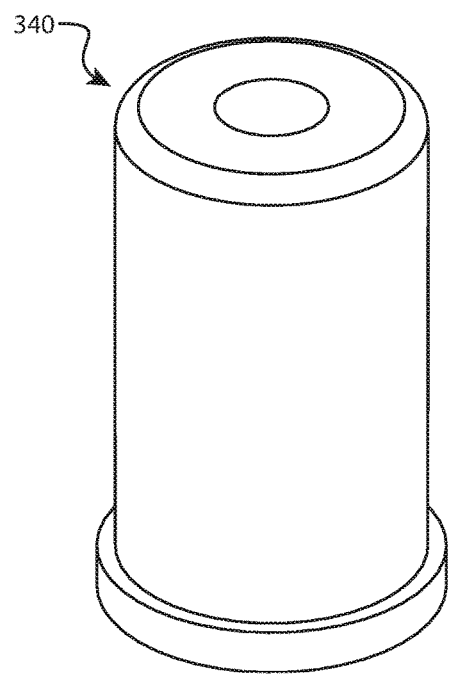
FIG. 40A is a perspective view of a bottom component of the femoral base block assembly of FIG. 35.
Figure 40B:
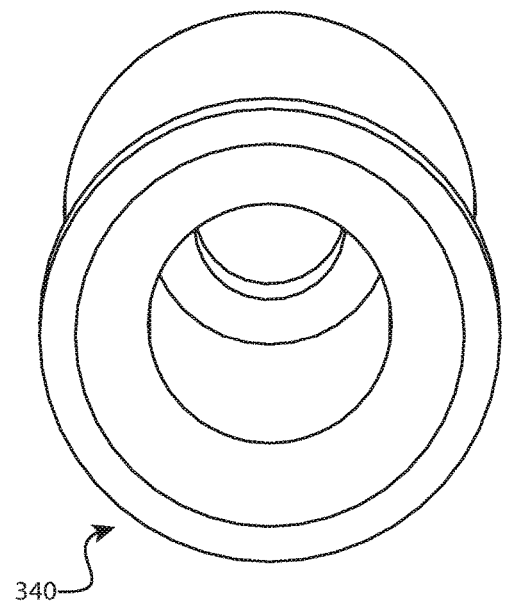
FIG. 40B is another perspective view of the bottom component of FIG. 40A from a different direction.
Figure 41A:
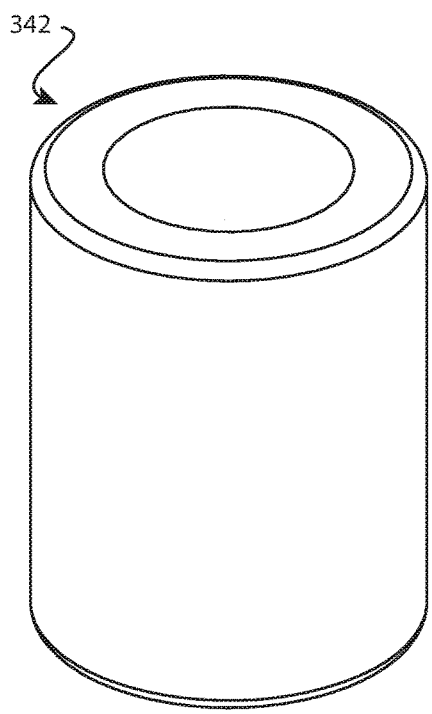
FIG. 41A is a perspective view of a socket of the femoral base block assembly of FIG. 35.
Figure 41B:
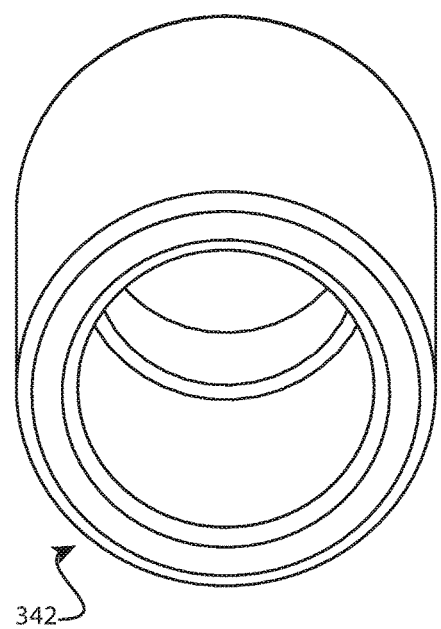
FIG. 41B is another perspective view of the socket of FIG. 41A from a different direction.
Figure 42A:
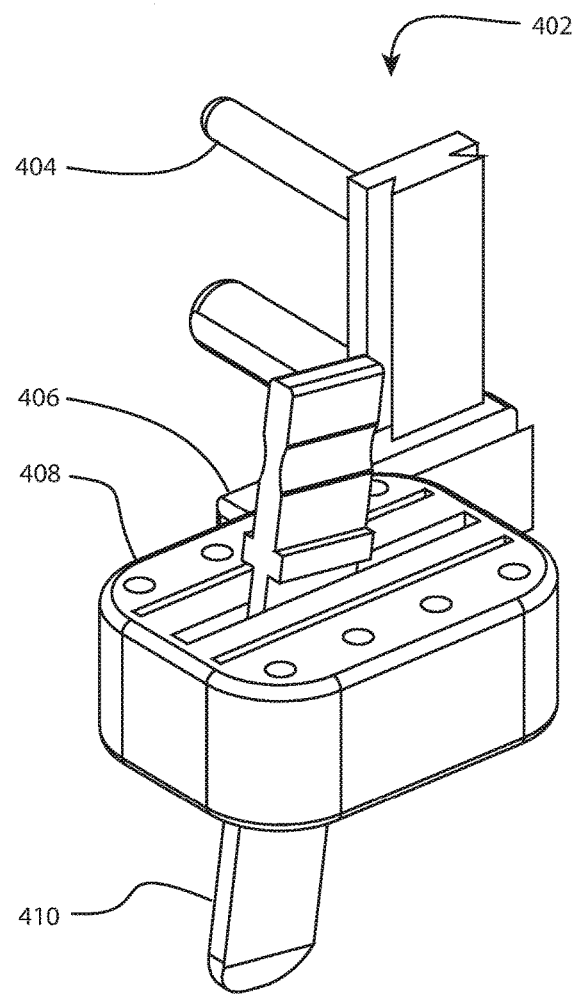
FIG. 42A is a perspective view of another translation bar, a slide, a cut guide, and a condyle probe, all for substitution into the femoral base block assembly of FIG. 35.
Figure 42B:
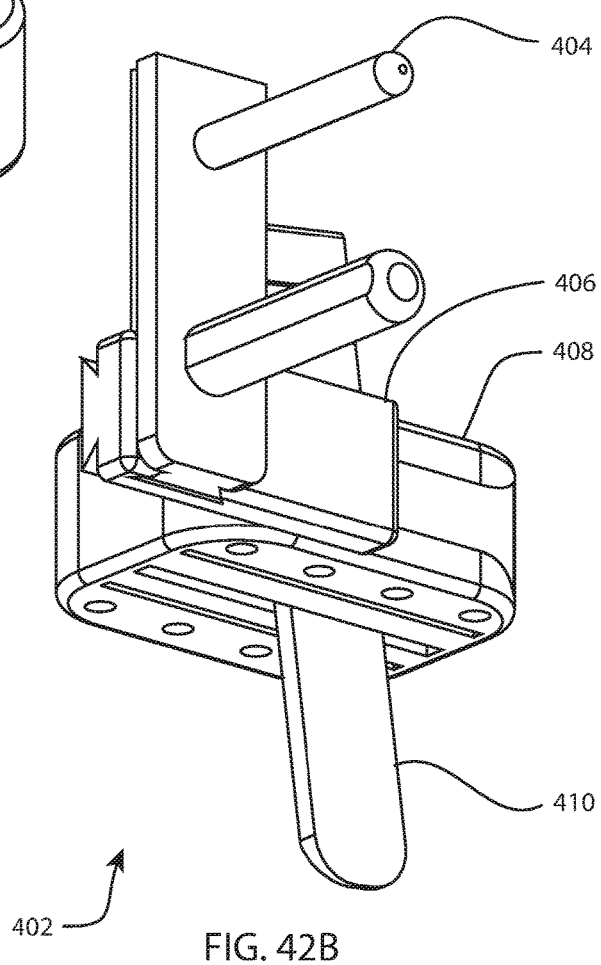
FIG. 42B is another perspective view of the translation bar, slide, cut guide, and condyle probe of FIG. 42A from a different direction.
Figure 43A:
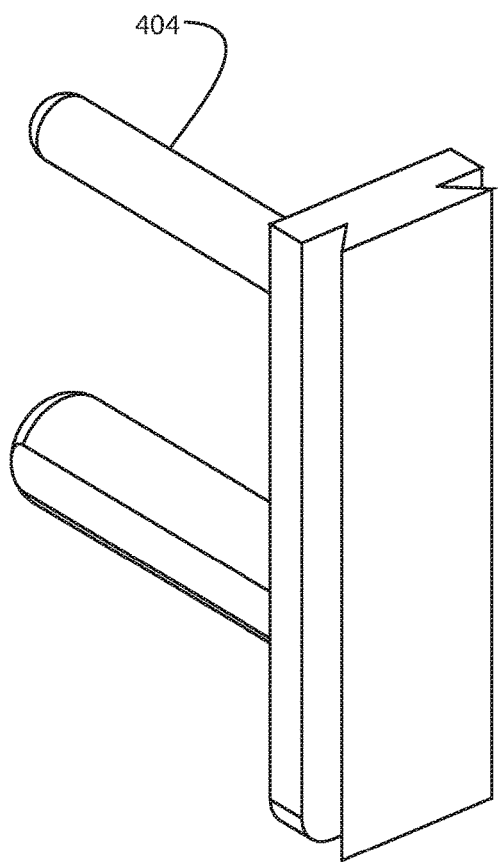
FIG. 43A is a perspective view of the translation bar of FIG. 42A.
Figure 43B:
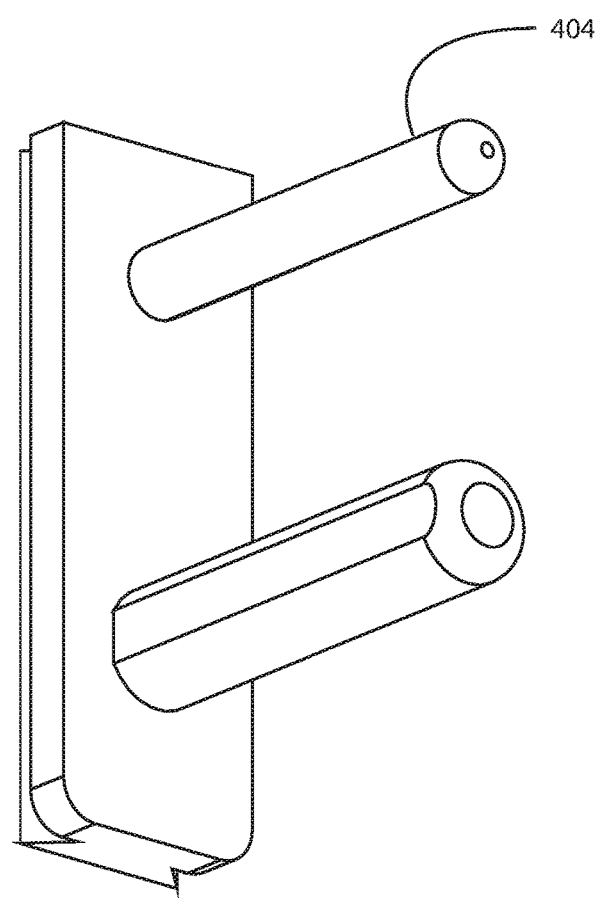
FIG. 43B is another perspective view of the translation bar of FIG. 43A from a different direction.
Figure 44A:
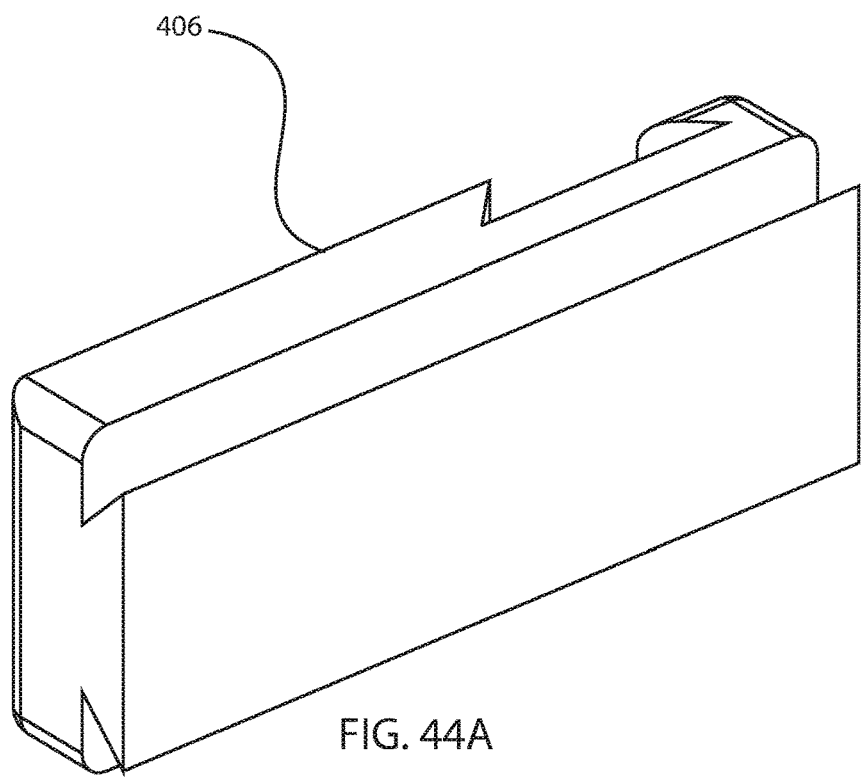
FIG. 44A is a perspective view of the slide of FIG. 42A.
Figure 44B:
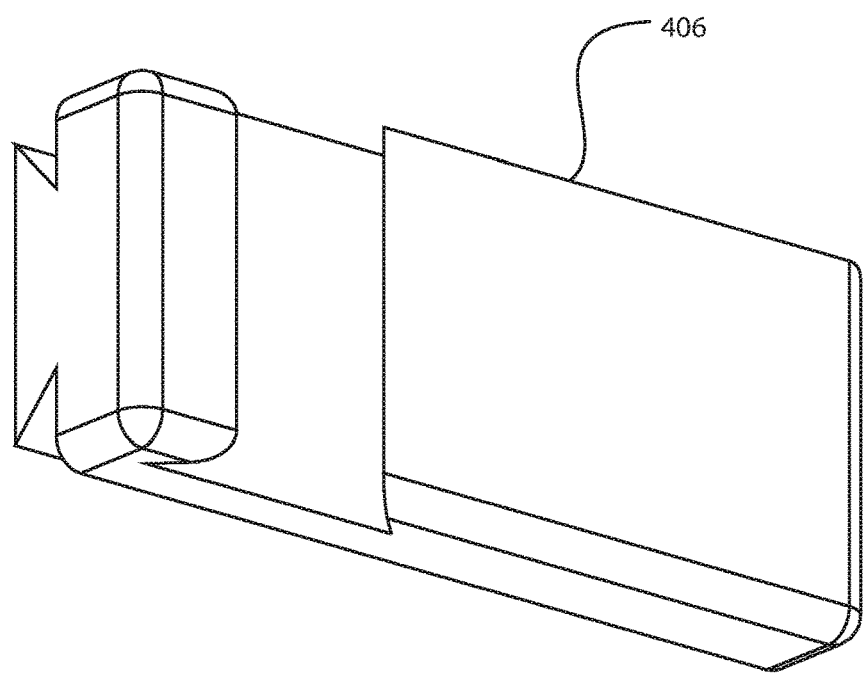
FIG. 44B is another perspective view of the slide of FIG. 44A from a different direction.
Figure 45A:
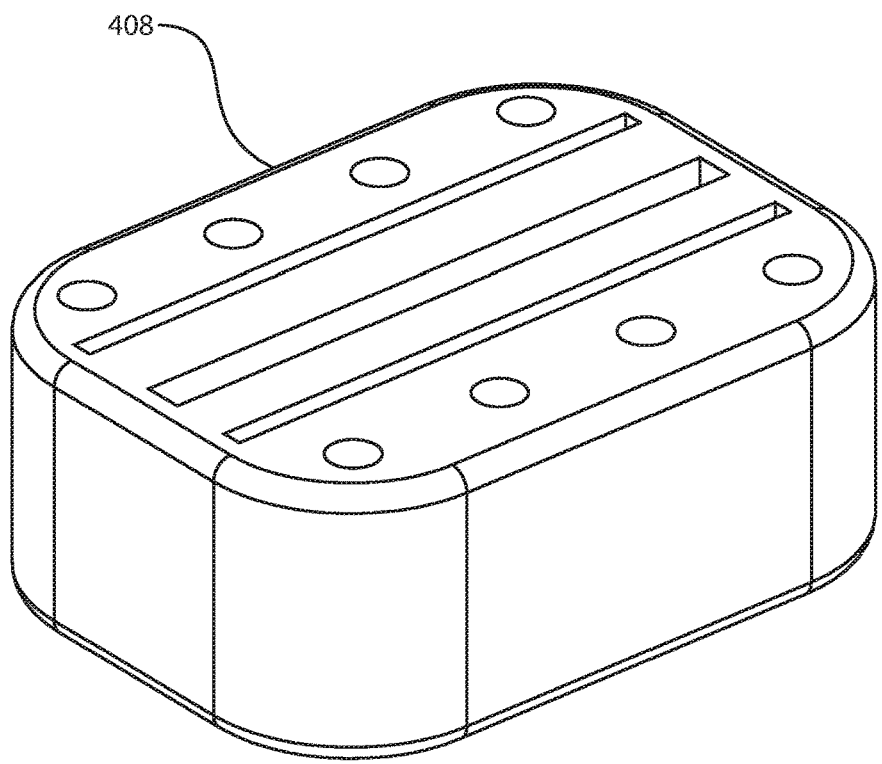
FIG. 45A is a perspective view of the cut guide of FIG. 42A.
Figure 45B:
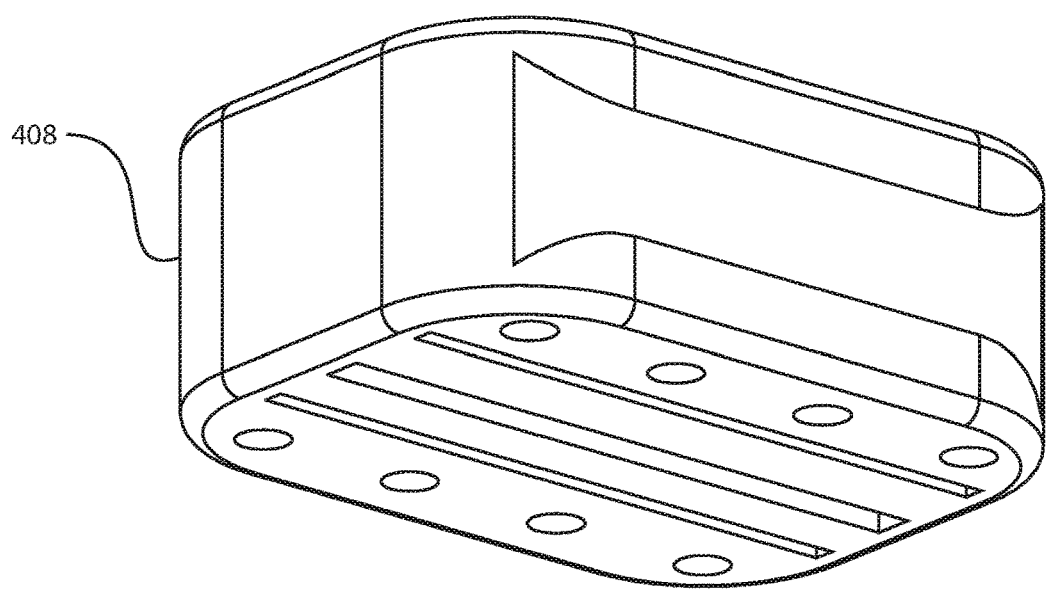
FIG. 45B is another perspective view of the cut guide of FIG. 45A from a different direction.
Figure 46:
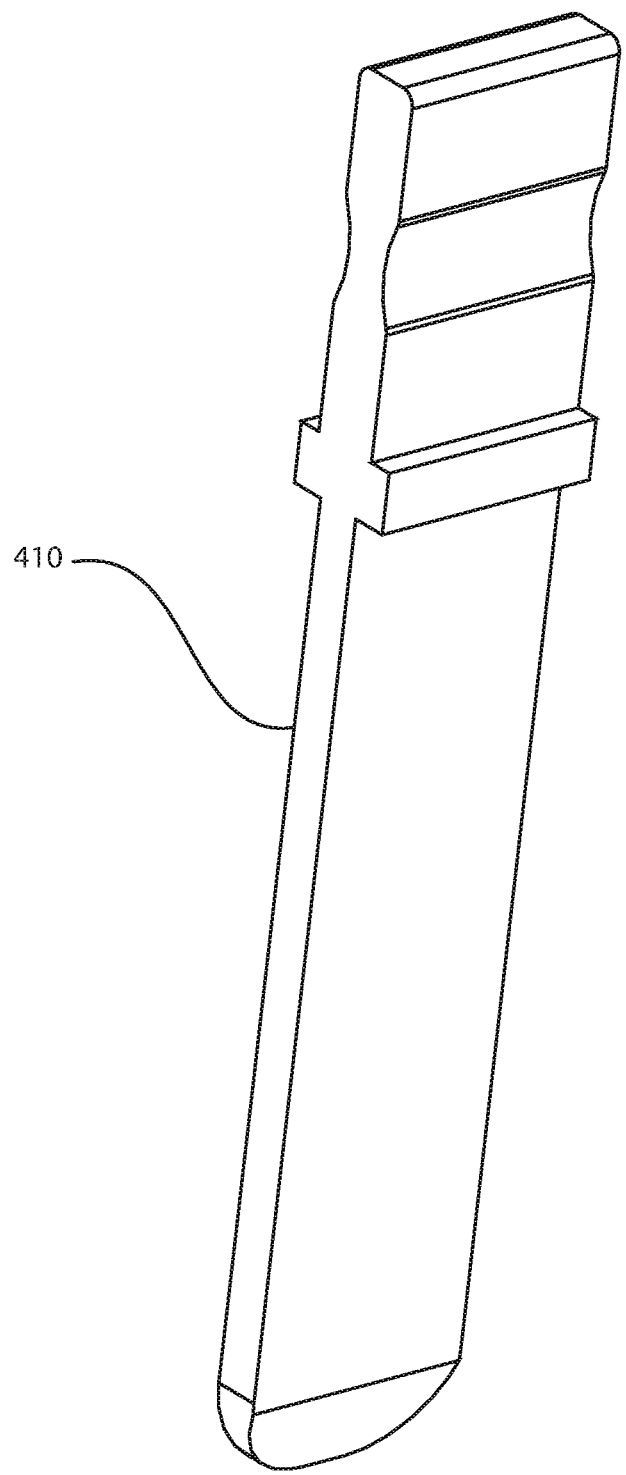
FIG. 46 is a perspective view of the condyle probe of FIG. 42A.

Referring to FIGS. 42A-46, another translation bar 404, a slide 406, a cut guide 408, and a condyle probe 410 may all be substituted into the femoral base block assembly 330 of FIG. 35 instead of the translation bar 334, knob 336, top component 338, bottom component 340, and socket 342. The translation bar 404, slide 406, cut guide 408, and condyle probe 410 may be referred to collectively as an alternate translation/cut guide assembly 402. The alternate translation/cut guide assembly 402 may be applicable to bicompartmental or bicondylar knee arthroplasty, or uni-compartmental or unicondylar knee arthroplasty. The alternate translation/cut guide assembly 402 may be particularly applicable to unicompartmental or unicondylar knee arthroplasty due to the X-Y translation provided by the double dovetail slide design, which provides anterior-posterior and medial-lateral sliding adjustment in addition to the superior-inferior sliding adjustment provided by the translation bar 404. The cut guide 408 includes slots for distal femoral and proximal tibial cuts. The condyle probe 410 may be used to center the cut guide 408 across the joint space.

Referring to FIGS. 47A-49B, yet another instrument system 500 is shown. This instrument system is designed to be used while the knee joint is in full extension and maximally distracted, while referencing the distal anterior femoral cortex, and while the leg is properly aligned with the mechanical axis 202 of the leg. The femoral head center 120, distal femur 102, proximal tibia 106, and ankle/second toe/anterior tibial crest or spine are all simultaneously aligned with the mechanical axis 202. The system 500 includes apparatus for referencing Whiteside's line while the distal femoral condyles are intact, before any femoral resection occurs, and locking this reference into the apparatus to guide later surgical steps.

The instrument system 500 is illustrated with a combination of components that is similar to those depicted in FIGS. 21A and 21B for instrument system 300. The instrument system 500 may include a base 502, a femoral riser 504 (also known as a handle), a femoral extension rod 506, a tibial connection block 508, and a tibial pin guide 510. The instrument system 500 may also include a tibial riser 509 like tibial riser 312, and a tibial extension rod 511 like tibial extension rod 313, alignment rod 156, femoral extension rod 306, or femoral extension rod 506. The illustrated tibial extension rod 511 is identical to the femoral extension rod 506. The instrument system 500 may also include additional components as described below for FIGS. 47A-68B. At least the femoral riser 504, tibial connection block 508, tibial pin guide 510, and, if present, tibial riser 509 may be disposable components molded from polymer materials.

Figures 50A, 50B:
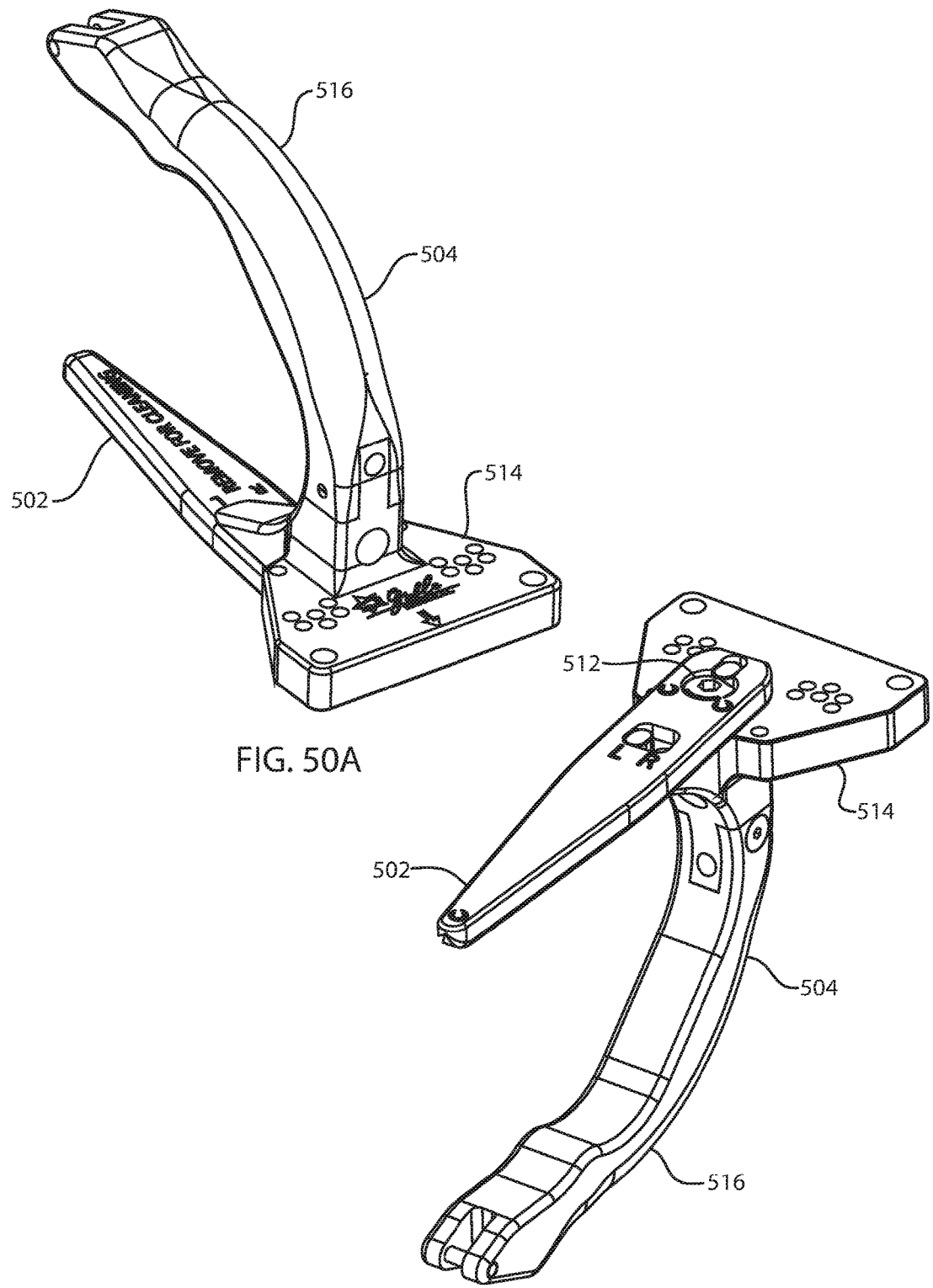
FIG. 50A is a perspective view of a base and a femoral riser assembly of the instrument system of FIG. 47A.
FIG. 50B is another perspective view of the base and femoral riser assembly of FIG. 50A from a different direction.

Referring to FIGS. 50A and 50B, the femoral riser 504 is shown coupled to the base 502. A cam 512 is visible coupled to the base 502 in FIG. 50B. The femoral riser 504 may include a femoral pin guide 514 and a handle 516. The femoral pin guide 514 and handle 516 may be rigidly coupled together in a releasable or permanent manner. The femoral pin guide 514 and handle 516 may be fabricated as a unitary part. The coupled femoral riser 504 and base 502 may be analogous to the coupled femoral riser 304, base 302, and a portion of the tibial-femoral pin guide 310.

Referring to FIGS. 51A and 51B, the base 502 is an elongated plate with a bone contacting surface 518 and an opposite top surface 520. The base 502 has a distal portion 522 and a proximal portion 524 which tapers to a proximal tip which is narrower than the distal portion. A longitudinal axis 503 extends along the length of the base 502 between the distal and proximal portions 522, 524; only a portion of the axis 503 is shown in FIG. 51B for clarity. The base 502 includes a hole 526 through the distal portion 522. A pocket 528 is recessed into the bone contacting surface 518 around the hole 526. The pocket 528 may be described as a counterbore around the hole 526. The base 302 includes three oblong holes 530, 532, 534 recessed into the top surface 520. Each hole 530, 532, 534 includes a shelf 536 on at least one side wall. The shelves 536 are illustrated on the distal side walls of the holes 530, 532, 534 but may be on the proximal side walls or elsewhere instead. The base 502 may include one or more frictional elements, such as spikes 538 protruding from the bone contacting surface 518.

Referring to FIGS. 51C and 51D, the cam 512 includes a body 540 and a spindle 542 that protrudes from the body. The body 540 has a non-circular cross-sectional profile around the spindle 542 so that as the cam 512 turns about the spindle, the body can exert (or release) a side force against another object. Thus the body 540 has a locking portion 546 and an unlocking portion 548 which may be generally opposite the locking portion, or at least circumferentially spaced apart from the locking portion. The locking portion 546 extends radially farther from the spindle 542 than the unlocking portion 548 does. The body 540 may include a resilient portion 550, which may be between the locking portion 546 and the unlocking portion 548, or may be associated with the locking portion 546 as illustrated. The resilient portion 550 is characterized by a slot 552 which enables the resilient portion to flex under load. The spindle 542 is cylindrical and is narrower than the body 540. A torque socket 544 is recessed into the body 540 opposite the spindle 542, and concentric with the spindle. The torque socket 544 is illustrated as a hex socket, although a square, cruciate, hexalobular, or other non-circular shape could be substituted.

The cam 512 is coupled to the base 502 by inserting the spindle 542 into the hole 526 and inserting the body 540 into the pocket 528. The cam 512 may be captive to the base 502, at least during use. The cam 512 may be removable from the base 502.

Figure 52A:
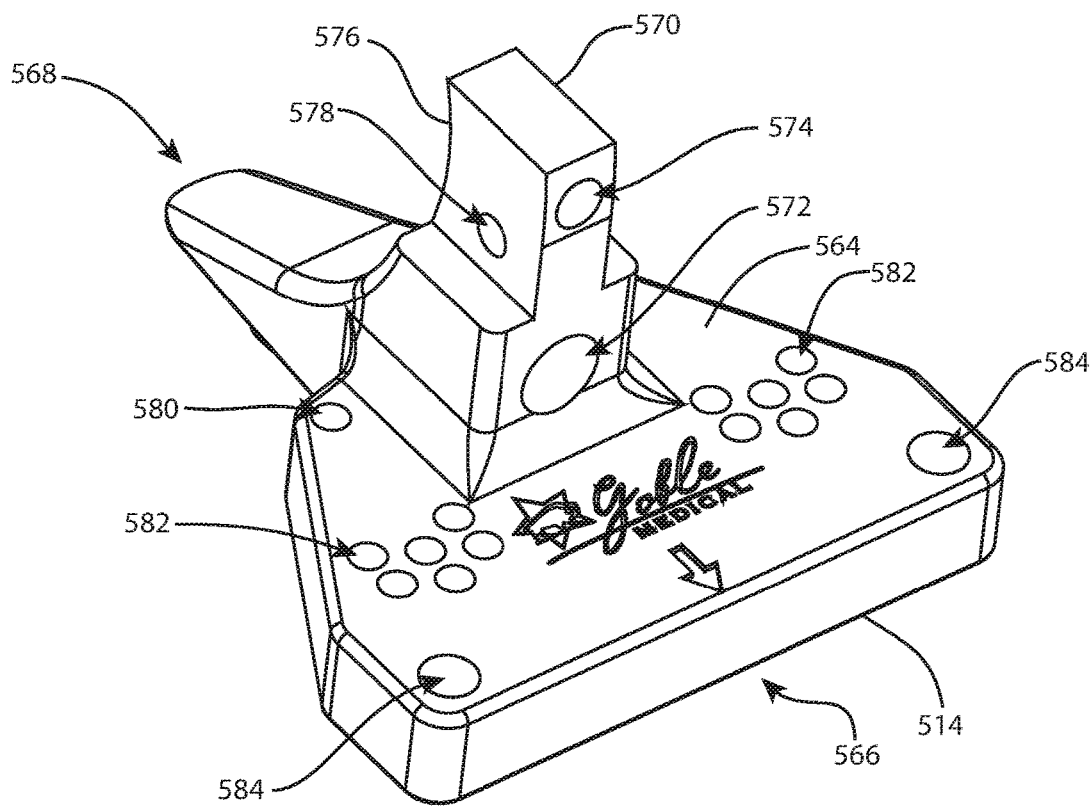
FIG. 52A is a perspective view of a femoral pin guide of the femoral riser assembly of FIG. 50A.
Figure 52B:
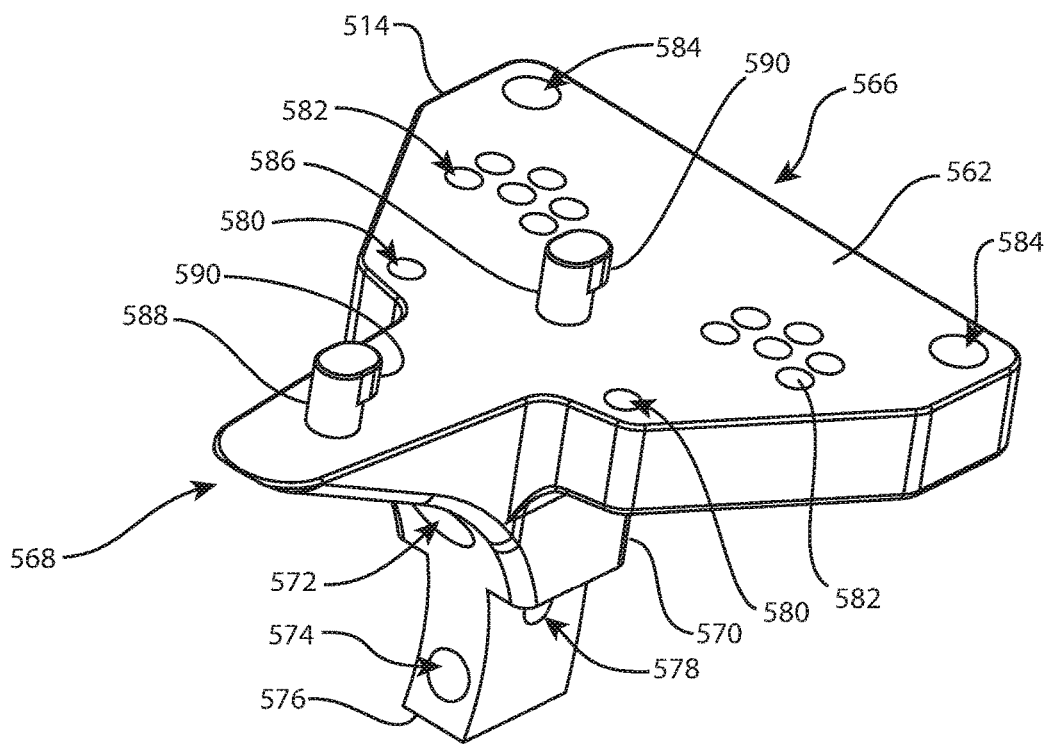
FIG. 52B is another perspective view of the femoral pin guide of FIG. 52A from a different direction.

Referring to FIGS. 52A and 52B, the femoral pin guide 514 is a roughly triangular plate with a bone facing surface 562 and an opposite top surface 564. The femoral pin guide 514 has a distal portion 566 and a proximal portion 568 which tapers to a proximal tip which is narrower than the distal portion. A stalk 570 protrudes from the top surface 564. A first hole 572 extends through the stalk 570 in a proximal-distal direction and a second, smaller diameter, hole 574 extends through the stalk parallel to the first hole 572 and farther from the top surface 564. The stalk 570 terminates in a narrow tab 576 which has a hole 578 that is transverse to the holes 572, 574. The femoral pin guide 514 is illustrated with several holes 580, 582 which receive bone pins. Two proximal holes 580 are shown and twelve distal holes 582 are shown, although any number of holes may be provided. The left and right holes 580 converge together as they approach the bone facing surface 562. The left group and the right group of holes 582 also converge together as they approach the bone facing surface 562. This is best appreciated in FIGS. 73 and 77. The left group and the right group of holes 582 may include individual holes 582 that are spaced apart widely enough in the medial-lateral direction that all five femoral resections 206, 214, 216, 218, 220 may be cut, and a femoral trial component coupled to the resected distal femur, while the base 502 and femoral pin guide 514 remain secured to the femur 100. These widely spaced holes 582 may be located outboard of the mounting holes 584 so that bone pins driven through the widely spaced holes 582 penetrate the epicondyles. Briefly referring to FIGS. 52A and 80A, a first widely spaced hole 582 may be medial to the medial mounting hole 584 and a second widely spaced hole 582 may be lateral to the lateral mounting hole 584, "medial" and "lateral" used with reference to the patient's body. The femoral pin guide 514 may be widened to support the widely spaced holes 582. Advantageously, this detail enables the knee joint, with trial components, to be taken through a range of motion with the femoral pin guide 514 secured to the femur 100. Femoral alignment to the mechanical axis 202 of the leg is thus preserved until the knee is proven to function satisfactorily with trial components. The femoral pin guide 514 includes two mounting holes 584 in the distal medial and lateral corners. A hole (not shown) may be present centered between the mounting holes 584. The femoral pin guide 514 includes a first post 586 and a second post 588 protruding from the bone facing surface 562. Each post 586, 588 includes an oblong tab 590 on at least one side of the free end of the post. The tabs 590 are shown on the distal sides of the posts 586, 588 but may be on the proximal sides or elsewhere instead to match the oblong holes 530, 532, 534 of the base 502. The femoral pin guide 514 may be analogous to a proximal portion of the tibial-femoral pin guide 310.

Figures 53A, 53B:
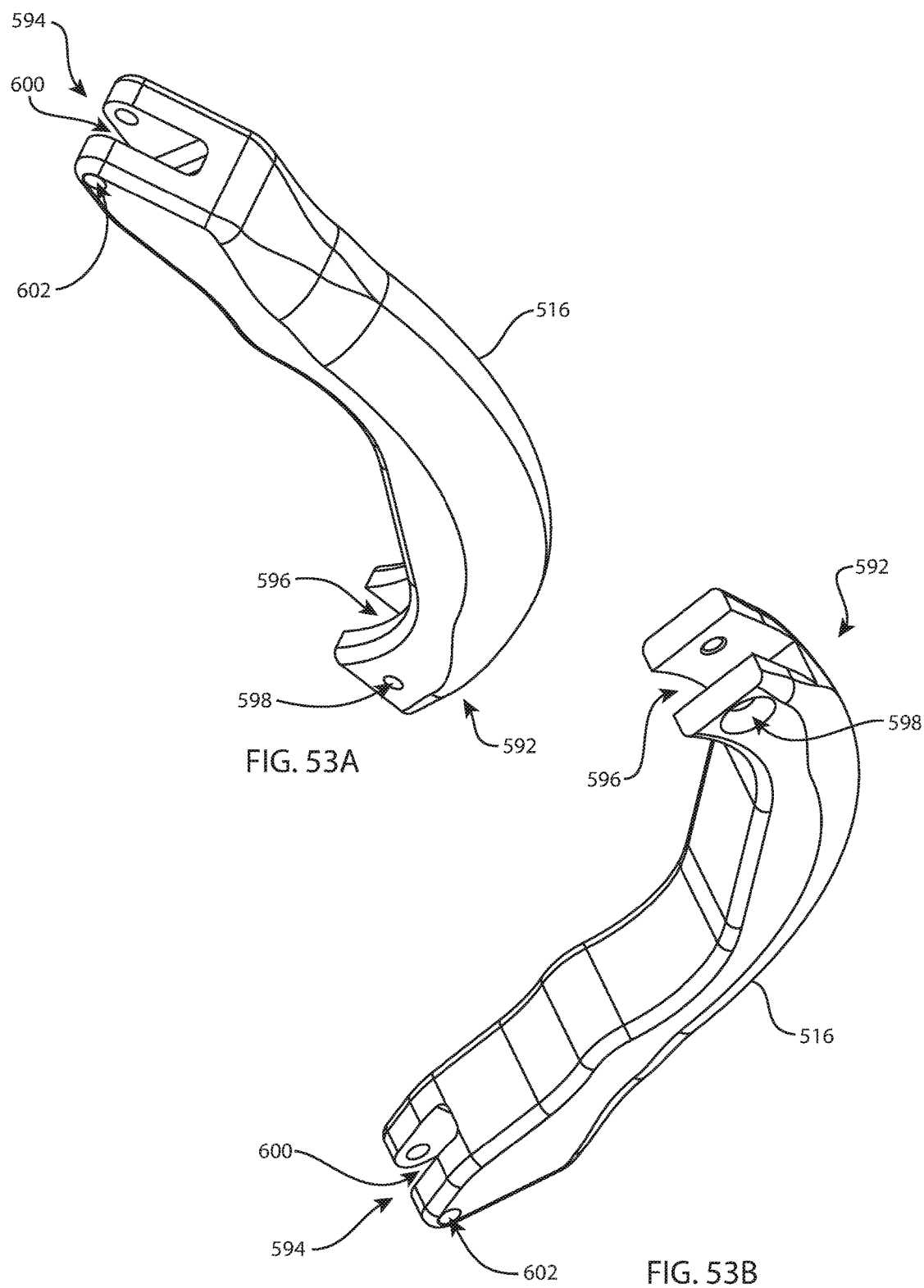
FIG. 53A is a perspective view of a handle of the femoral riser assembly of FIG. 50A.
FIG. 53B is another perspective view of the handle of FIG. 53A from a different direction.

Referring to FIGS. 53A and 53B, the handle 516 is an elongated curved part with a distal portion 592 and a proximal portion 594. The distal portion 592 includes a slot 596. A hole 598 extends through the handle 516 across the slot 596. The proximal portion 594 includes a slot 600. A hole 602 extends through the handle 516 across the slot 600.

Figure 48A:
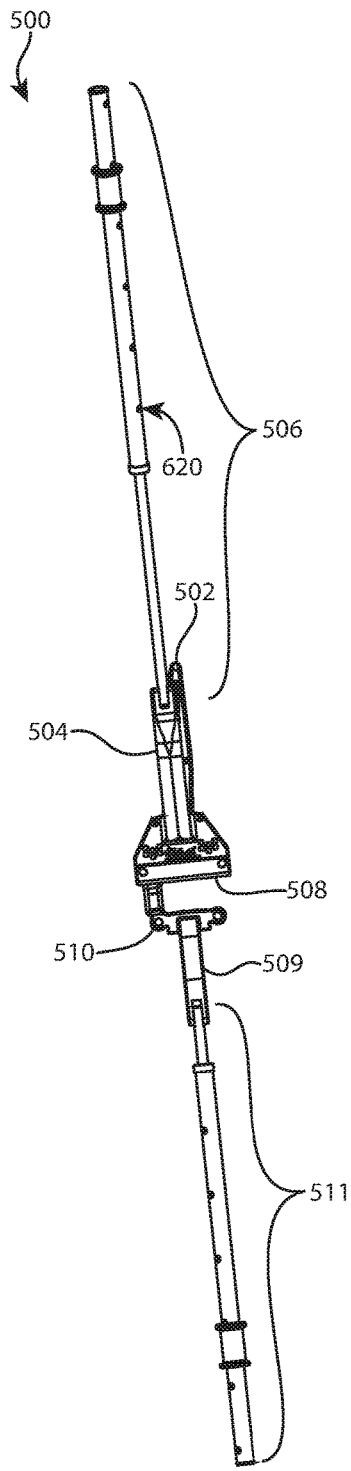
FIG. 48A is a top view of the instrument system of FIG. 47A.
Figure 48B:
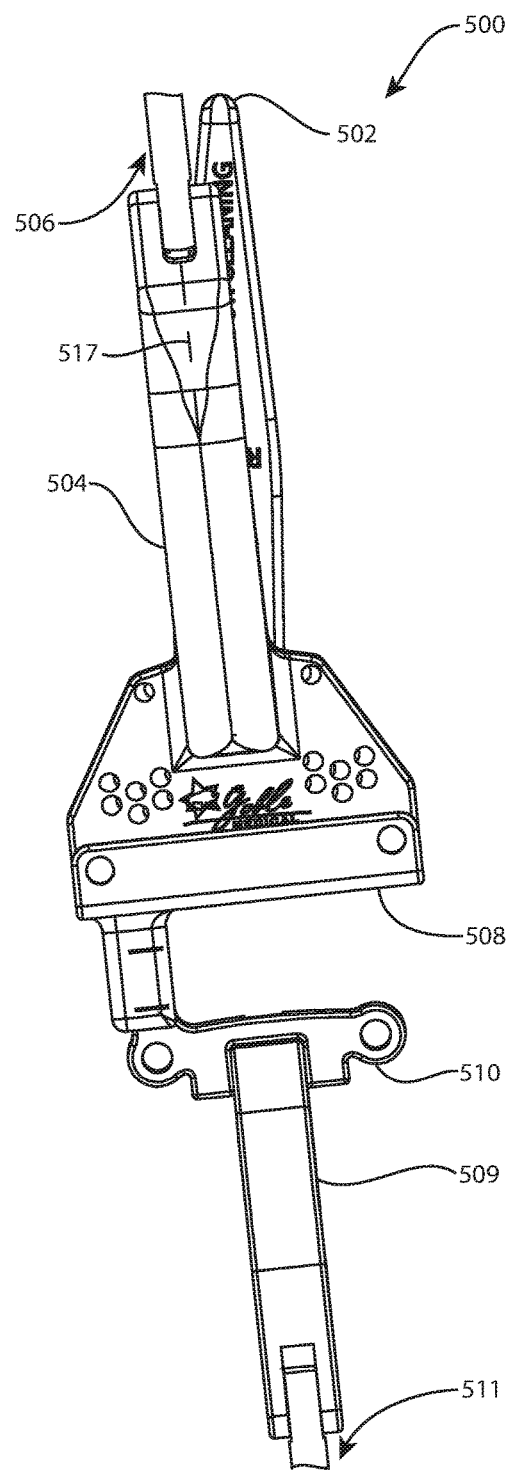
FIG. 48B is an enlarged detail view of a portion of the instrument system of FIG. 48A.

The handle 516 is coupled to the femoral pin guide 514 by inserting the tab 576 into the slot 596 so that the proximal portion 568 and the proximal portion 594 extend in the same direction, aligning the hole 598 with the hole 578, and inserting a fastener through the holes 598, 578. Referring briefly to FIGS. 48B and 80B, the handle 516 extends along the mechanical axis 202 of the leg in use, at least in an anterior view. Therefore, the handle 516 may be said to have a longitudinal axis 517 that extends in a proximal-distal direction.

The femoral riser 504 may be rigidly coupled to the base 502 in one or more orientations. In the example shown, the femoral riser 504 may be coupled to the base 502 in two orientations corresponding to a left or right knee with a fixed angle 204. The first post 586 is received in oblong hole 530 and the second post 588 is received in oblong hole 532 or oblong hole 534. Then the cam 512 may be rotated within the pocket 528 until the resilient portion 550 contacts the first post 586, pushing the tabs 590 to engage the shelves 536 to lock the base 502 to the femoral riser 504. Additional orientations may be provided by providing additional oblong holes, like holes 532, 534, to receive the second post 588. For example, an array of four oblong holes may be provided to provide a choice of left or right knee and small or large angle 204 between the mechanical axis 202, represented by the axis 517 of the handle 516, and the femoral shaft axis 200, represented by the axis 503 of the base 502. It is contemplated that the angle 204 may be adjustable between 4 degrees and 7 degrees by providing an array of oblong holes to receive the second post 588. Briefly referring to FIGS. 49B and 77, when the femoral riser 504 is coupled to the base 502, the bone facing surface 562 of the femoral pin guide 514 is spaced apart anteriorly with respect to the bone contacting surface 518 of the base. This spacing is advantageous because it complements the natural anatomy of the intact distal femur by avoiding contact with the anterior aspects of the femoral condyles, and also because it provides room to make the anterior femoral resection 214 and anterior femoral chamfer cut 216 with the base 502 and femoral riser 504 coupled to the femur 100.

Figure 49A:
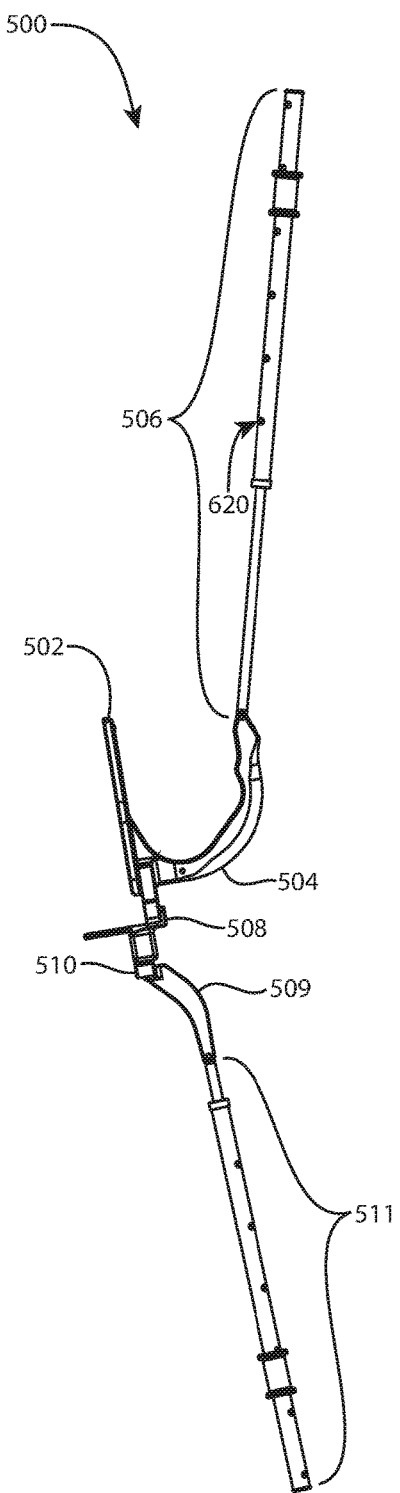
FIG. 49A is a side view of the instrument system of FIG. 47A.
Figure 54A:
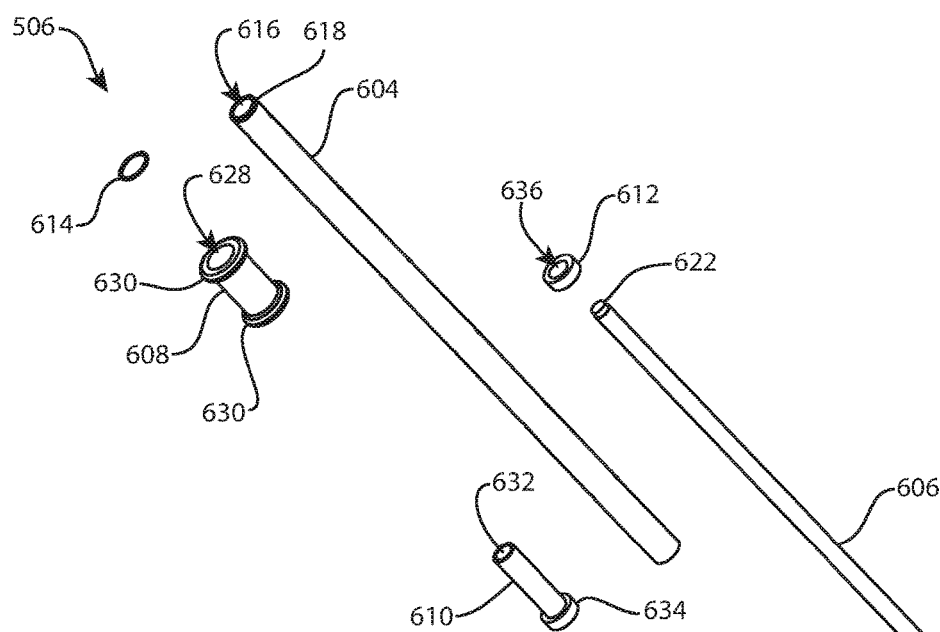
FIG. 54A is an exploded perspective view of a femoral extension rod assembly of the instrument system of FIG. 47A.
Figure 54B:
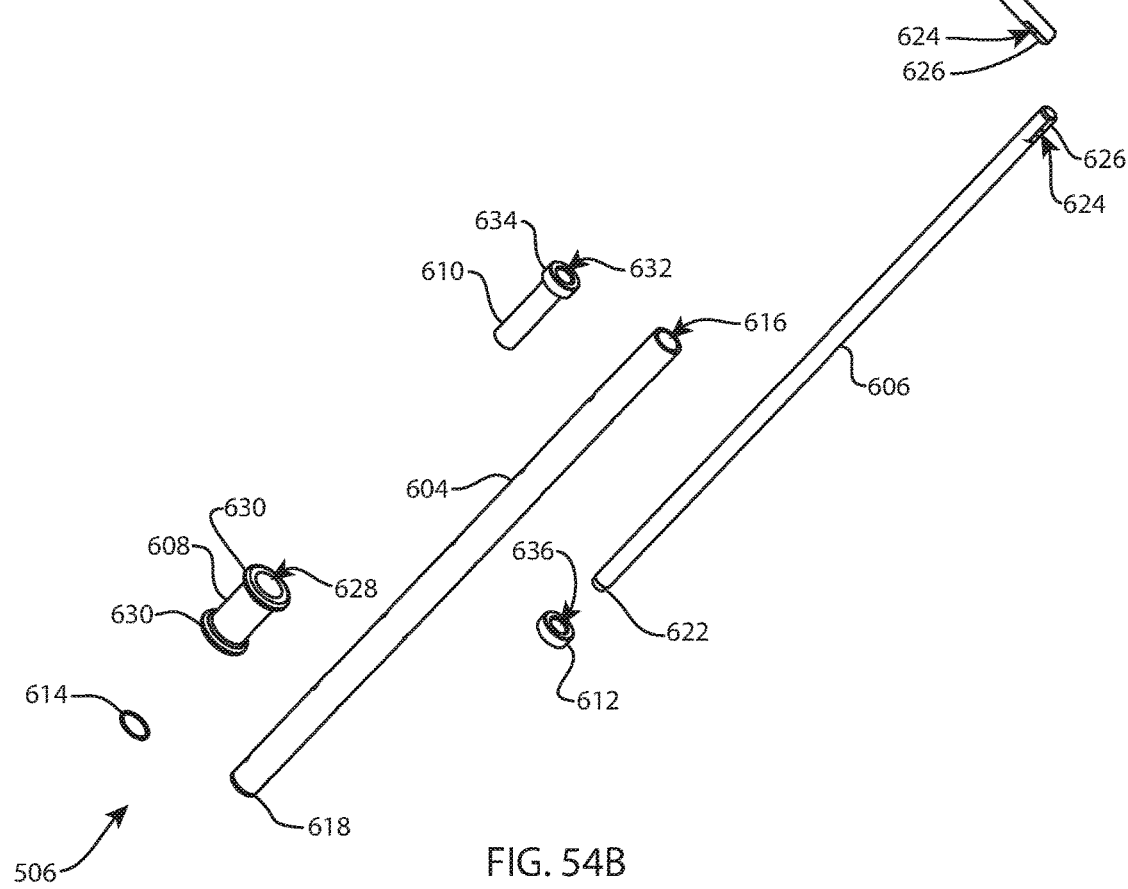
FIG. 54B is another exploded perspective view of the femoral extension rod assembly of FIG. 54A from a different direction.

Referring to FIGS. 54A and 54B, the femoral extension rod 506 may be a telescopic assembly including an outer extension rod 604, an inner extension rod 606, a spool 608, a sleeve 610, a ring 612, and a retaining ring 614. The femoral extension rod 506 may alternately be a fixed length rod like femoral extension rod 306. The outer extension rod 604 is a tubular part with a central longitudinal hole 616 and an external groove 618 around one end. One or more ports 620 may pierce the outer extension rod 604. The ports 620 are best seen in FIGS. 48A and 49A. The inner extension rod 606 is a cylindrical rod with an external groove 622 around one end and a transverse hole 624 through an opposite end. The inner extension rod 606 may include flats 626 on both sides around the hole 624. The spool 608 is a tubular part with a central longitudinal hole 628 and an external flange 630 projecting outwardly around each end. The sleeve 610 is a tubular part with a central longitudinal hole 632 and an external flange 634 projecting outwardly around one end. The ring 612 has a central hole 636.

The femoral extension rod 506 may be assembled as follows. The ring 612 is permanently fixed to the groove 622 of the inner extension rod 606. The ring 612 and inner extension rod 606 slide into the outer extension rod 604 so that the ring 612 is pointed toward the same end of the assembly as the groove 618 of the outer extension rod 604. The inner extension rod 606 slides into the sleeve 610, and the sleeve slides into the outer extension rod 604 so that the flange 634 abuts the end of the outer extension rod 604 opposite the groove 618. The sleeve 610 is fixed to the outer extension rod 604. The ring 612 is too large to pass through the sleeve 610. The spool 608 slides over the outer extension rod 604. The retaining ring 614 rests in the groove 618 of the outer extension rod. The retaining ring 614 and the flange 634 are each too large to pass through the spool 608.

Figures 47A, 47B:
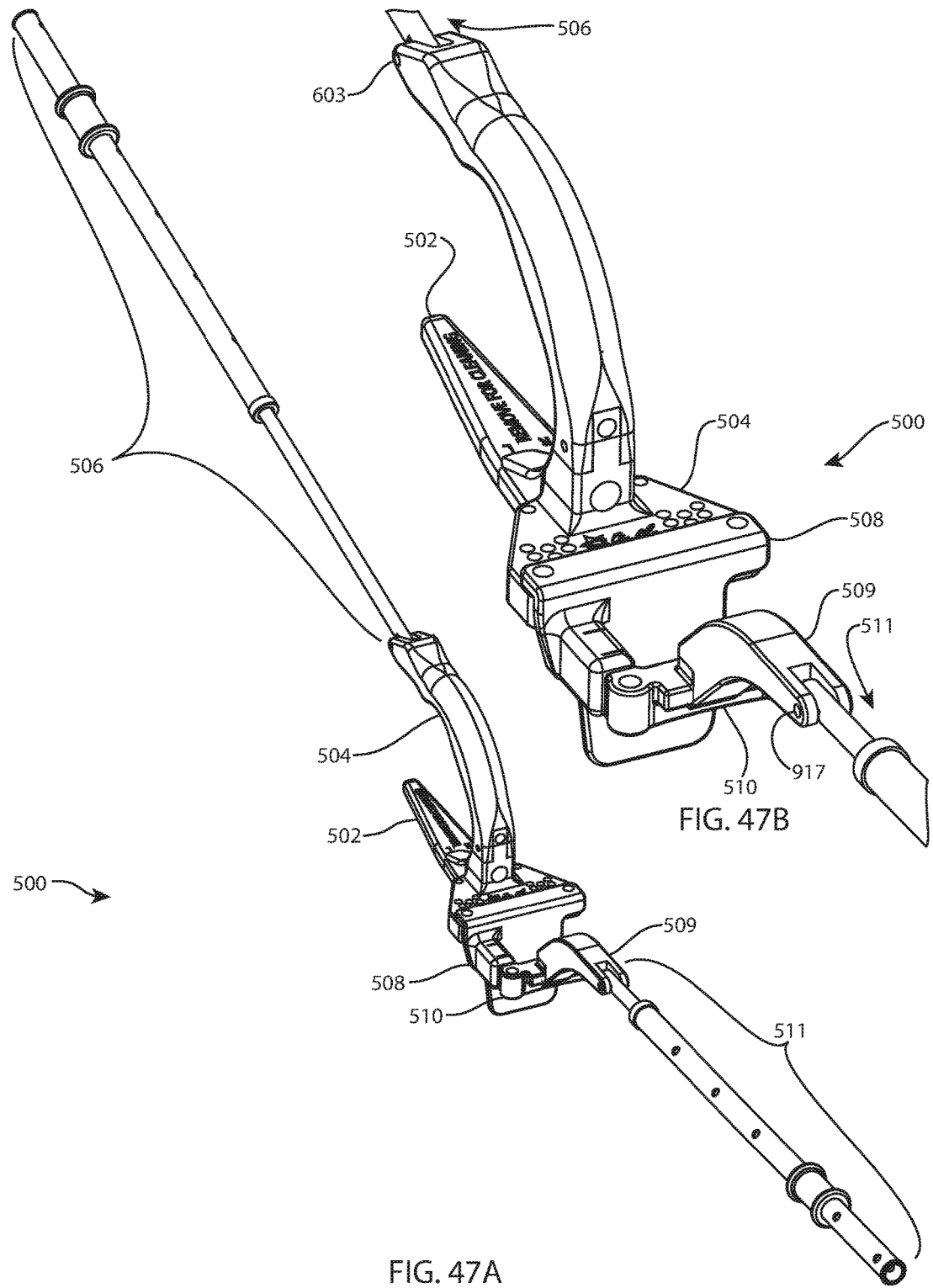
FIG. 47A is a perspective view of yet another instrument system, showing an assembly of components similar to those shown in FIG. 21A.
FIG. 47B is an enlarged detail view of a portion of the instrument system of FIG. 47A.
Figure 49B:
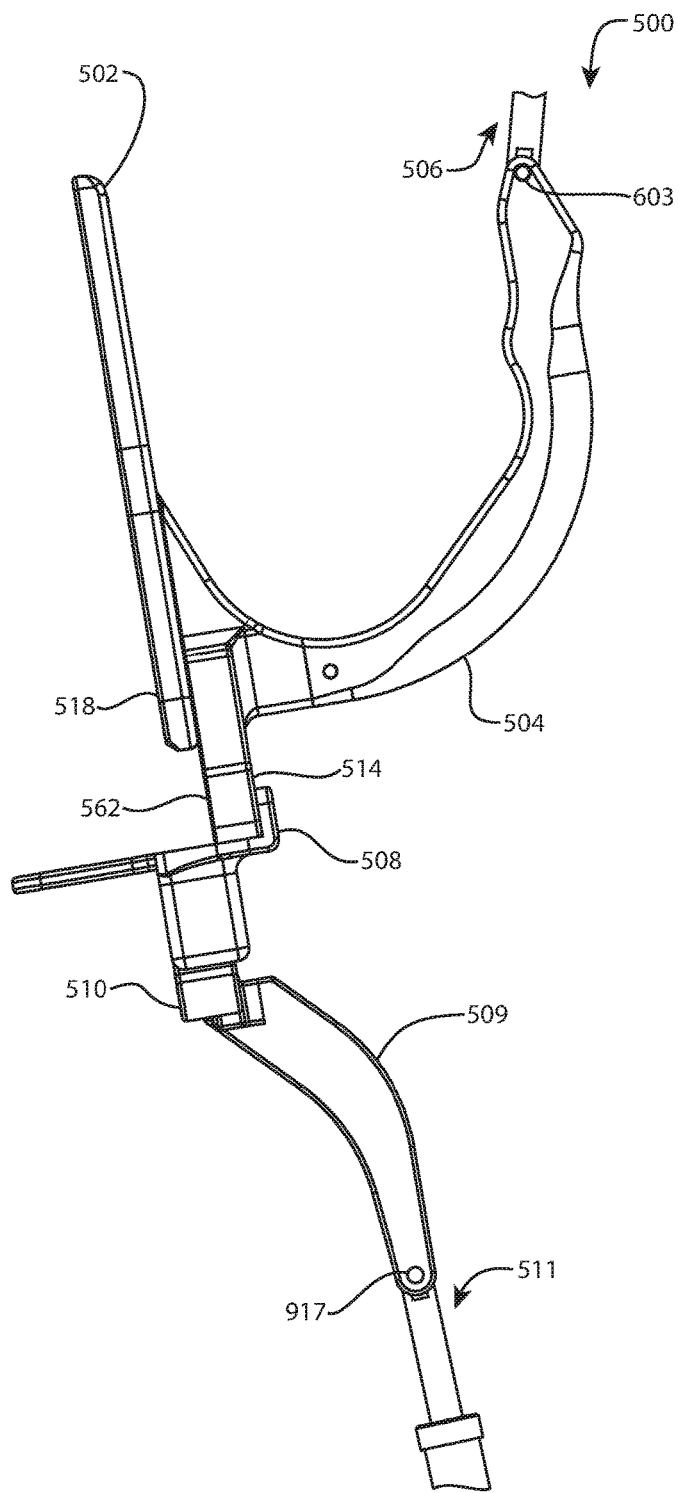
FIG. 49B is an enlarged detail view of a portion of the instrument system of FIG. 49A.

The assembled femoral extension rod 506 may be coupled to the handle 516 by inserting the end of the inner extension rod 606 with the hole 624 into the slot 600, aligning the hole 602 with the hole 624, and inserting a fastener through the holes 602, 624 to form a hinge 603 (FIGS. 47B and 49B). The femoral extension rod 506 is free to pivot about the hinge 603. In use, the femoral extension rod 506 pivots in an anterior-posterior direction which is generally parallel to the sagittal plane. The femoral extension rod 506 is constrained against pivoting in a medial-lateral direction which is generally parallel to the coronal plane. The outer extension rod 604 is free to slide (telescope) along the inner extension rod 606 at least until the ring 612 abuts the sleeve 610, and the spool 608 is free to slide along the outer extension rod at least between the flange 634 and the retaining ring 614. However, the spool 608 is captive to the outer extension rod 604, which is captive to the inner extension rod 606. The end of the inner extension rod 606 with the hole 624 is the distal end of the femoral extension rod 506, and the end of the outer extension rod 604 with the retaining ring 614 is the proximal end of the femoral extension rod.

Figure 55A:
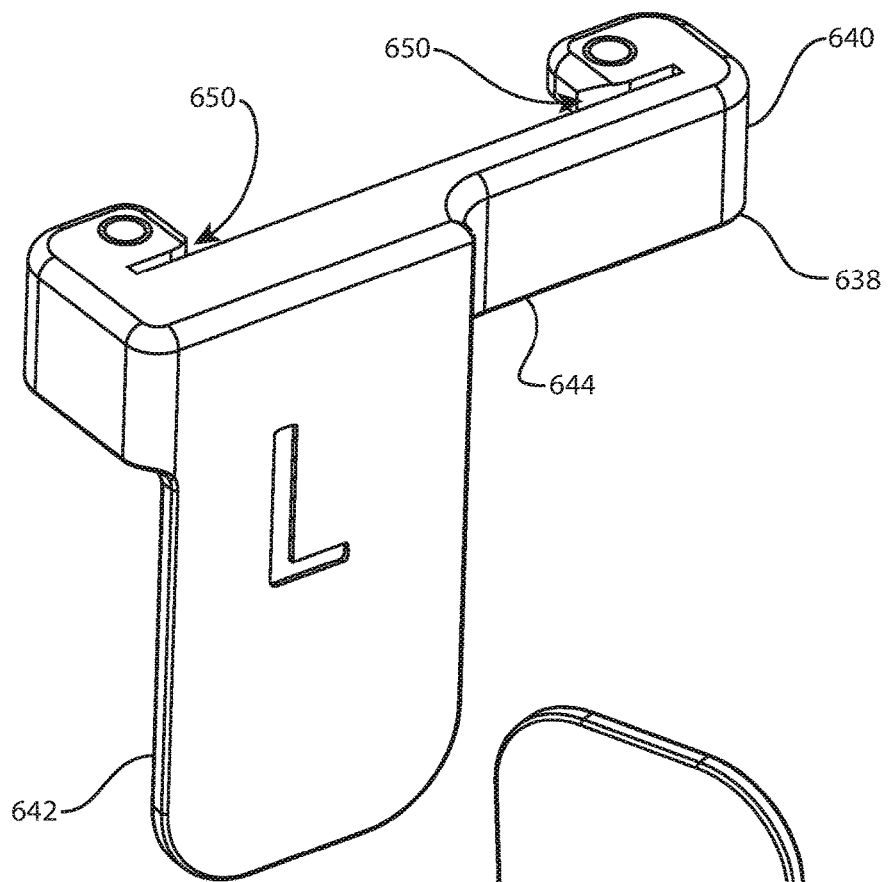
FIG. 55A is a perspective view of a distal femoral condyle block for use with the instrument system of FIG. 47A.
Figure 55B:
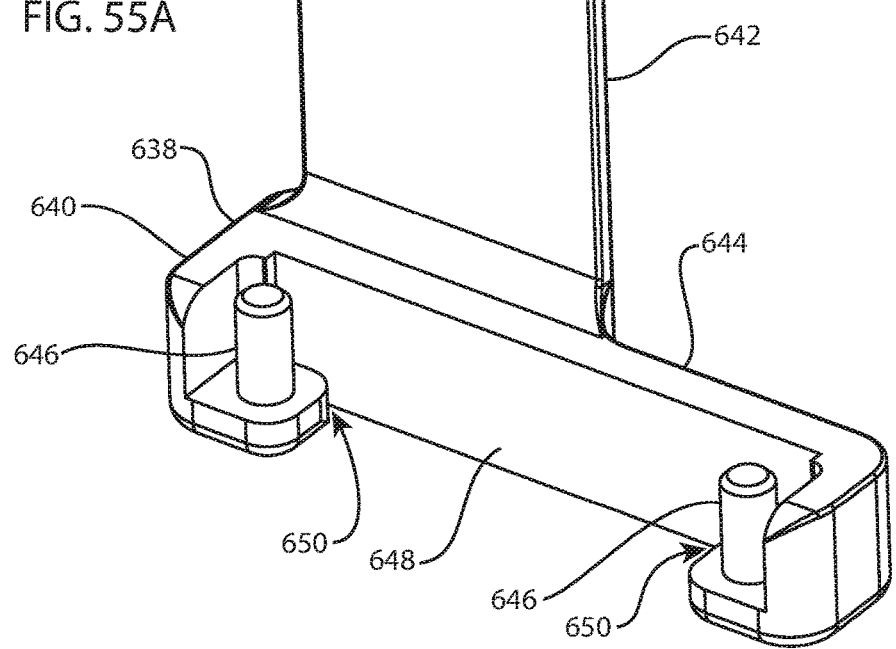
FIG. 55B is another perspective view of the distal femoral condyle block of FIG. 55A from a different direction.

Referring to FIGS. 55A and 55B, a distal femoral condyle block 638 includes a mounting portion 640 and a paddle 642. The mounting portion 640 includes a bar 644 with a peg 646 extending from each end of the bar. The pegs 646 are parallel, and in this example they are separate pins which are coupled to the bar 644. However, the pegs 646 may be integrally formed with the bar 644. The bar 644 includes a planar cut guide surface 648 which faces the pegs 646 and which may extend into one or more slots 650 beside the pegs. The cut guide surface 648 may be entirely enclosed within a single slot 650 rather than having an open middle portion as shown. The slot(s) 650 may be referred to as saw slots or cut guide slots. The paddle 642 in this example is a generally rectangular flat plate which is integrally formed with the bar 644 and extends from the bar 644 in the same direction as the pegs 646. The illustrated distal femoral condyle block 638 is for a left knee, hence the paddle 642 is positioned to rest on a distal medial femoral condyle in use.

The distal femoral condyle block 638 releasably couples to the femoral riser 504. The pegs 646 fit into the mounting holes 584 so that the cut guide surface 648 faces the distal portion 566. There is room to pass a saw blade between the cut guide surface 648 and the distal portion 566 to make a distal femoral resection 206; thus a saw slot or cut guide slot is formed between these features. The distal femoral condyle block 638 may function as a distal femoral cut guide.

The illustrated distal femoral condyle block 638 is designed so that the proximal surface of the paddle 642 is 9 mm from the distal surface of the distal portion 566 when the distal femoral condyle block 638 is coupled to the femoral riser 504, and so that the cutting slot is formed between the cut guide surface 648 and the distal surface of the distal portion 566. However, there are situations where it may be desirable to take more than 9 mm of bone from the distal femoral condyles, for example in patients with flexion contracture where only the extension gap requires adjustment so that the knee can be brought to full extension. Flexion contracture may only be appreciated after an initial 9 mm distal femoral resection 206 has been made and the knee joint has been taken through a range of motion with trial components. The system 500, as well as the other systems disclosed herein, may be adapted to provide multiple locations (cutting slot positions) for the distal femoral resection 206. The distal femoral condyle block 638 may be designed so that the proximal surface of the paddle 642 is more than 9 mm from the distal surface of the distal portion 566 when the distal femoral condyle block 638 is coupled to the femoral riser 504. Dimensions between 11 mm and 17 mm are contemplated. This positions the distal surface of the distal portion 566 sufficiently proximal to the distal medial femoral condyle so that the distal femoral resection 206 may be adjusted (re-cut) to take 2 mm, up to 8 mm, more bone from the distal femoral condyles, from an initial distal femoral resection 206 that is 9 mm proximal to the distal medial femoral condyle. The distal femoral condyle block 638 may be designed with multiple discrete cutting slots, the distal-most cutting slot including the cut guide surface 648 spaced 9 mm from the proximal surface of the paddle 642, and the more proximal cutting slots incrementally spaced, for example 2 mm apart; or the distal femoral condyle block 638 may include a movable cutting slot that can be adjusted in the proximal-distal direction to remove 9 mm to 17 mm of bone from the distal femoral condyles; or a set of distal femoral condyle blocks 638 may be provided, each with a different distal femoral resection depth; or the distal femoral condyle block 638 may be used only to initially position the base 502 and the femoral riser 504, and one or more separate distal femoral cut blocks (not shown) may be provided, that releasably couple to the femoral riser 504 in the same way as the distal femoral condyle block 638. Of course the 17 mm example dimension may be larger or smaller as a matter of design choice. This paragraph further supports the advantages of keeping the base 502 and the femoral pin guide 514 secured to the femur 100 while the knee joint is taken through a range of motion with trial components. The distal femoral resection 206 may be adjusted (re-cut) in alignment with the mechanical axis 202 of the leg.

Figure 72A:
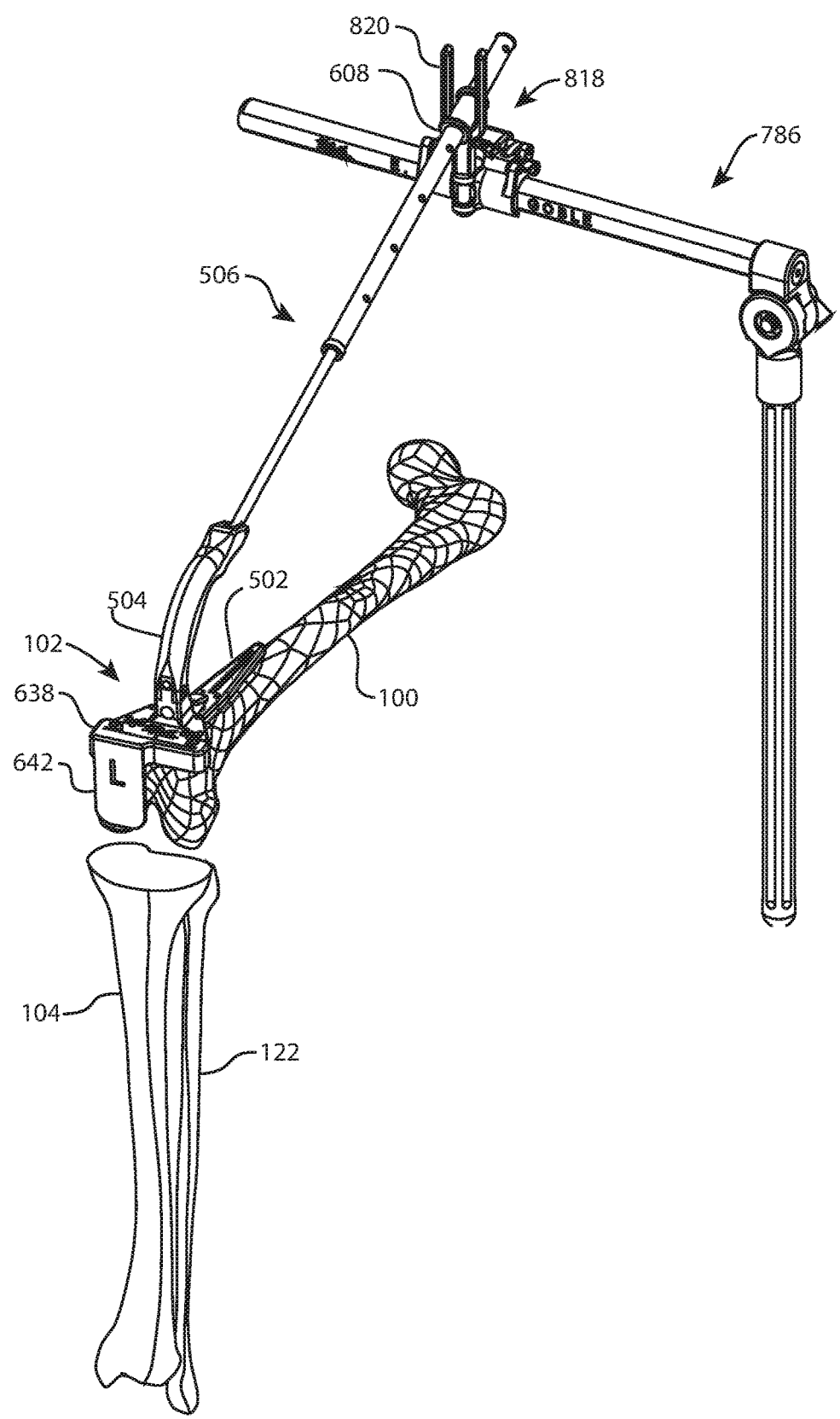
FIG. 72A is a perspective view of the femur, tibia, fibula, femoral support arm assembly, and target clamp assembly of FIG. 71, after positioning the base of FIG. 47A on the anterior distal femur, extending the femoral extension rod assembly of FIG. 47A through the target of the target clamp assembly, and coupling the distal femoral condyle block of FIG. 55A to the femoral riser assembly.
Figure 72B:
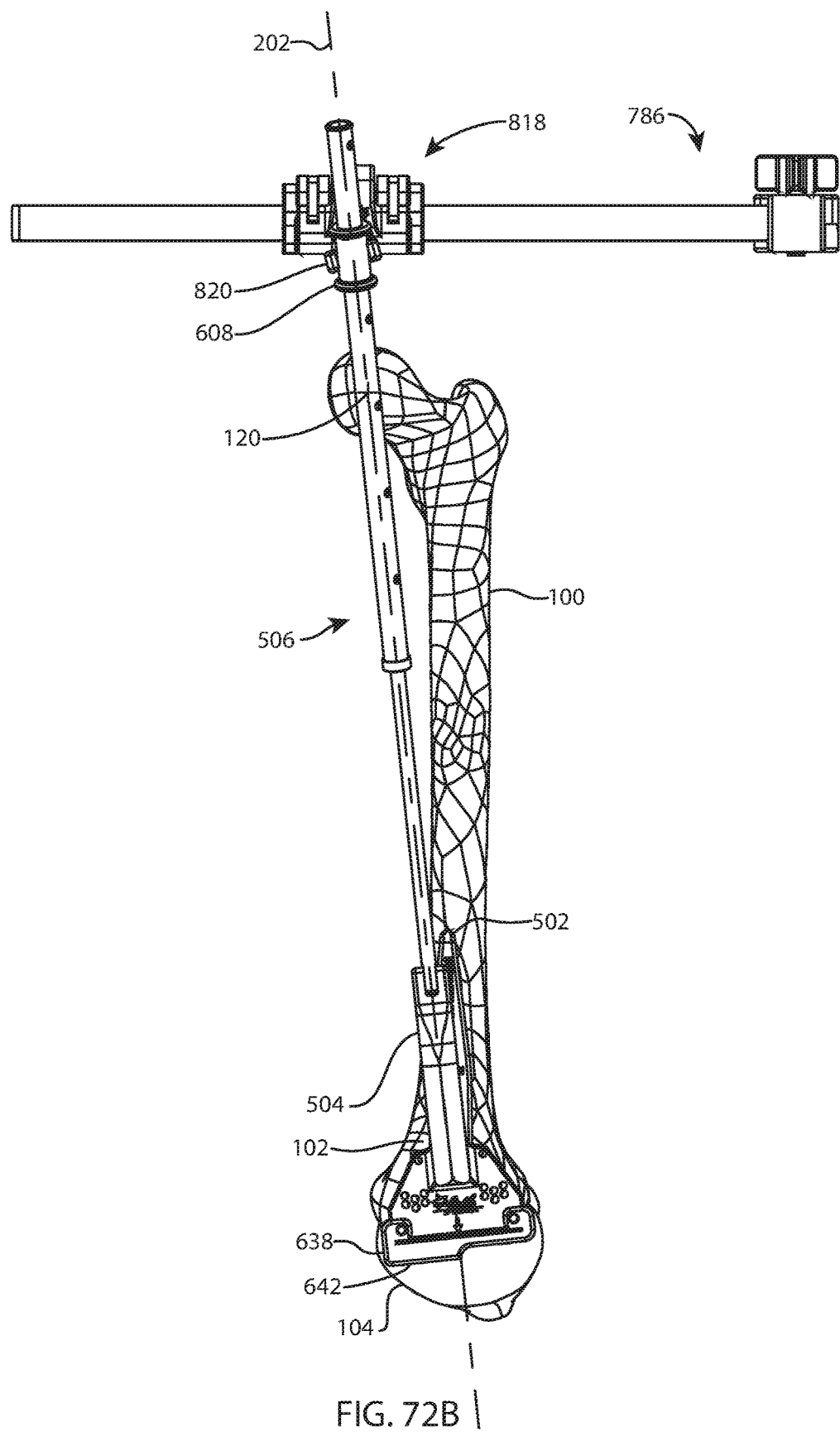
FIG. 72B is a top view of the femur, tibia, fibula, femoral support arm assembly, target clamp assembly, base, femoral riser assembly, distal femoral condyle block, and femoral extension rod assembly of FIG. 72A.
Figure 73:
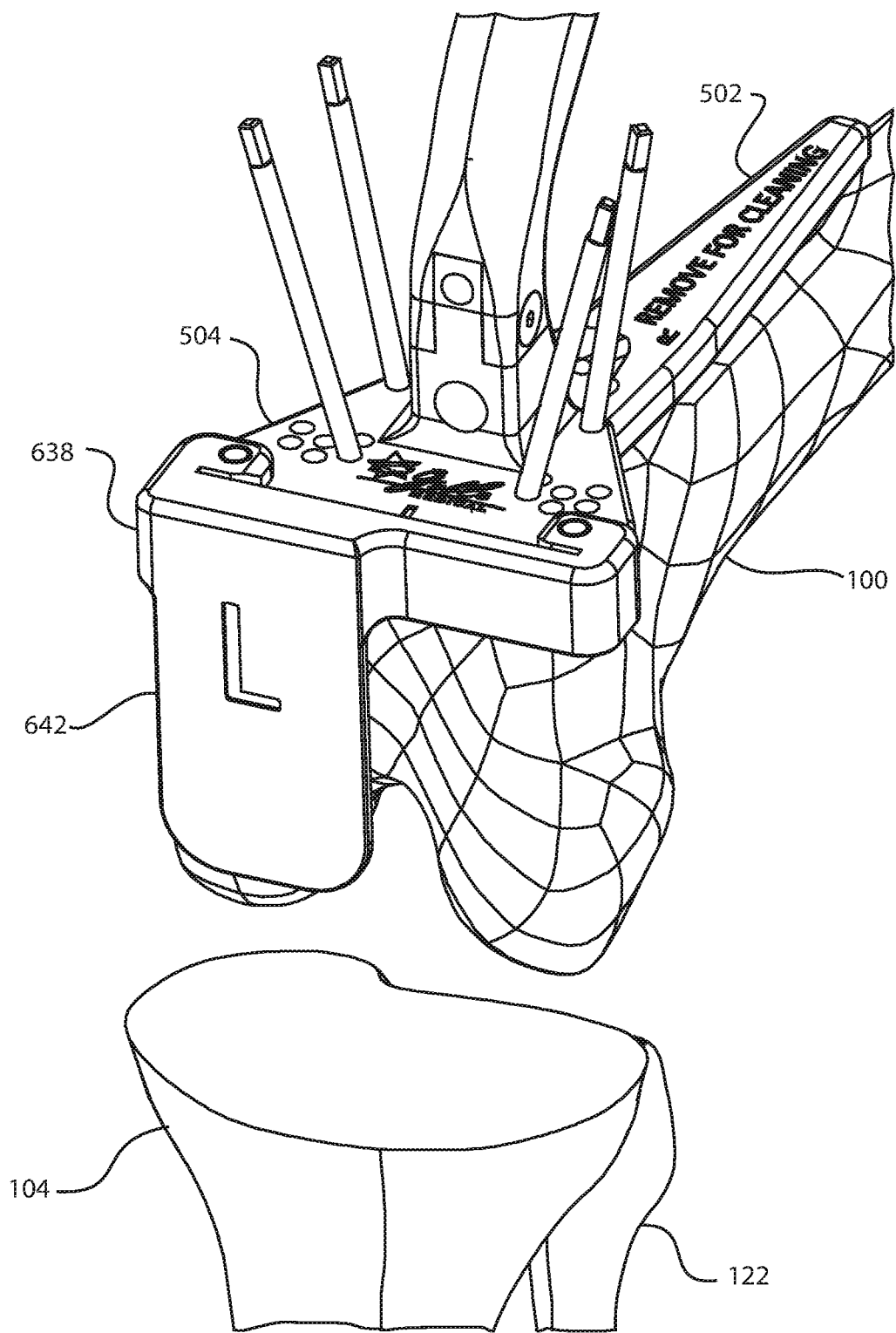
FIG. 73 is a perspective view of the femur, tibia, fibula, base, femoral riser assembly, and distal femoral condyle block of FIG. 72A, after fixing the femoral riser assembly to the anterior distal femur with pins.
Figure 75:
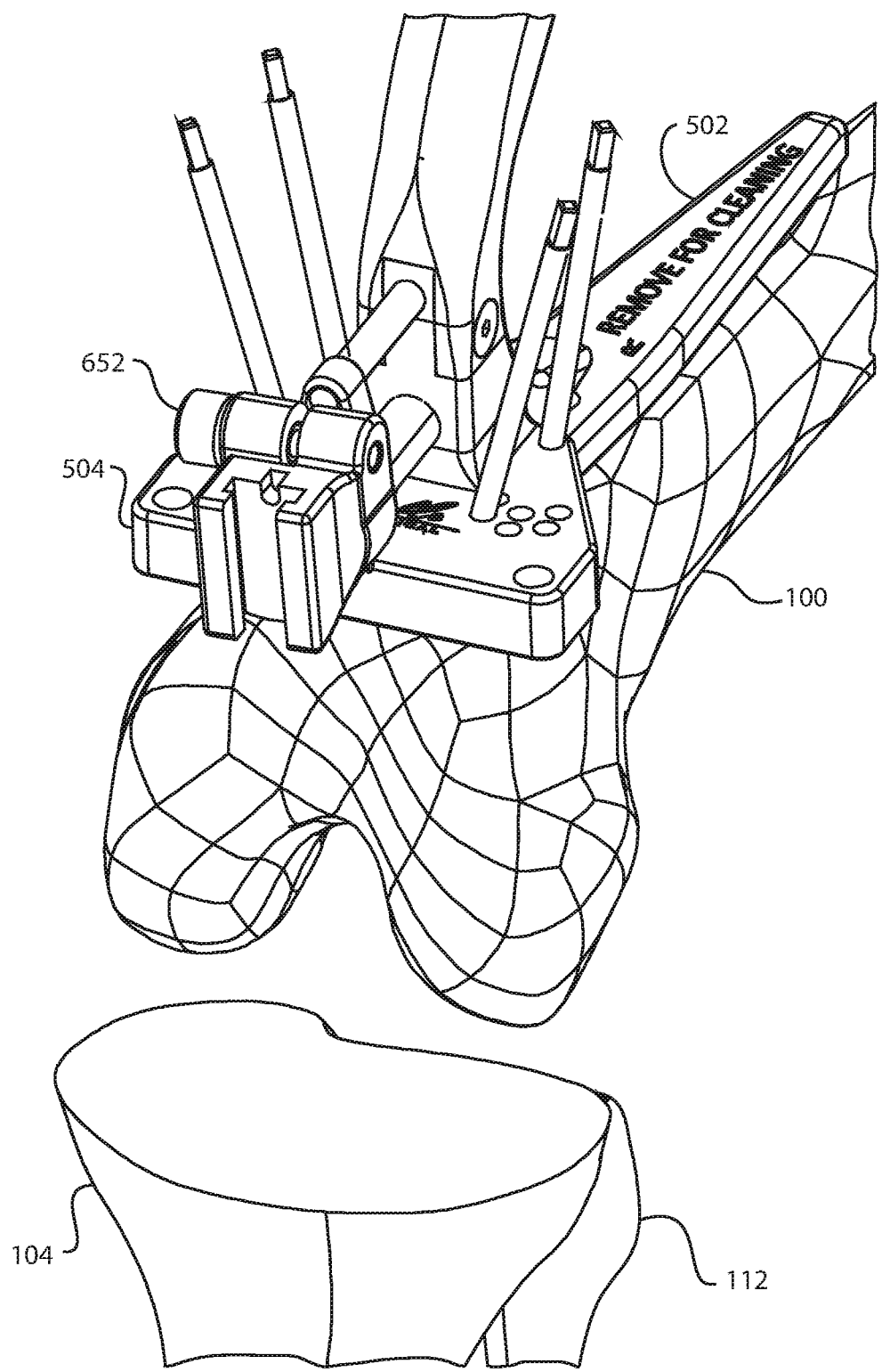
FIG. 75 is a perspective view of the femur, tibia, fibula, base, and femoral riser assembly of FIG. 74, after attaching the angle block assembly of FIG. 56A.
Figure 76:
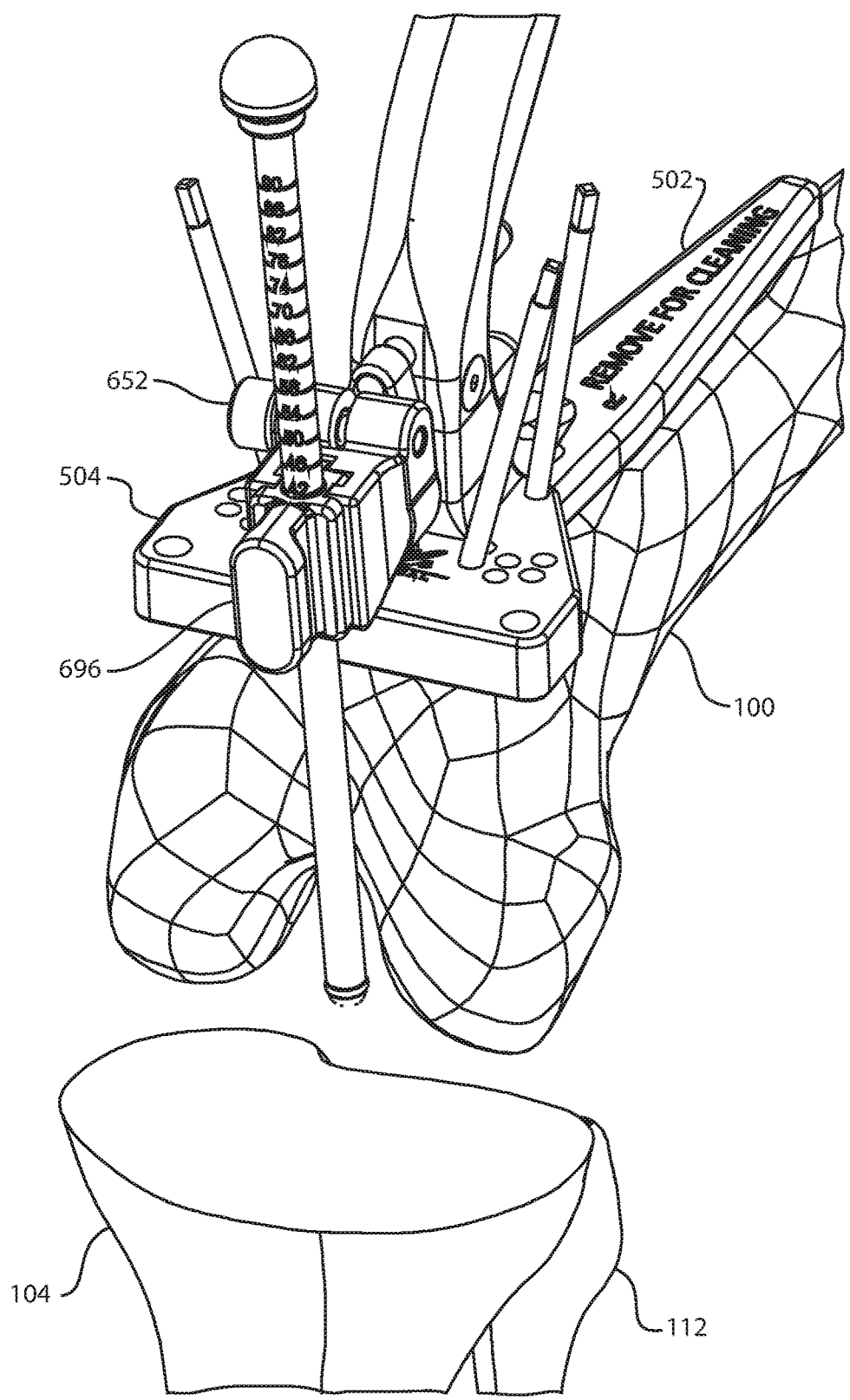
FIG. 76 is a perspective view of the femur, tibia, fibula, base, femoral riser assembly, and angle block assembly of FIG. 75, after coupling the Whiteside's line gage assembly of FIG. 58A to the angle block assembly.
Figure 77:
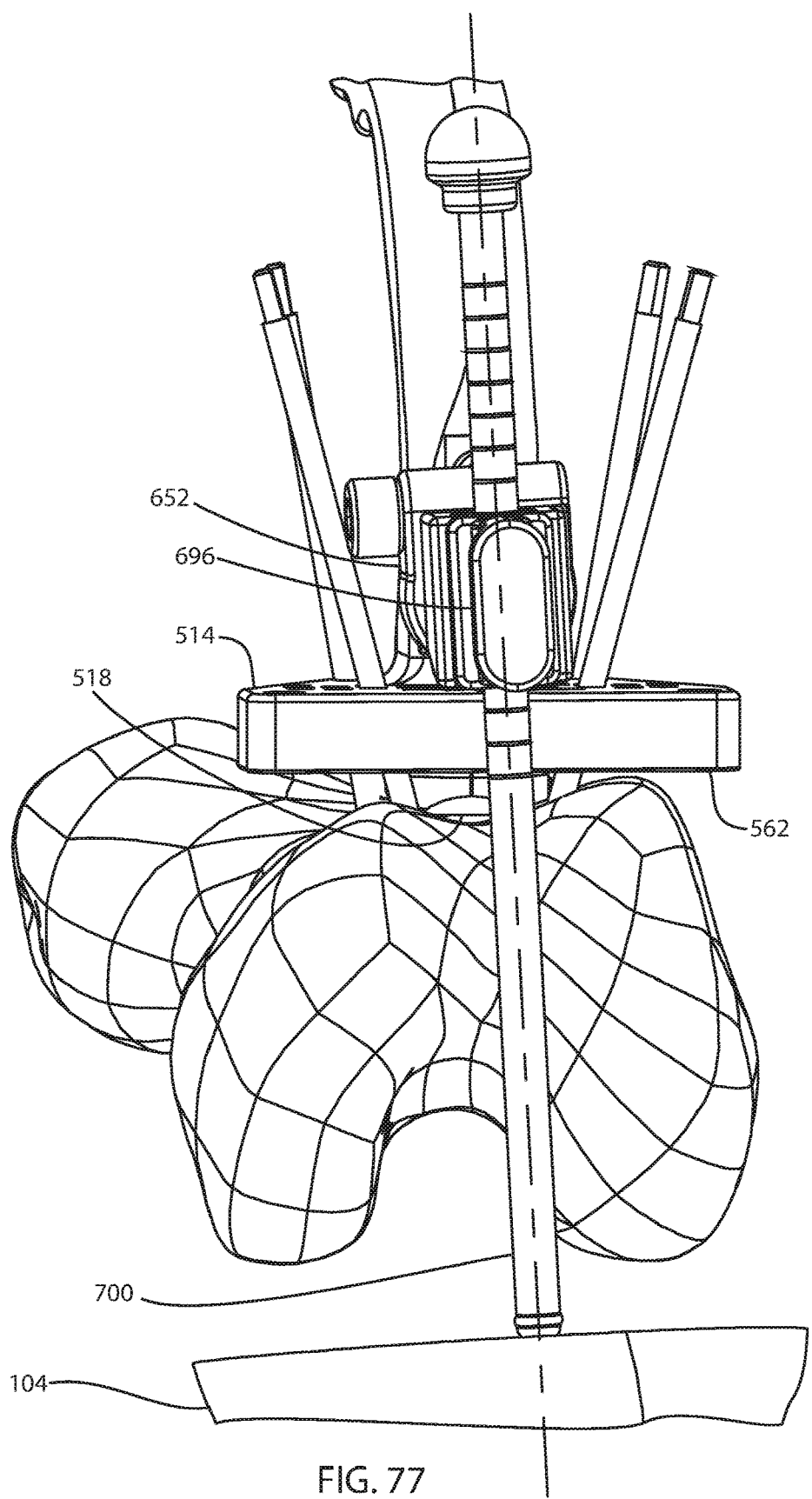
FIG. 77 is a distal view of the femur, tibia, base, femoral riser assembly, angle block assembly, and Whiteside's line gage assembly of FIG. 76, after locking the Whiteside's line gage assembly in an orientation parallel to Whiteside's line.

The illustrated distal femoral condyle block 638 is designed with the mounting portion 640 extending across the full width of the femoral pin guide 514 (FIG. 72B) and the paddle 642 extending across the full width of the distal medial condyle (FIGS. 72A and 73). However, the distal femoral condyle block 638 may be designed with a narrower mounting portion 640, and optionally a narrower paddle 642, so that the distal femoral condyle block 638 may be used simultaneously with the Whiteside's angle gage assembly 696 described below. Referring briefly to FIGS. 75-77, the narrower mounting portion 640 may couple to the distal medial portion of the femoral riser 504. The paddle 642 would still rest against the distal aspect of the medial femoral condyle.

The distal femoral condyle block 638 may be designed to couple to the angle block assembly 652 described next, for example, to the dovetail channel 668; or to the Whiteside's angle gage assembly 696, for example, to the distal dove tail rail 706. Advantageously, this allows the distal femoral condyle block 638 to slide proximally and distally with respect to the femur 100.

Figure 56A:
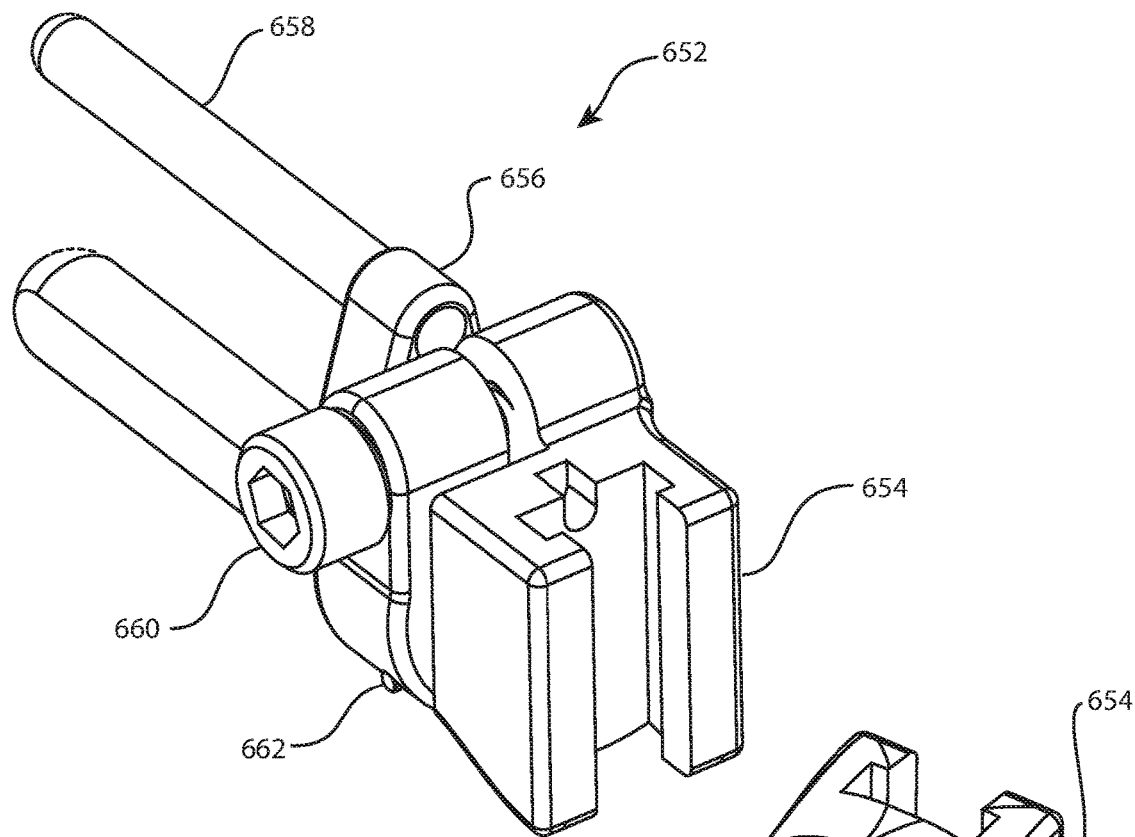
FIG. 56A is a perspective view of an angle block assembly for use with the instrument system of FIG. 47A.
Figure 56B:
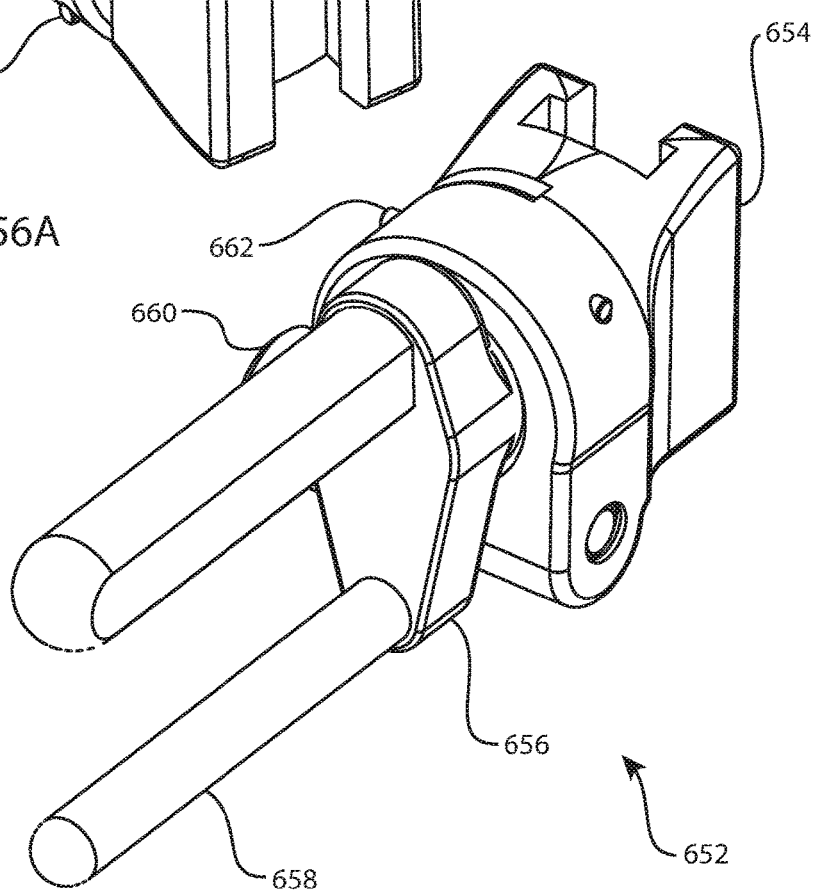
FIG. 56B is another perspective view of the angle block assembly of FIG. 56A from a different direction.

Referring to FIGS. 56A and 56B, an angle block assembly 652 includes an angle block 654, a translation bar 656, a translation pin 658, a bolt 660, and a dowel pin 662. Referring to FIG. 35, the angle block assembly 652 is analogous to the femoral base block assembly 330.

Figure 57A:
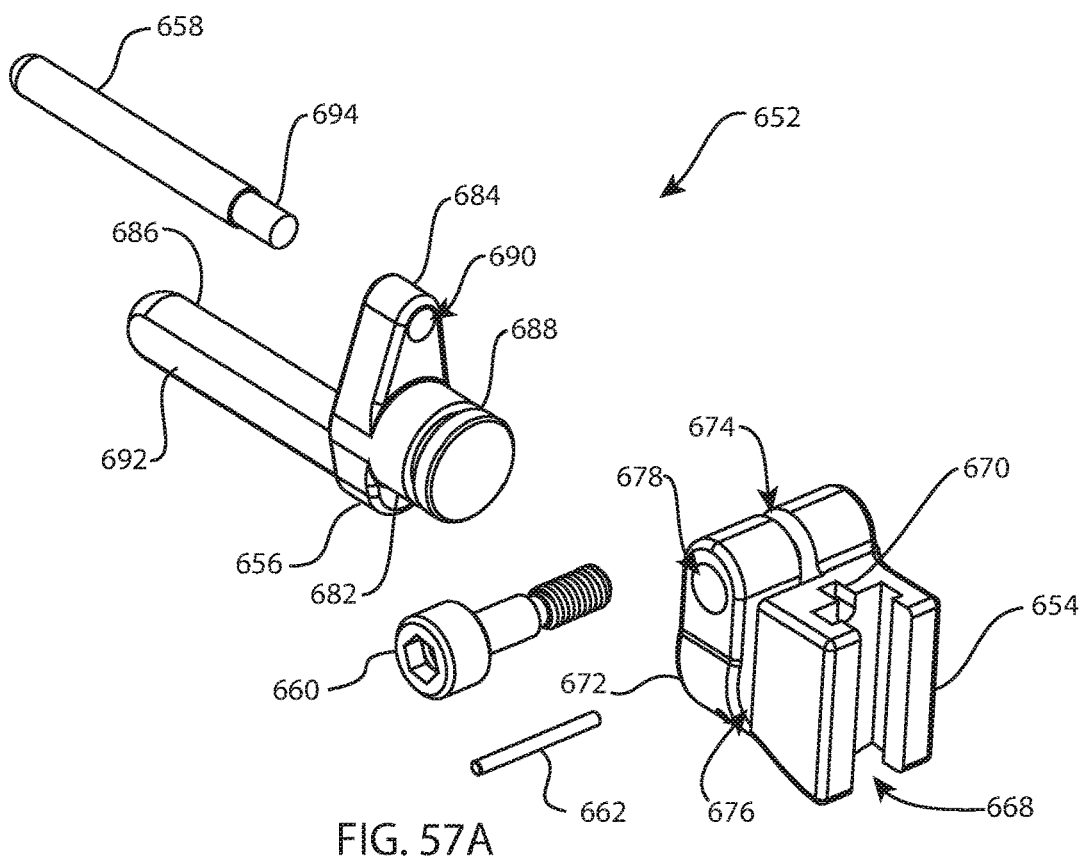
FIG. 57A is an exploded perspective view of the angle block assembly of FIG. 456A.
Figure 57B:
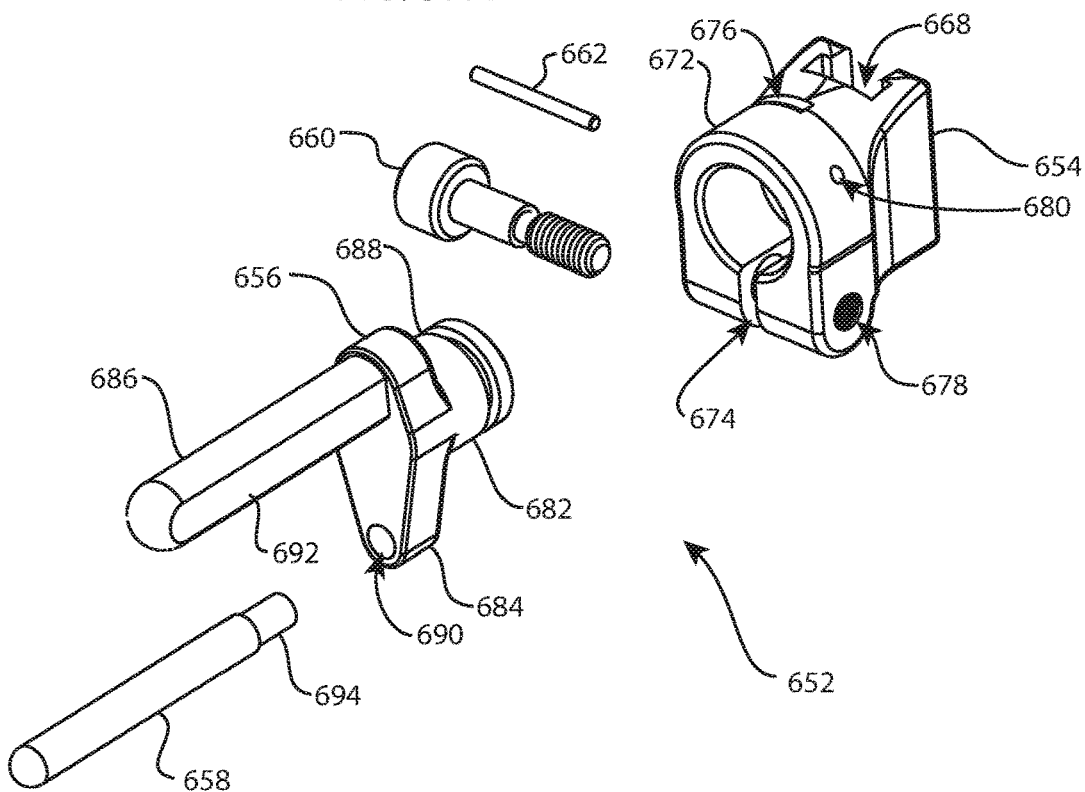
FIG. 57B is another exploded perspective view of the angle block assembly of FIG. 57A from a different direction.

Referring to FIGS. 57A and 57B, the angle block 654 includes a dovetail channel 668 with a notch 670 at one end (the upper or anterior end, in use). The angle block 654 also includes an integral clamp ring 672 opposite the dovetail channel 668. The clamp ring includes a slit 674 that extends through a side of the clamp ring, and a slot 676 that extends between the clamp ring 672 and the dovetail channel 668 along part of the width of the angle block 654. The slit 674 and the slot 676 intersect so that the clamp ring 672 has appropriate flexibility for clamping. A hole 678 extends through the clamp ring 672 across the slit 674. Another hole 680 extends through the clamp ring opposite the slit 674.

The translation bar 656 includes a post 682, a body 684, and a pin 686. These parts may be integrally formed as shown, or separate parts coupled together. The post 682 includes an exterior circumferential groove 688. The body may include one or two holes 690; one hole 690 is illustrated. Bilateral flats 692 may extend along opposite sides of the pin 686.

The translation pin 658 is a cylindrical part with a rounded end and an opposite end having a reduced diameter 694 compared to the rest of the part.

The angle block assembly 652 may be assembled as follows. The hole 690 receives the reduced diameter 694 end of the translation pin 658. The translation pin 658 may be permanently fixed in the hole 690. The clamp ring 672 receives the post 682. The hole 680 and the groove 688 receive the dowel pin 662 to retain the translation bar 656 to the angle block 654 while permitting the translation bar 656 to rotate about the post 682 when the clamp ring 672 is loosened. The hole 678 receives the bolt 660 which is used to tighten and loosen the clamp ring 672.

The angle block assembly 652 may be coupled to the femoral riser 504. The hole 572 receives the pin 686 and the hole 574 receives the pin 658 so that the translation bar 656, with attached translation pin 658, is constrained to slide straight in and out of the femoral riser 504. In use, the pins 686, 658 extend proximally and the dovetail channel 668 faces distally.

Figure 58A:
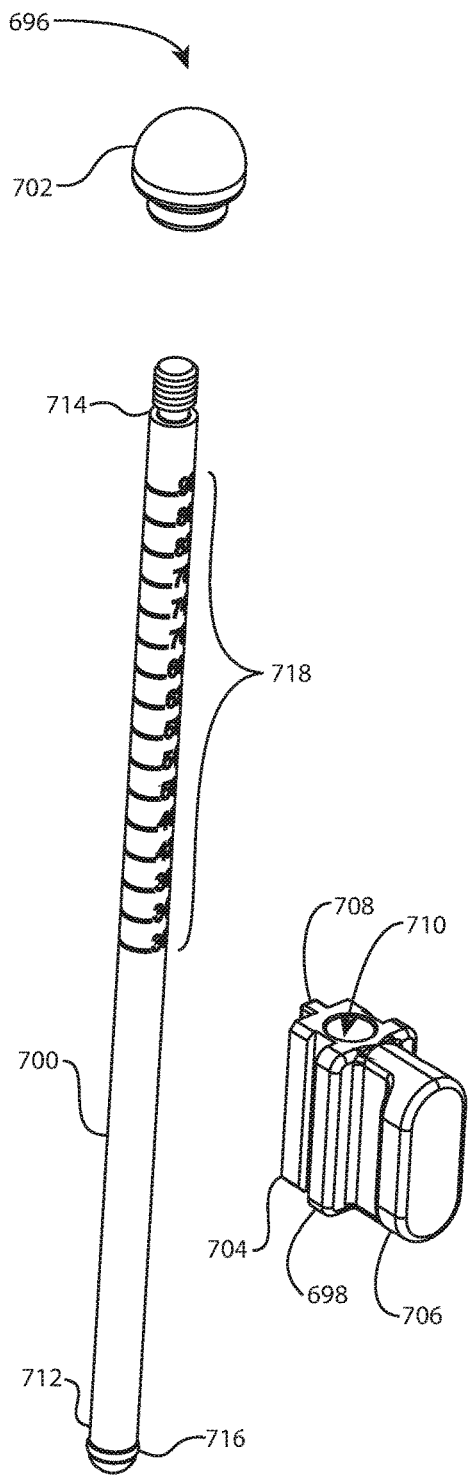
FIG. 58A is an exploded perspective view of a Whiteside's angle gage assembly for use with the angle block assembly of FIG. 56A.
Figure 58B:
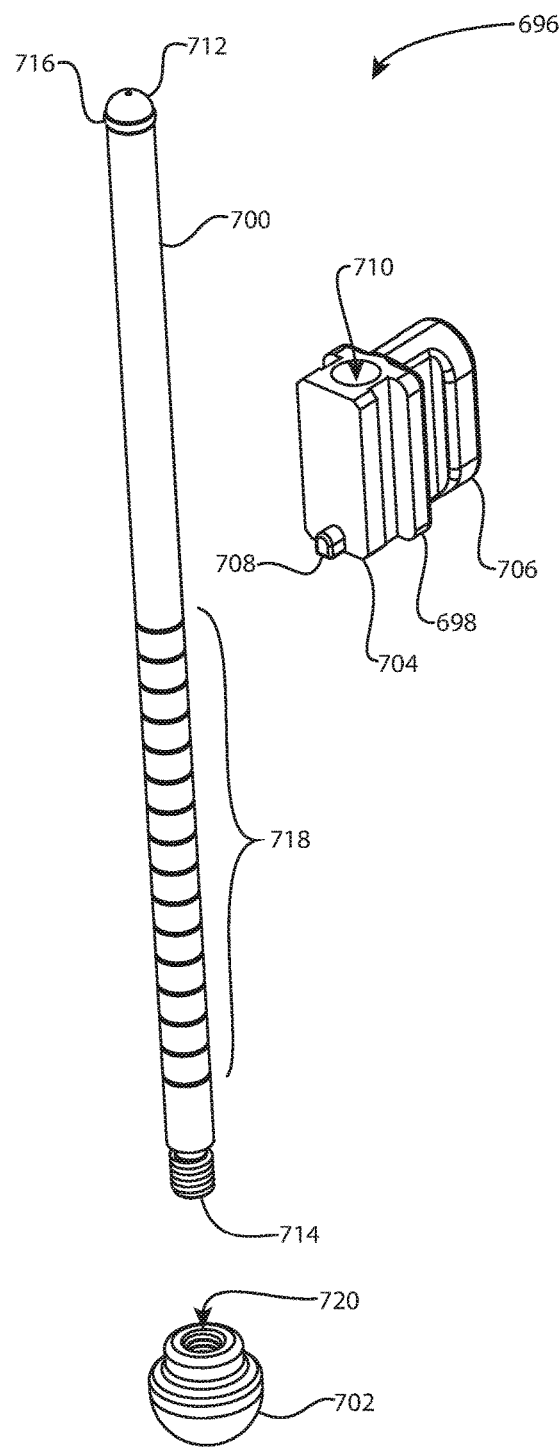
FIG. 58B is another exploded perspective view of the Whiteside's angle gage assembly of FIG. 58A from a different direction.

Referring to FIGS. 58A and 58B, a Whiteside's angle gage assembly 696 includes a body 698, a shaft 700, and a cap 702. The body 698 includes a proximal dovetail rail 704 and a distal dovetail rail 706. A tab 708 extends from one end of the proximal dovetail rail 704 (the upper or anterior end, in use). A hole 710 extends through the body 698. The dovetail rails 704, 706 and the hole 710 are all parallel. The shaft 700 is a cylindrical part with a rounded end 712 and an opposite end 714 terminating in a threaded portion. The rounded end 712 includes an external flange 716. Indicia 718 may be provided on the shaft 700, such as a millimeter or inch scale, or a scale relating to available implant sizes. The cap 702 includes a threaded socket 720 in one end.

The Whiteside's angle gage assembly 696 may be assembled as follows. The shaft 700 is inserted into the hole 710 so that the threaded end 714 protrudes next to the tab 708. The end 714 is threaded into the threaded socket 720.

The Whiteside's angle gage assembly 696 may be coupled to the angle block assembly 652 by sliding the proximal dovetail rail 704 into the dovetail channel 668 until the tab 708 is fully seated in the notch 670. With the clamp ring 672 loosened, the shaft 700 may be adjusted to align parallel with Whiteside's line of an intact distal femur 102. The clamp ring 672 may be tightened by turning the bolt 660 to lock the angle block 654 relative to the translation bar 656, thus saving the angle of the Whiteside's line for future use. More specifically, the dovetail channel 668 is locked parallel to the Whiteside's line. The indicia 718 may be read at this time, for example the anterior-posterior femoral dimension or femoral implant size.

Referring to FIGS. 59A and 59B, a cut guide mounting block assembly 722 includes a mounting block 724, a distal dovetail rail 726, a first screw 728, and a second screw 730.

Referring to FIG. 60, the mounting block 724 includes a proximal dovetail rail 732. A tab 734 extends from one end of the proximal dovetail rail 732 (the upper or anterior end, in use). A first plate 736 extends parallel to the proximal dovetail rail 732; in use, the first plate extends in the anterior-posterior and medial-lateral directions. A second plate 738 extends perpendicular to the first plate 736; in use, the second plate extends in the proximal-distal and medial-lateral directions. The proximal dovetail rail 732, first plate 736, and second plate 738 may be integrally formed as shown, or may be separate parts coupled together. A first hole 740 extends in the proximal-distal direction through the proximal dovetail rail 732. A second hole 742 extends parallel to the first hole 740 through the first plate 736.

The distal dovetail rail 726 includes a first hole 744 and a second hole 746. The holes 744, 746 are parallel and extend in the proximal-distal direction into a proximal surface 748 of the distal dovetail rail 726.

The cut guide mounting block assembly 722 may be assembled as follows. The proximal surface 748 of the distal dovetail rail 726 is placed against the distal aspect of the first plate 736. The holes 740, 744 are aligned and the holes 742, 746 are aligned. The first screw 728 is inserted through the hole 740 and threaded into the hole 744. The second screw 730 is inserted through the hole 742 and threaded into the hole 746.

The cut guide mounting block assembly 722 may be coupled to the angle block assembly 652 by sliding the proximal dovetail rail 732 into the dovetail channel 668 until the tab 734 is fully seated in the notch 670.

Figure 61A:
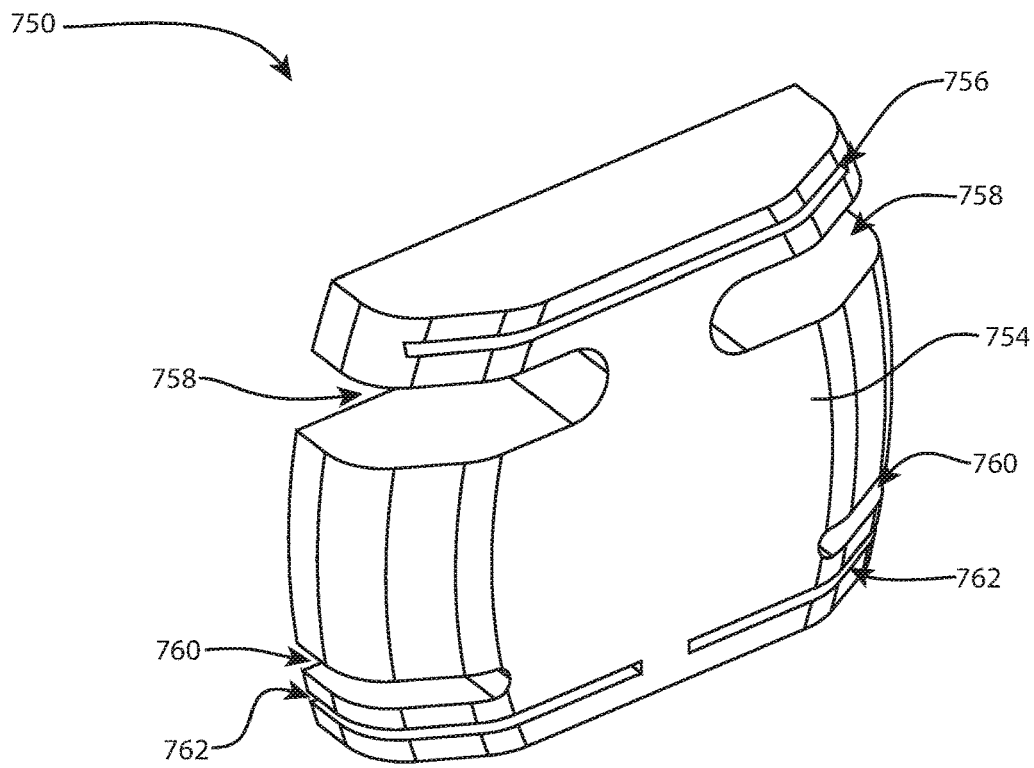
FIG. 61A is a perspective view of a four-in-one cut guide for use with the cut guide mounting block assembly of FIG. 59A.
Figure 61B:
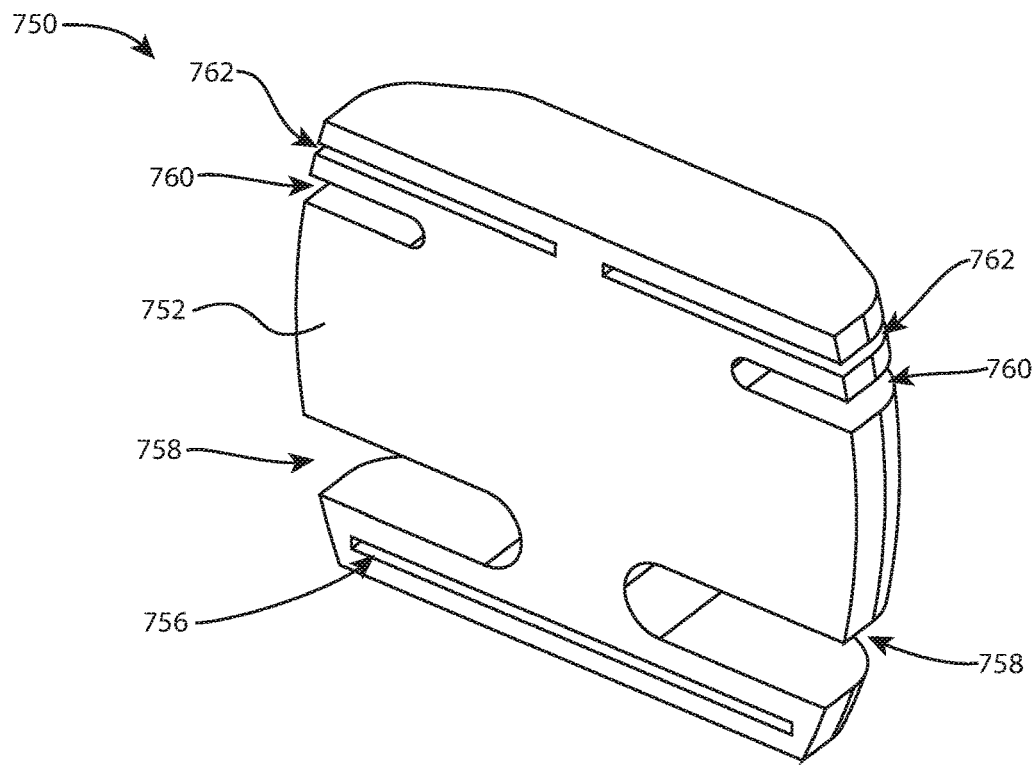
FIG. 61B is another perspective view of the four-in-one cut guide of FIG. 61A from a different direction.

Referring to FIGS. 61A and 61B, a four-in-one cut guide 750 is a generally rectangular plate with a proximal surface 752, an opposite distal surface 754, a first slot 756, a second slot 758, a third slot 760, and a fourth slot 762. Bilateral slots 758, bilateral slots 760, and bilateral slots 762 are shown. The slots 756, 762 may be the same width and may be narrower than the slots 758, 760. There may be just enough room to pass a saw blade through the slot 756 or the slot 762 to make an anterior femoral resection 214 or a posterior femoral resection 220, respectively. The slots 756, 762 may be said to define cutting paths of the saw blade acting through the slots. The slots 756, 762 may be referred to as saw slots or cut guide slots. The slot 760 may be narrower than the slot 758.

The four-in-one cut guide 750 may be coupled to the cut guide mounting block assembly 722 by inserting the second plate 738 through the slot 756 from distal to proximal.

Figure 62A:
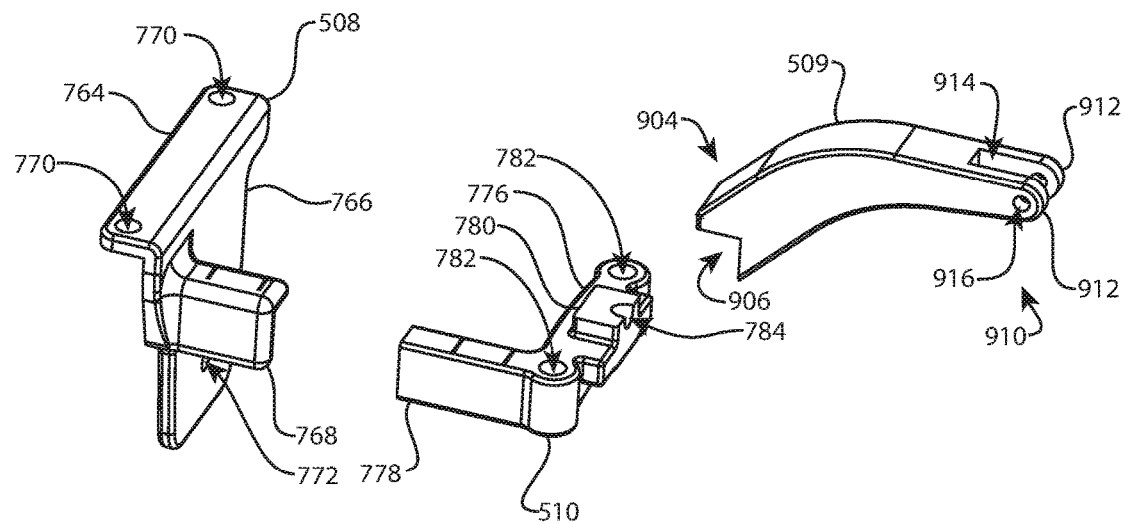
FIG. 62A is an exploded perspective view of a tibial connection block, a tibial pin guide, and a tibial riser of the instrument system of FIG. 47A.
Figure 62B:
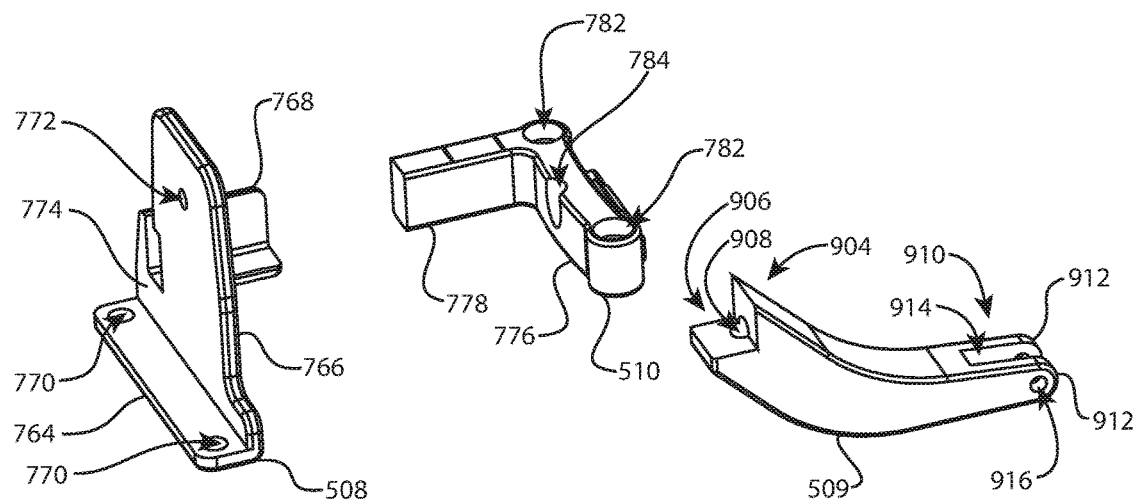
FIG. 62B is another exploded perspective view of the tibial connection block, pin guide, and riser of FIG. 62A from a different direction.
Figure 63A:
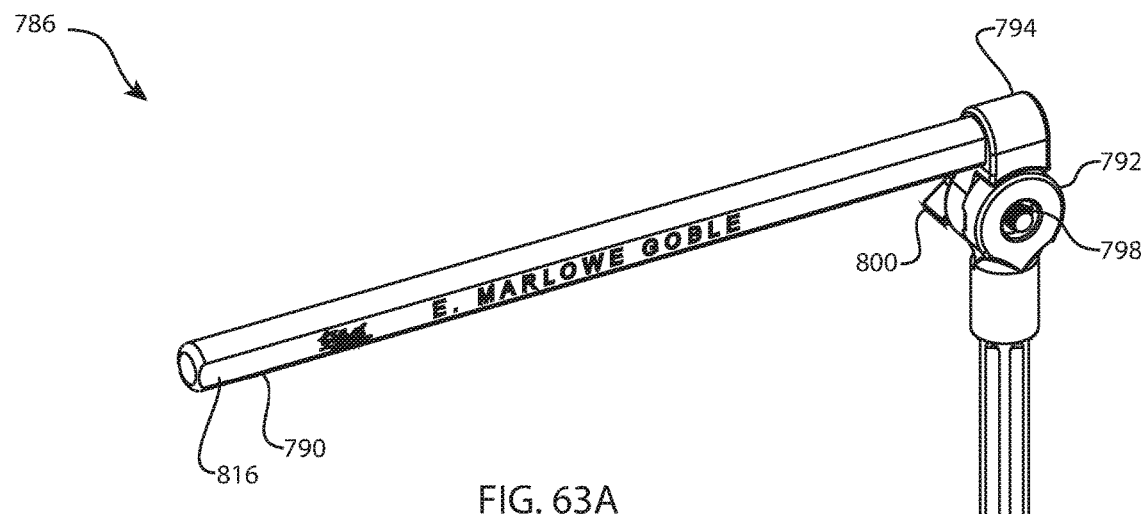
FIG. 63A is a perspective view of a femoral support arm assembly for use with the instrument system of FIG. 47A.
Figure 63B:
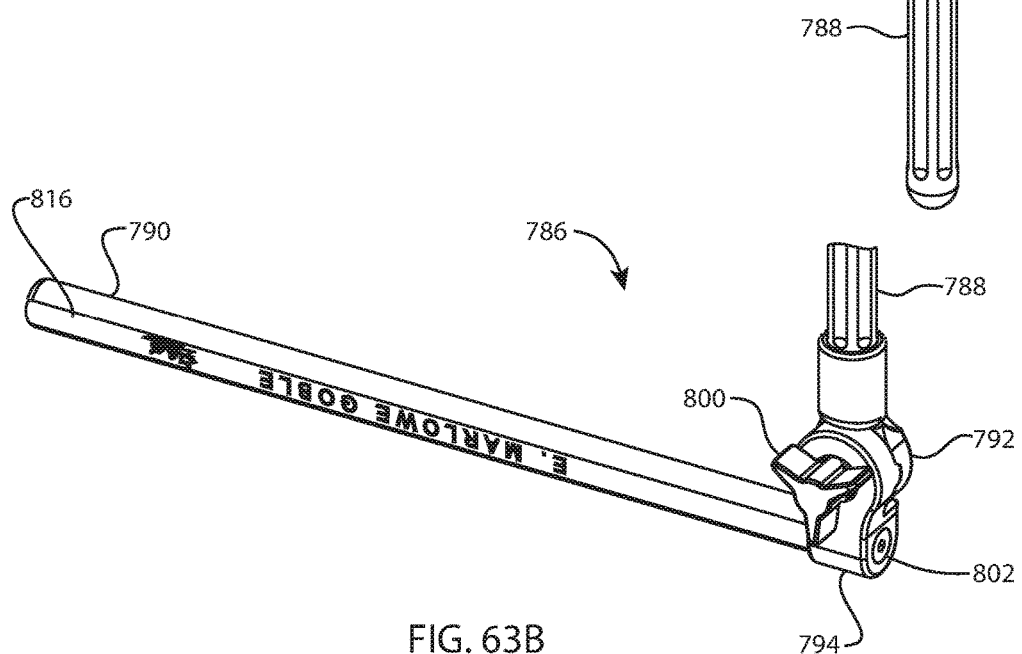
FIG. 63B is another perspective view of the femoral support arm assembly of FIG. 63A from a different direction.
Figure 64A:
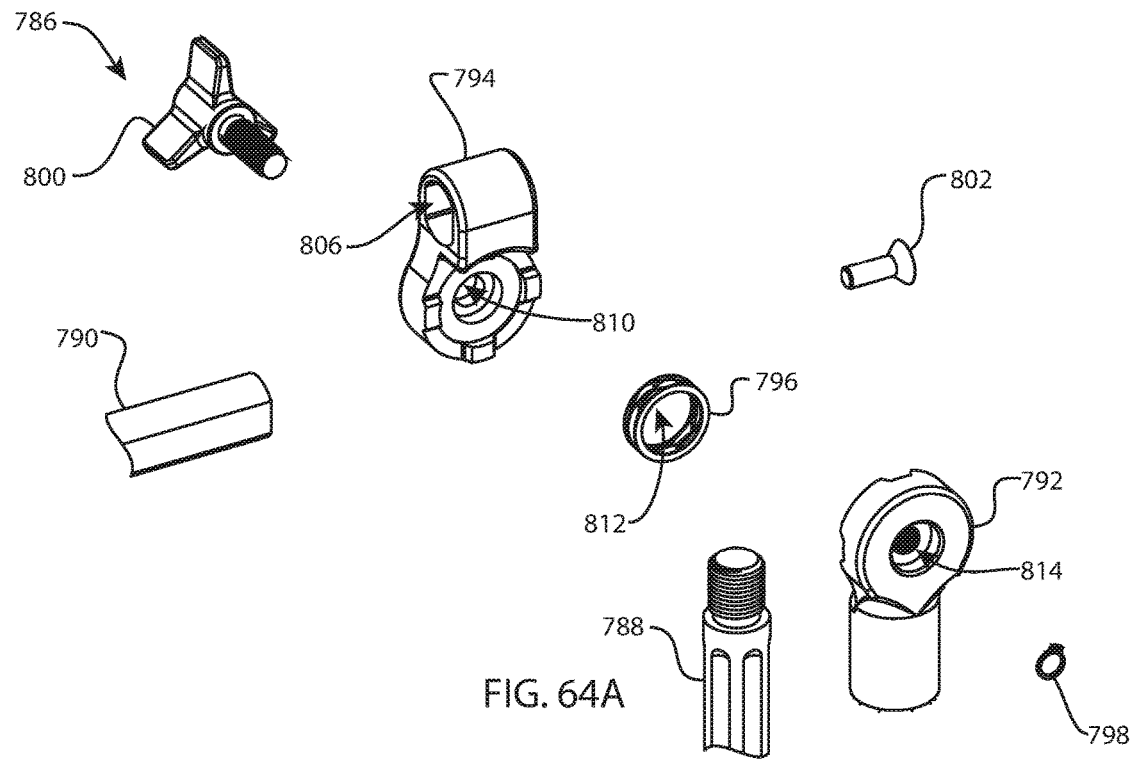
FIG. 64A is an exploded perspective view of the femoral support arm assembly of FIG. 63A.
Figure 64B:
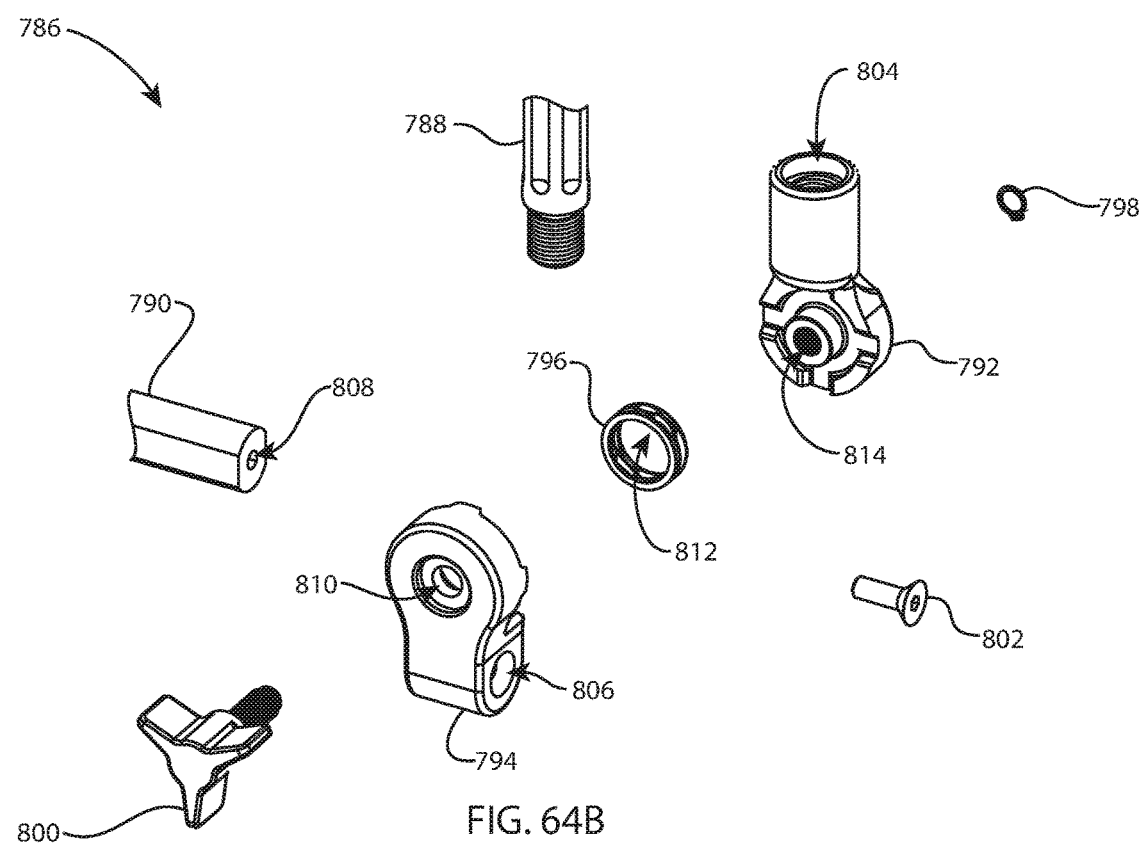
FIG. 64B is another exploded perspective view of the femoral support arm assembly of FIG. 64A from a different direction.
Figure 65A:
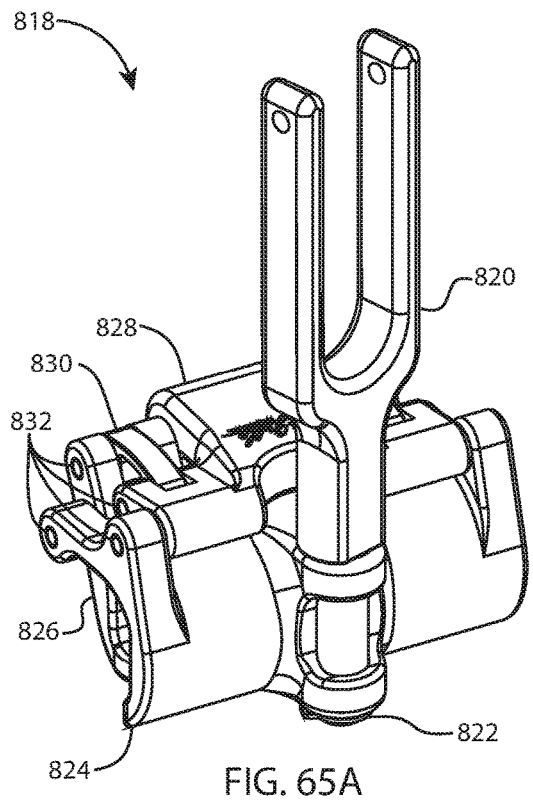
FIG. 65A is a perspective view of a target clamp assembly for use with the femoral support arm assembly of FIG. 63A.
Figure 65B:
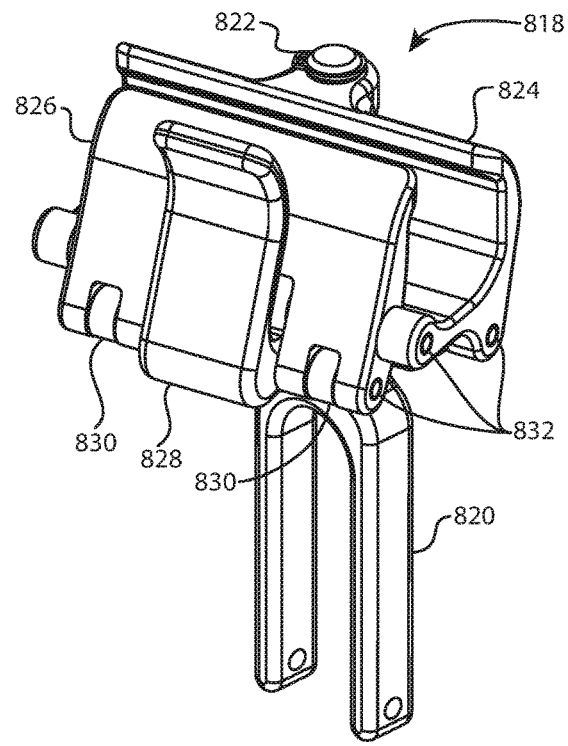
FIG. 65B is another perspective view of the target clamp assembly of FIG. 65A from a different direction.
Figure 65C:
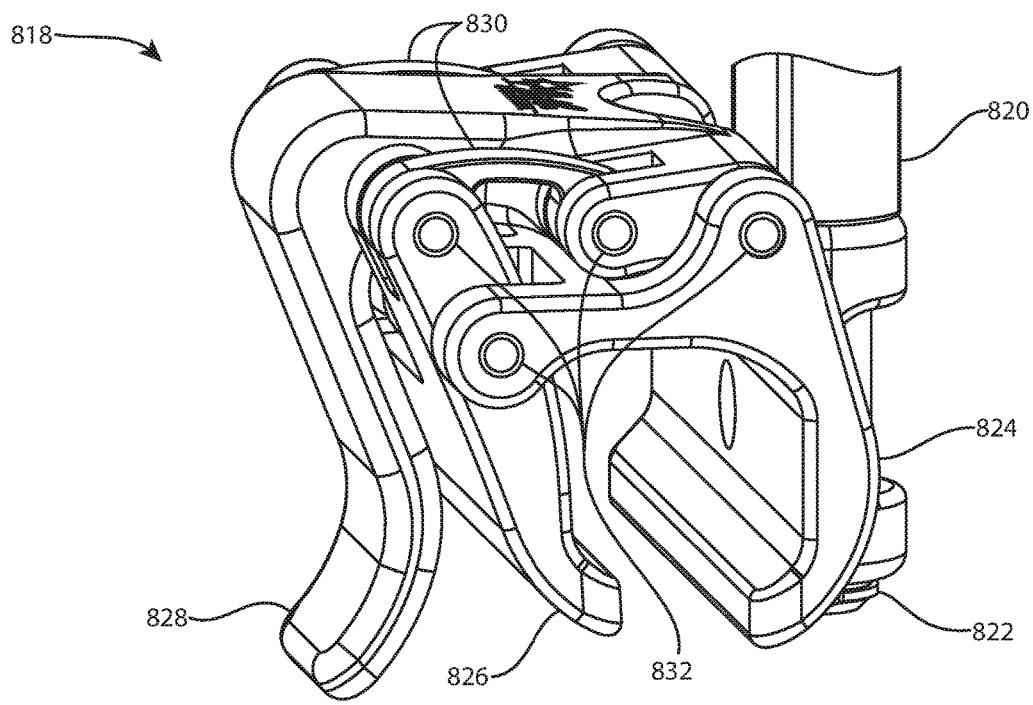
FIG. 65C is yet another perspective view of the target clamp assembly of FIG. 65A from another different direction.
Figure 66A:
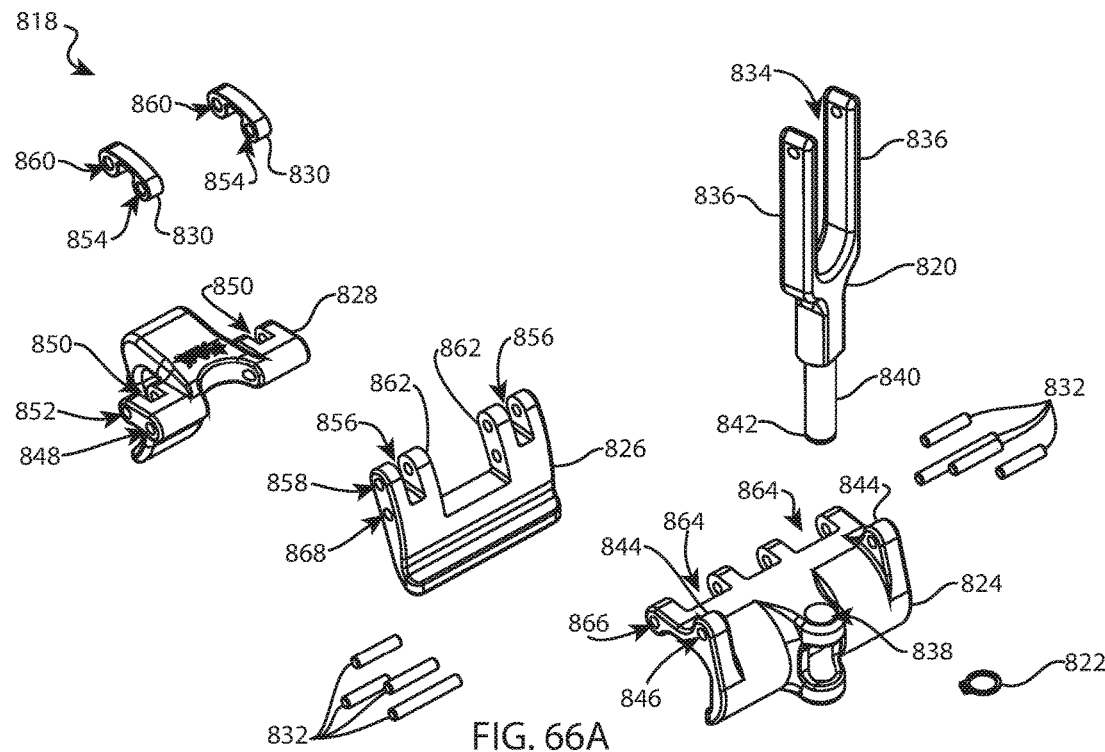
FIG. 66A is an exploded perspective view of the target clamp assembly of FIG. 65A.
Figure 66B:
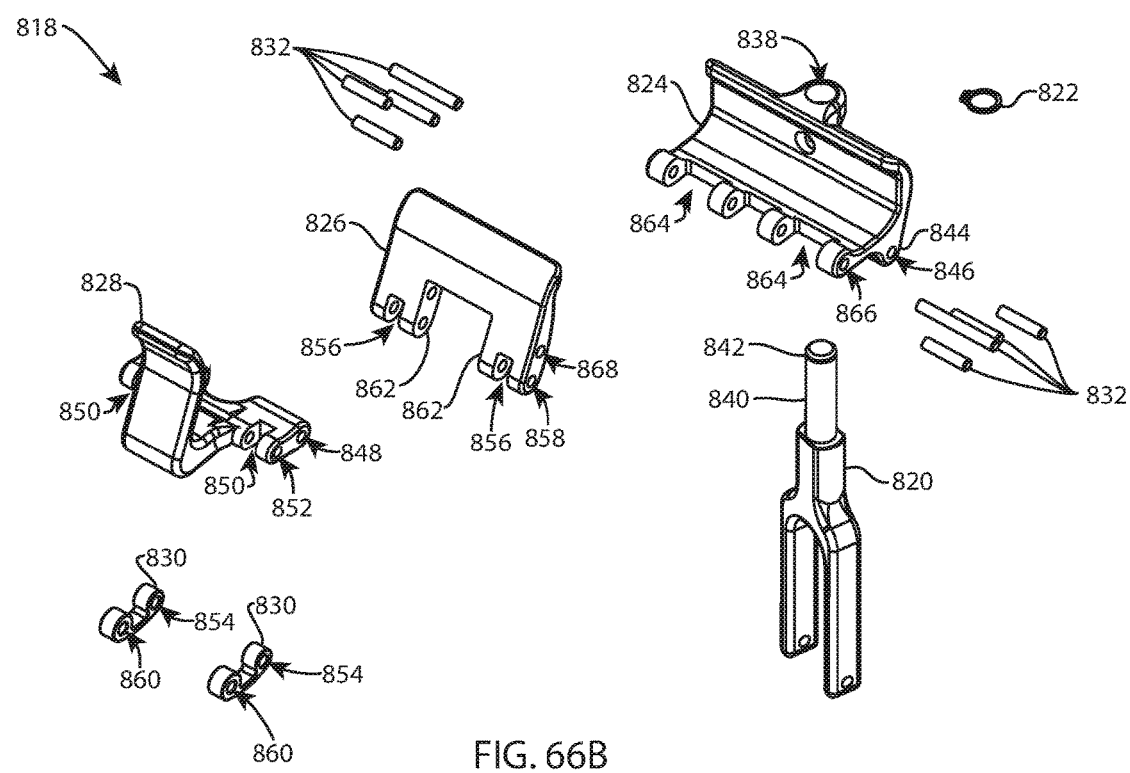
FIG. 66B is another exploded perspective view of the target clamp assembly of FIG. 66A from a different direction.
Figure 67A:
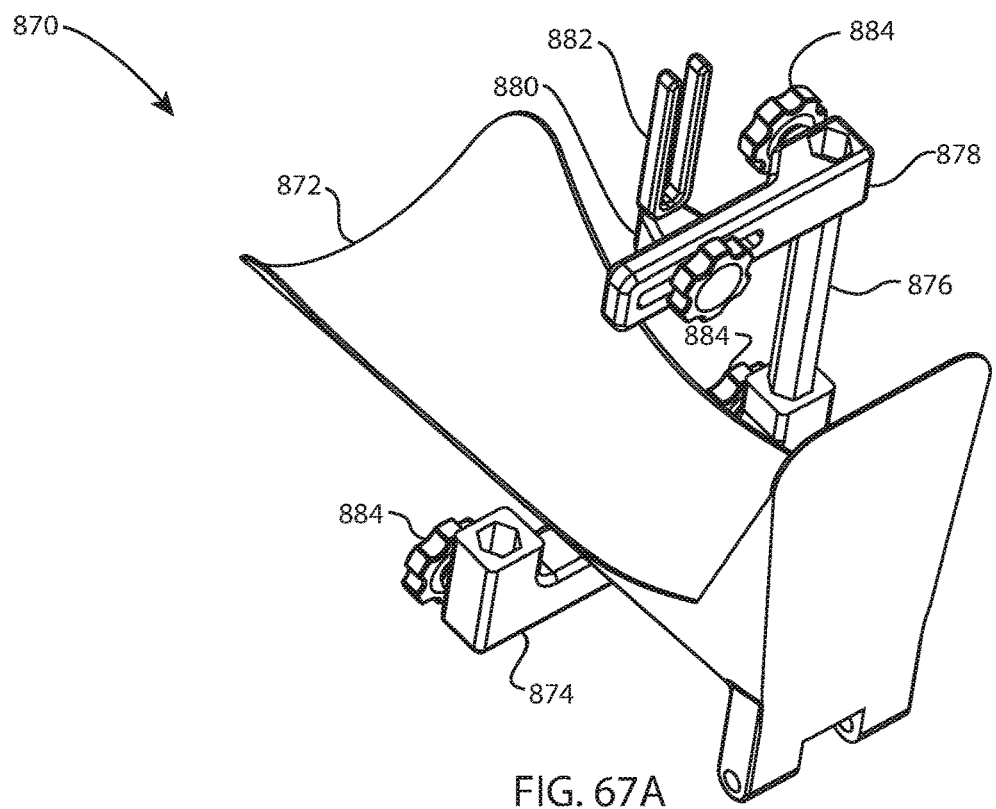
FIG. 67A is a perspective view of a foot holder assembly for use with the instrument system of FIG. 47A.
Figure 67B:
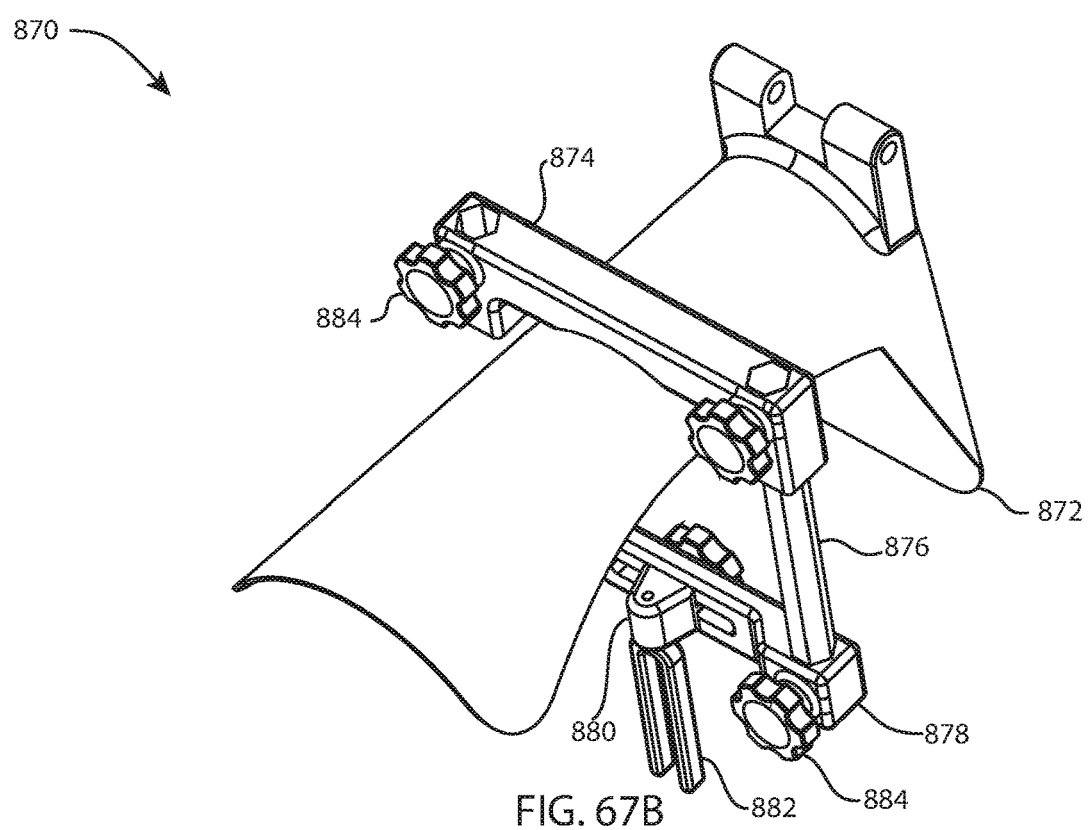
FIG. 67B is another perspective view of the foot holder assembly of FIG. 67A from a different direction.
Figure 68A:
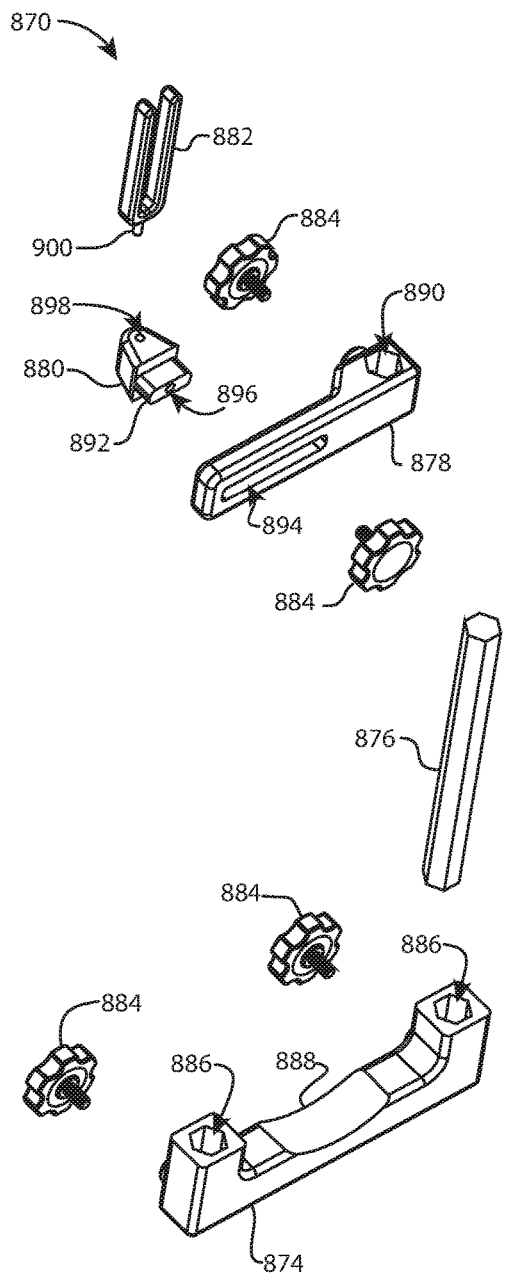
FIG. 68A is an exploded perspective view of the foot holder assembly of FIG. 67A, the foot holder omitted for clarity.
Figure 68B:
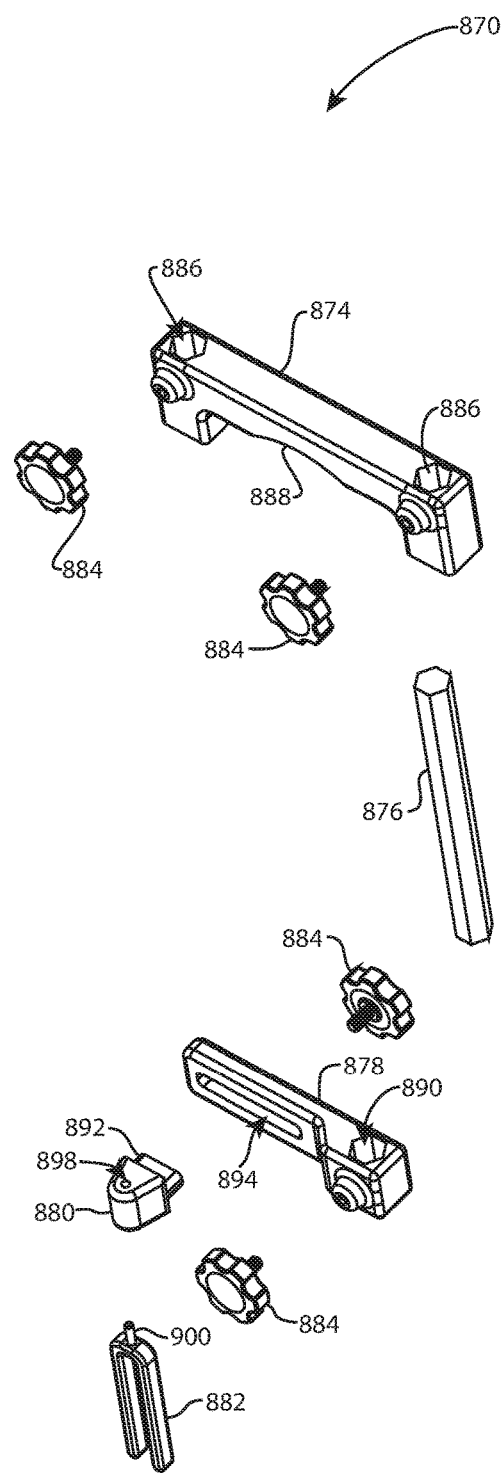
FIG. 68B is another exploded perspective view of the foot holder assembly of FIG. 68A from a different direction.

Referring to FIGS. 62A and 62B, the tibial connection block 508 includes a mounting plate 764, a second plate 766, and a distal protrusion 768. In use, the mounting plate 764 extends in the proximal-distal and medial-lateral directions. The second plate 766 extends perpendicular to the mounting plate 764 in the anterior-posterior and medial-lateral directions. The distal protrusion 768 extends distally from the second plate 766, and is adjacent to a medial or lateral side of the second plate. The mounting plate 764, second plate 766, and distal protrusion 768 may be integrally formed as shown, or may be separate parts coupled together. The distal protrusion 768 may form a right angle channel as shown, or may include a socket that opens distally, for example a square socket. Bilateral holes 770 extend in the anterior-posterior direction through the mounting plate 764. These holes 770 receive the same pegs 646 described previously for the distal femoral condyle block 638 (FIGS. 55A and 55B). Alternately, the pegs may be integrally formed with the mounting plate 764. A hole 772 extends in the proximal-distal direction through the second plate 766. This hole 772 may receive and stabilize a distractor jaw tip. The second plate 766 includes a proximal surface 774. The tibial connection block 508 may be analogous to a middle portion of the tibial-femoral pin guide 310.

The tibial connection block 508 releasably couples to the femoral riser 504. The pegs 646 fit into the mounting holes 584 so that the proximal surface 774 faces the distal portion 566.

The tibial pin guide 510 includes a bar 776, a proximal protrusion 778, and a distal boss 780. In use, the bar 776 extends in the medial-lateral direction, the proximal protrusion 778 extends proximally from one end of the bar 776, and the distal boss 780 extends distally from the center of the bar 776. The bar 776, proximal protrusion 778, and distal boss 780 may be integrally formed as shown, or may be separate parts coupled together. Bilateral holes 782 extend in the anterior-posterior direction through the bar 776. These holes 782 receive bone pins. A slanting hole 784 extends through the distal boss 780 from postero-proximal to antero-distal. The distal boss 780 is analogous to the boss 378 of the tibial-femoral pin guide 310 (FIGS. 28A-28B and the hole 784 is analogous to the hole 382.

Figure 28A:
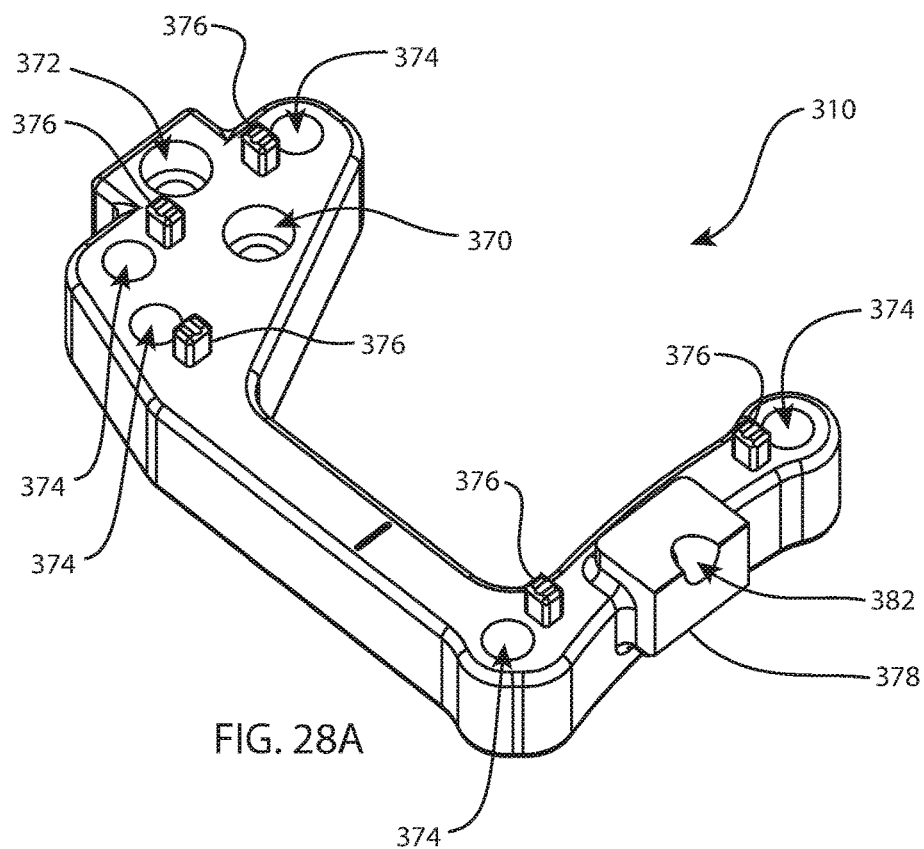
FIG. 28A is a perspective view of a tibial-femoral pin guide of the instrument system of FIG. 21A.
Figure 28B:
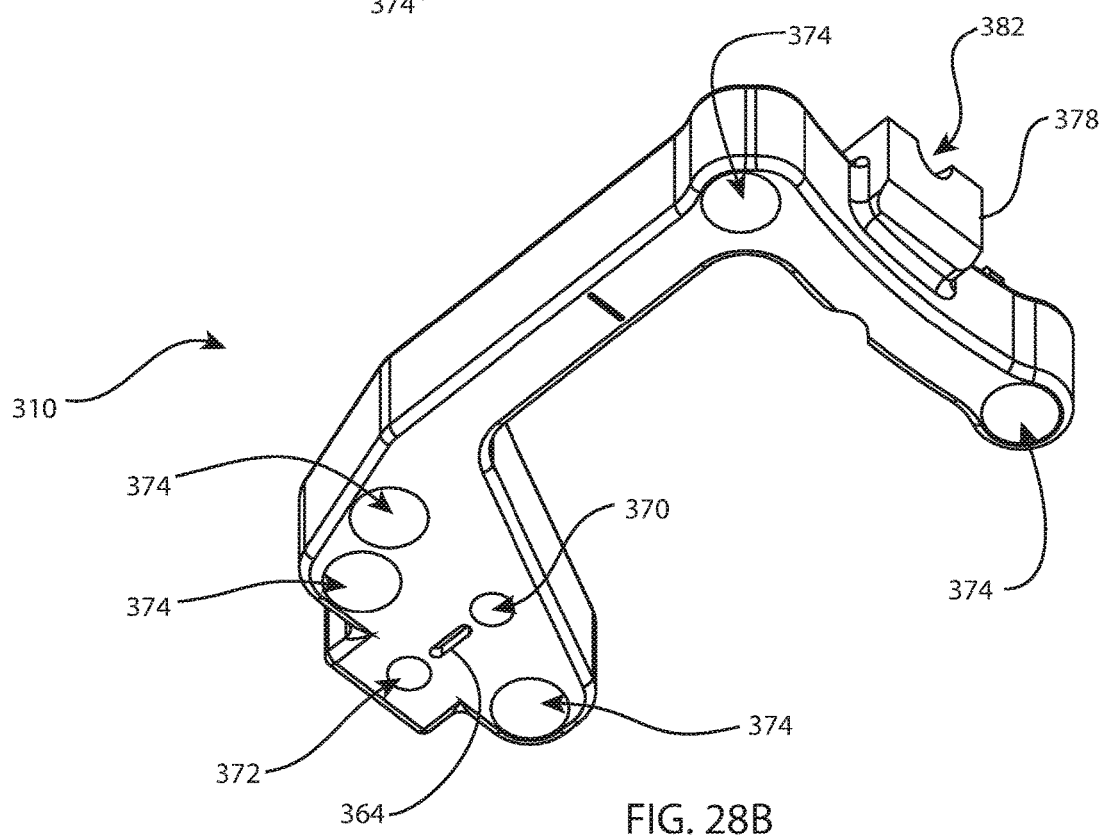
FIG. 28B is another perspective view of the tibial-femoral pin guide of FIG. 28A from a different direction.
Figure 29A:
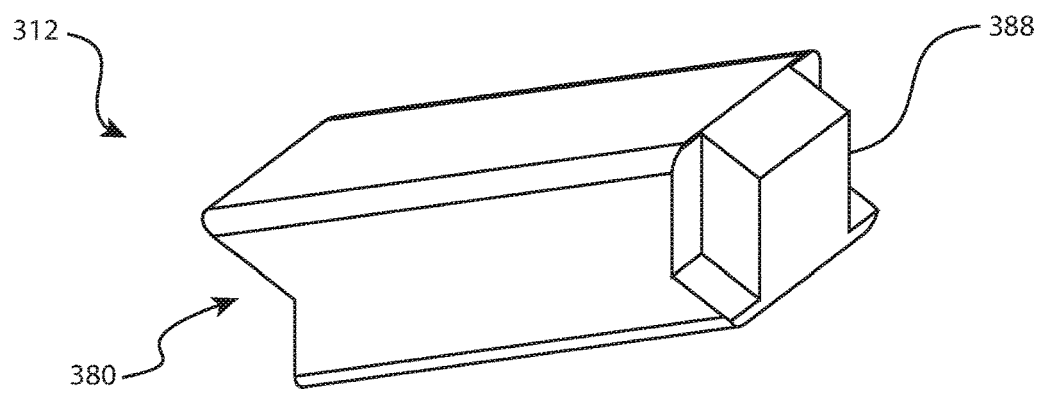
FIG. 29A is a perspective view of a tibial riser of the instrument system of FIG. 21A.
Figure 29B:
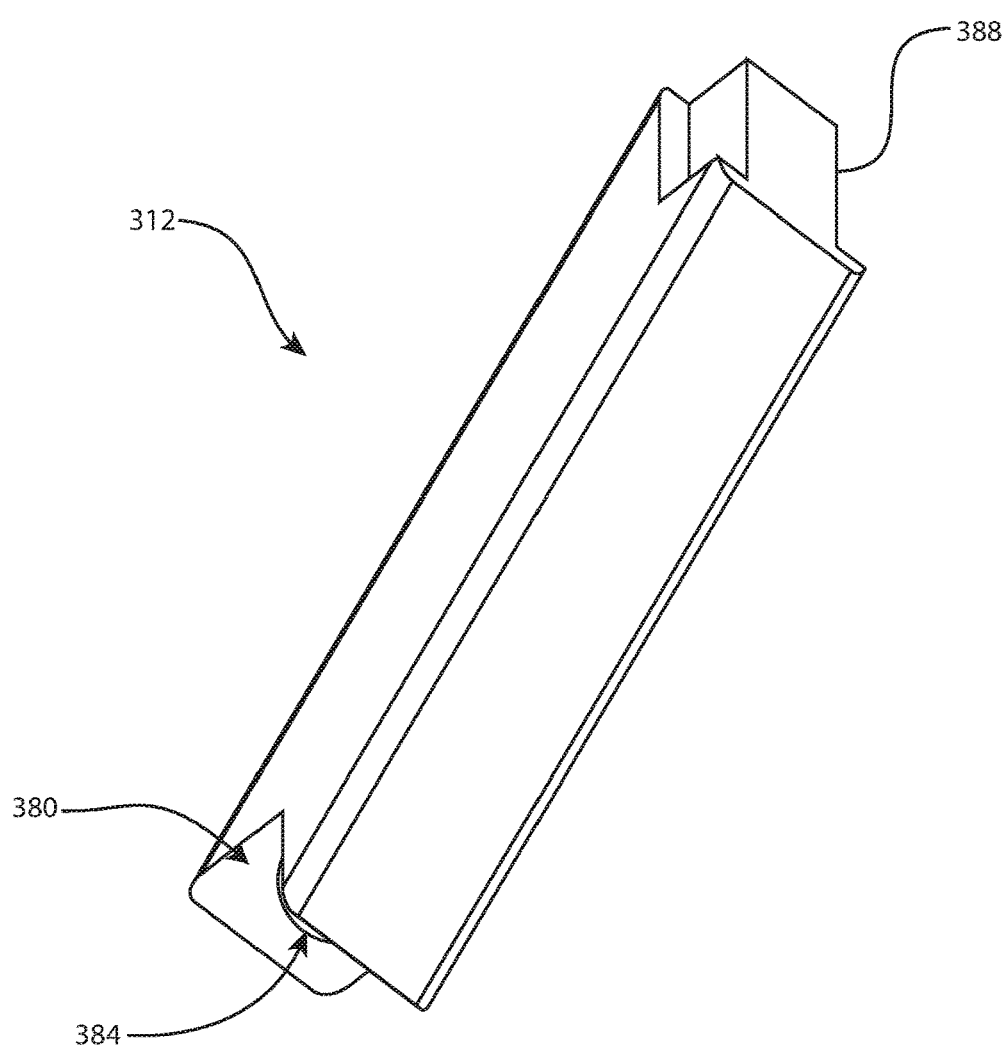
FIG. 29B is another perspective view of the tibial riser of FIG. 29A from a different direction.
Figures 31A, 31B:
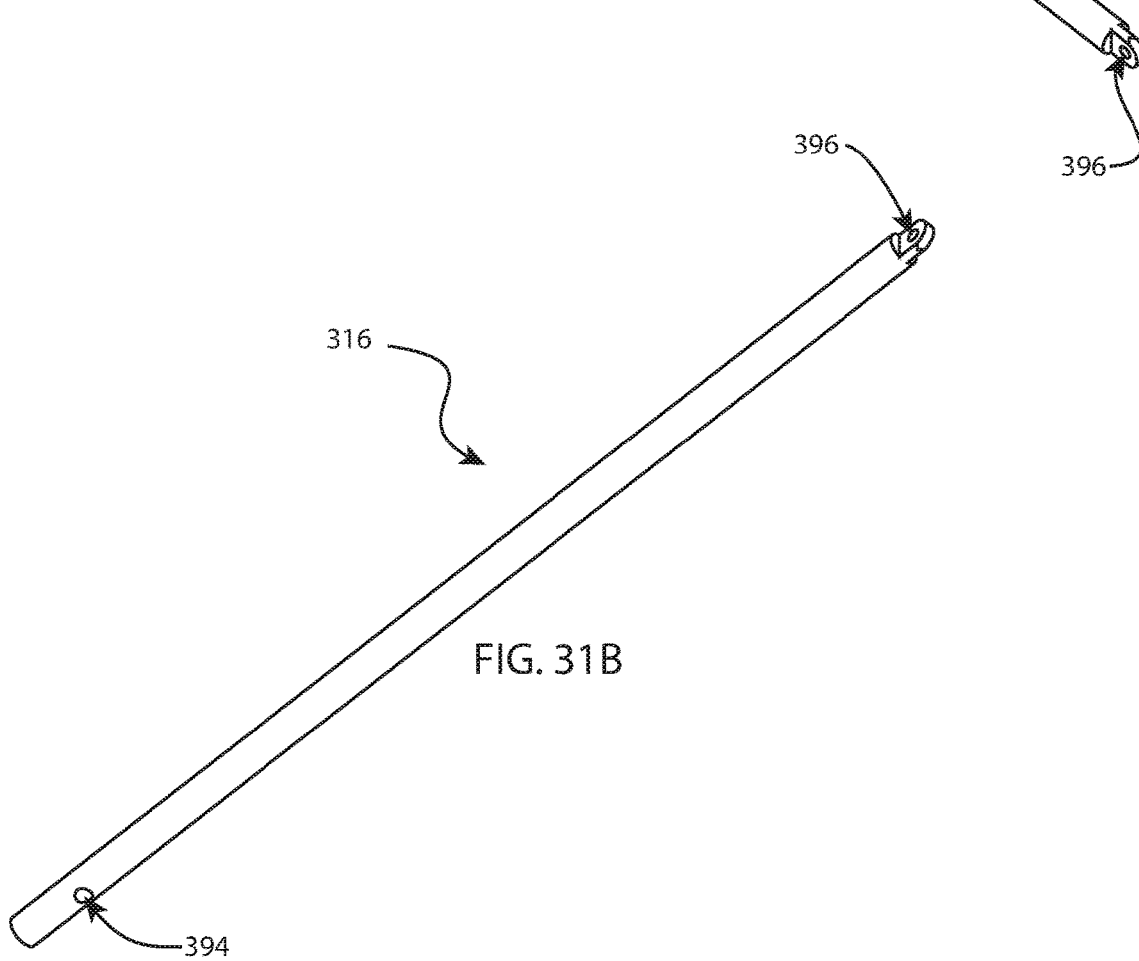
FIG. 31A is a perspective view of a first tibial inner extension rod of the instrument system of FIG. 21A.
FIG. 31B is another perspective view of the first tibial inner extension rod of FIG. 31A from a different direction.
Figure 32A:
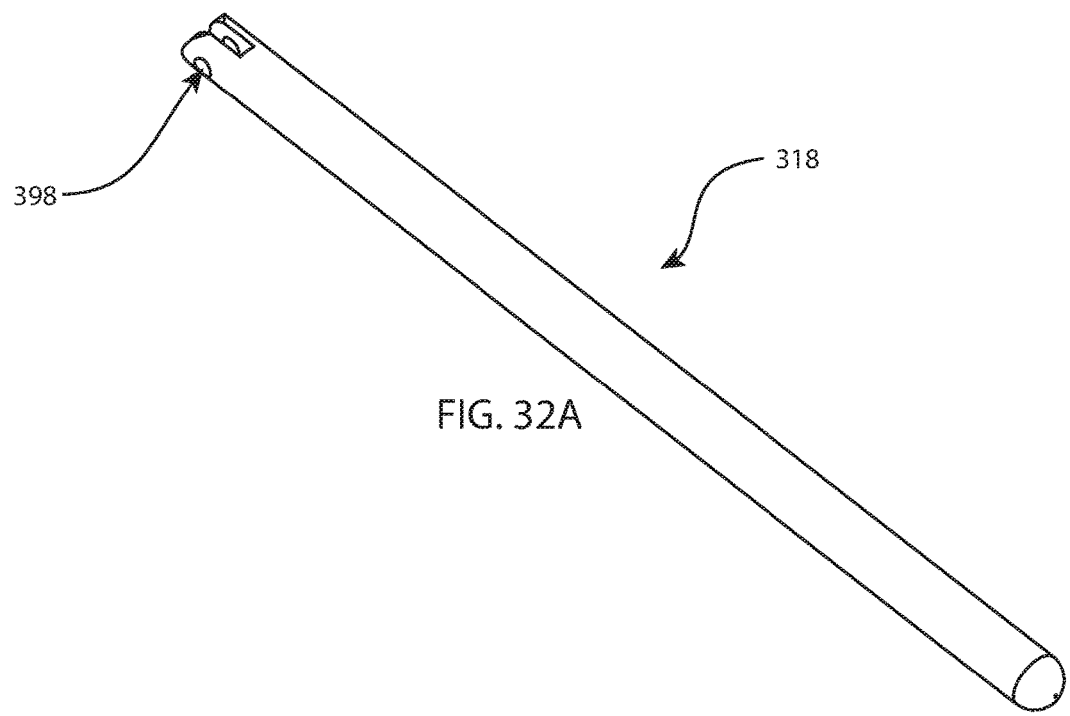
FIG. 32A is a perspective view of a second tibial inner extension rod of the instrument system of FIG. 21A.
Figure 32B:
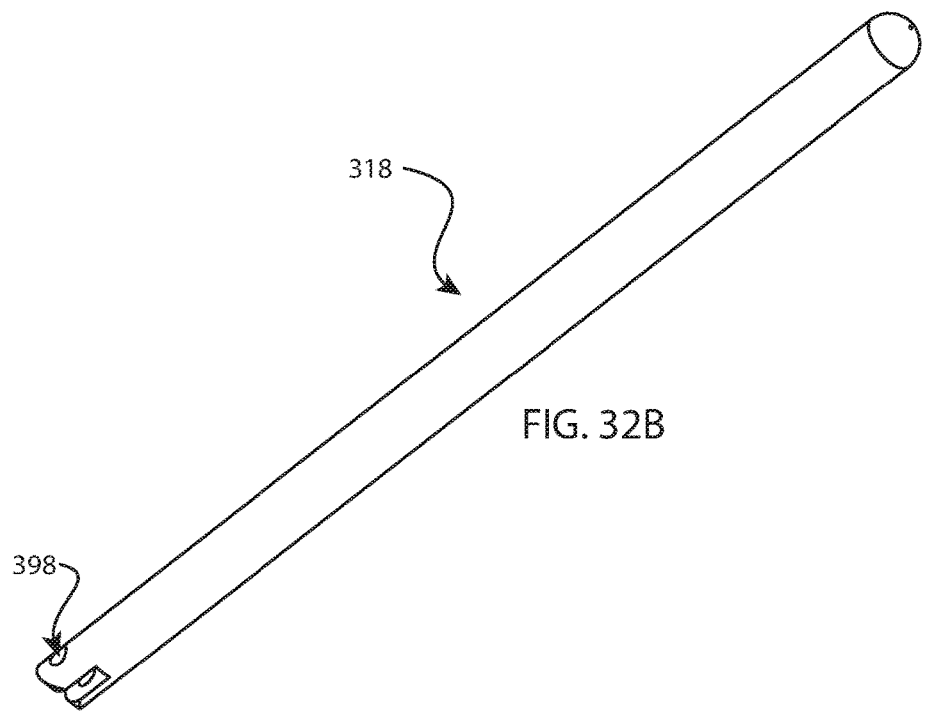
FIG. 32B is another perspective view of the second tibial inner extension rod of FIG. 32A from a different direction.

The tibial pin guide 510 may be coupled to the tibial connection block 508 by inserting the proximal protrusion 778 in the distal protrusion 768. Not shown, a fastener may extend through a slot in the distal protrusion and into a socket, such as a threaded hole, in the proximal protrusion so that the tibial pin guide 510 is lockably slidable in the proximal-distal direction relative to the tibial connection block 508. Referring to FIGS. 28A and 28B, the coupled tibial pin guide 510 and tibial connection block 508 may be analogous to the tibial-femoral pin guide 310.

The tibial pin guide 510 may be designed to couple to the angle block assembly 652 instead of the tibial connection block 508. The tibial pin guide 510 may be modified to include a dovetail rail, like the proximal dovetail rail 704 of the Whiteside's angle gage assembly 696 (FIGS. 58A and 58B), which couples to the dovetail channel 668 of the angle block assembly 652 (FIGS. 57A and 57B).

The tibial riser 509 includes a proximal end 904 with a notch 906 that is complementary to the distal boss 780 of the tibial pin guide 510 and a slanting hole 908 that extends into the first end 904 from postero-proximal to antero-distal. The tibial riser 509 includes a distal end 910 that is divided into two arms 912 separated by a slot 914. A transverse hole 916 extends through the arms 912 and across the slot 914.

The tibial riser 509 may be coupled to the tibial pin guide by abutting the distal boss 780 in the notch 906 so that the holes 784, 908 are aligned, and inserting a fastener through the holes. Alternately, the tibial riser 509 and the tibial pin guide 510 may be integrally formed as a single part. The tibial pin guide 510 may be coupled to the tibial riser 312 (FIGS. 29A and 29B) (with attached tibial extension rod 313) by inserting distal boss 780 into notch 380 and inserting a fastener through holes 784, 384. Alternately, the tibial riser 312 may be permanently rigidly coupled to the tibial pin guide 510.

The tibial extension rod 511 may be identical to the femoral extension rod 506 (FIGS. 54A and 54B), and is shown this way in this application. More specifically, the illustrated tibial extension rod 511 includes the outer extension rod 604, the inner extension rod 606, the spool 608, the sleeve 610, the ring 612, and the retaining ring 614, which are assembled and function as described previously for the femoral extension rod 506.

The assembled tibial extension rod 511 may be coupled to the tibial riser 509 by inserting the end of the inner extension rod 606 with the hole 624 into the slot 914, aligning the hole 602 with the hole 916, and inserting a fastener through the holes 602, 916 to form a hinge 917 (FIGS. 47B and 49B). The tibial extension rod 511 is free to pivot about the hinge 917. In use, the tibial extension rod 511 pivots in an anterior-posterior direction which is generally parallel to the sagittal plane. The tibial extension rod 511 is constrained against pivoting in a medial-lateral direction which is generally parallel to the coronal plane. The end of the inner extension rod 606 with the hole 624 is the proximal end of the tibial extension rod 511, and the end of the outer extension rod 604 with the retaining ring 614 is the distal end of the tibial extension rod 511.

Referring to FIGS. 63A-64B, a femoral support arm assembly 786 includes a post 788, a bar 790, a first clamp body 792, a second clamp body 794, a spring 796, a retaining ring 798, a thumbscrew 800, and a screw 802. The post 788 threads into a socket 804 of the first clamp body 792. The bar 790 is inserted into a socket 806 of the second clamp body 794 and the screw 802 is threaded into a hole 808 of the bar to fix the bar 790 in the socket 806. The spring 796 is sandwiched between the first and second clamp bodies 792, 794. The thumbscrew 800 is inserted through a hole 810 through the second clamp body 794 and a passageway 812 through the spring 796, and threaded into a hole 814 through the first clamp body 794. The retaining ring 798 fits around the threaded tip of the thumbscrew 800 to prevent unintentional disassembly of the thumbscrew 800, second clamp body 794, spring 796, and first clamp body 794. When the thumbscrew 800 is tightened, the bar 790 is held in a fixed orientation relative to the post 788. When the thumbscrew 800 is loosened, the bar 790 may be rotated relative to the post 788 about the threaded shaft of the thumbscrew. The post 788 may be clamped to an operating table. The bar 790 may include bilateral flats 816 that extend the length of the post 788. While the femoral support arm assembly 786 is presented in the context of supporting the target clamp assembly 818 discussed next, it also has utility as a tool holder in the immediate operative site, when outfitted with clamp-on tool holders.

Referring to FIGS. 86A and 86B, a femoral head finder 918 is a T-shaped part with a body 920 and a stem 922. The body 920 forms the crossbar of the T-shape and the stem 922 forms the upright of the T-shape. The body 920 includes a deep groove or channel 924 that extends along the length of the body 920 so that the body is open along its bottom side.

The femoral head finder 918 may be coupled to the bar 790 of the femoral support arm assembly 786; the bar 790 is received in the channel 924. Note that the channel 924 has flat interior sides that are complementary to the flats 816 of the bar 790 so that the femoral head finder 918 does not rotate about the bar 790.

Referring to FIGS. 87A and 87B, a collar 926 is a ring with a radial hole 928 through a side wall of the ring. The hole 928 may be threaded to receive a set screw (not shown). The collar 926 may be coupled to the bar 790; the bar 790 is received in the collar 926. The set screw may be tightened in the hole 928 to lock the collar 926 to the bar 790.

Referring to FIGS. 65A-66B, a target clamp assembly 818 includes a target 820, a retaining ring 822, a first clamp body 824, a second clamp body 826, a lever 828, a link 830, and a pin 832. The example shows two links 830 and eight pins 832. The target 820 includes a slot 834 formed between a pair of uprights 836. The target may be called a goalpost or tuning fork. A ring, reticle, cross hairs, or the like may substitute for the goalpost design. The link 830 is preferably compliant or elastic.

A hole 838 of the first clamp body 824 receives a post 840 of the target 820; the retaining ring 822 engages a circumferential external groove 842 around the tip of the post 836 to prevent unintended disassembly of the first clamp body 824 and the target 820. The lever 828 is positioned between arms 844 of the first clamp body 824 so that hole 846 aligns with hole 848. A pin 832 is inserted into holes 846, 848 from each side of the first clamp body 824. Links 830 are positioned in notches 850 of the lever 828 so that holes 852 align with holes 854. A pin 832 is inserted into holes 852, 854 from each side of the lever 828. The links 830 are positioned in notches 856 of the second clamp body 826 so that holes 858 align with holes 860. A pin 832 is inserted into holes 858, 860 from each side of the second clamp body 826. Tabs 862 of the second clamp body 826 are positioned in notches 864 of the first clamp body 824 so that holes 866 align with holes 868. A pin 832 is inserted into holes 866, 868 from each side of the first clamp body 824. Preferably, a width of the first clamp body 824, in the direction of the holes 846, 866, is equal to the length of the body 920 of the femoral head finder 918.

The target clamp assembly 818 couples to the bar 790 of the femoral support arm assembly 786. With the lever 828 lifted so that the first and second clamp bodies 824, 826 are open, the bar 790 is received between the first and second clamp bodies. The lever 828 is lowered to urge the first and second clamp bodies 824, 826 against the bar 790. The links 830 are preferably compliant, elastic, or resilient, and may function as extension springs in the target clamp assembly 818.

While the target clamp assembly 818 is shown with a captive target 820, alternative clamp assemblies are contemplated that have other functional structures besides the target 820, for example replacing the target with a universal receiver for various tools.

Referring to FIGS. 67A-68B, a foot holder assembly 870 includes a foot holder 872, a lower bar 874, a post 876, an upper bar 878, a target mounting block 880, a target 882, and a thumbscrew 884. Four thumbscrews are included in the example shown. The post 876 may be received in either one of the bilateral sockets 886 in the lower bar 874 and fixed in place with a thumbscrew. The foot holder 872, which may be called a boot, rests in a concave portion 888 of the lower bar 874, and may be coupled to the lower bar 874 temporarily or permanently. The lower bar 874 may be coupled to the foot holder 872 anywhere along the proximal-distal length of the foot holder. The post 876 is also received in a hole 890 in the upper bar 878 and fixed in place with a thumbscrew 884. The post 876, sockets 886, and hole 890 are all hexagonal in this example, although other non-circular or circular shapes are contemplated. The target mounting block 880 includes a tab 892 which is received in an elongated slot 894 through the upper bar 878. The tab 892 includes a hole 896 into which a thumbscrew 884 threads to fix the target mounting block 880 in place during use. The target mounting block 880 includes another hole 898 which receives a post 900 of the target. The upper bar 878, target mounting block 880, target 882, and associated thumbscrew 884 may be replaced by the bar 790 (FIGS. 63A-64B) and target clamp assembly 818. More than one lower bar 874 may be coupled to the foot holder 872 simultaneously, in which case each lower bar 874 may have an associated post 876, upper bar 878, target mounting block 880, target 882, and thumbscrews 884; or bar 790 and target clamp assembly 818.

Methods of using the instrument system 500 will now be described with reference to FIGS. 69-85.

Figure 69:
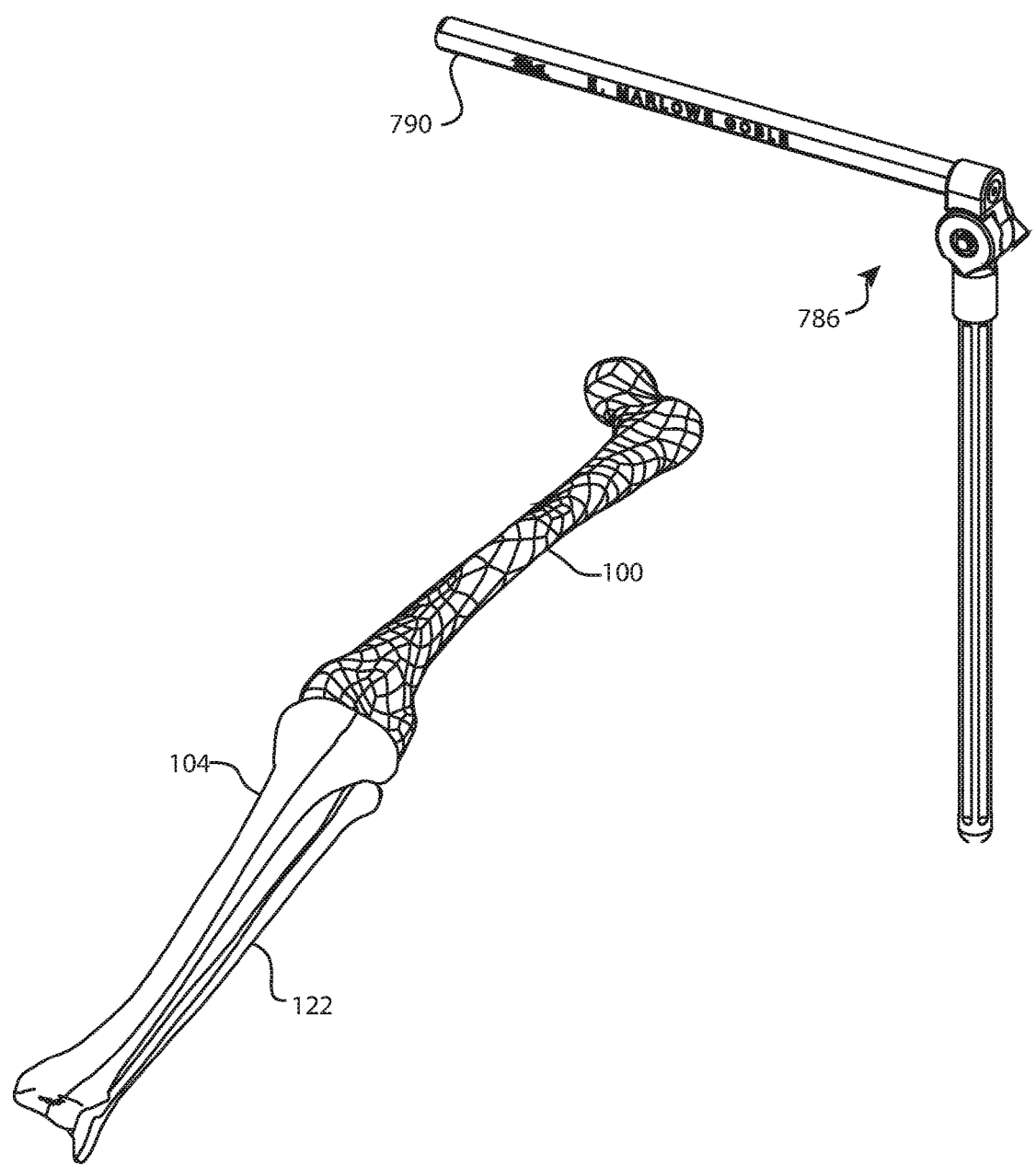
FIG. 69 is a perspective view of a femur, tibia, and fibula, showing the femoral support arm assembly of FIG. 63A.

Referring to FIG. 69, the femur 100, tibia 104, and fibula 122 are shown with the knee in full extension to represent a patient lying on an operating table during preparations for surgery. The femoral support arm assembly 786 is shown in position relative to the patient's leg, and may be clamped to the operating table in this position before being draped. The bar 790 extends horizontally over the patient's pelvis.

Figure 70:
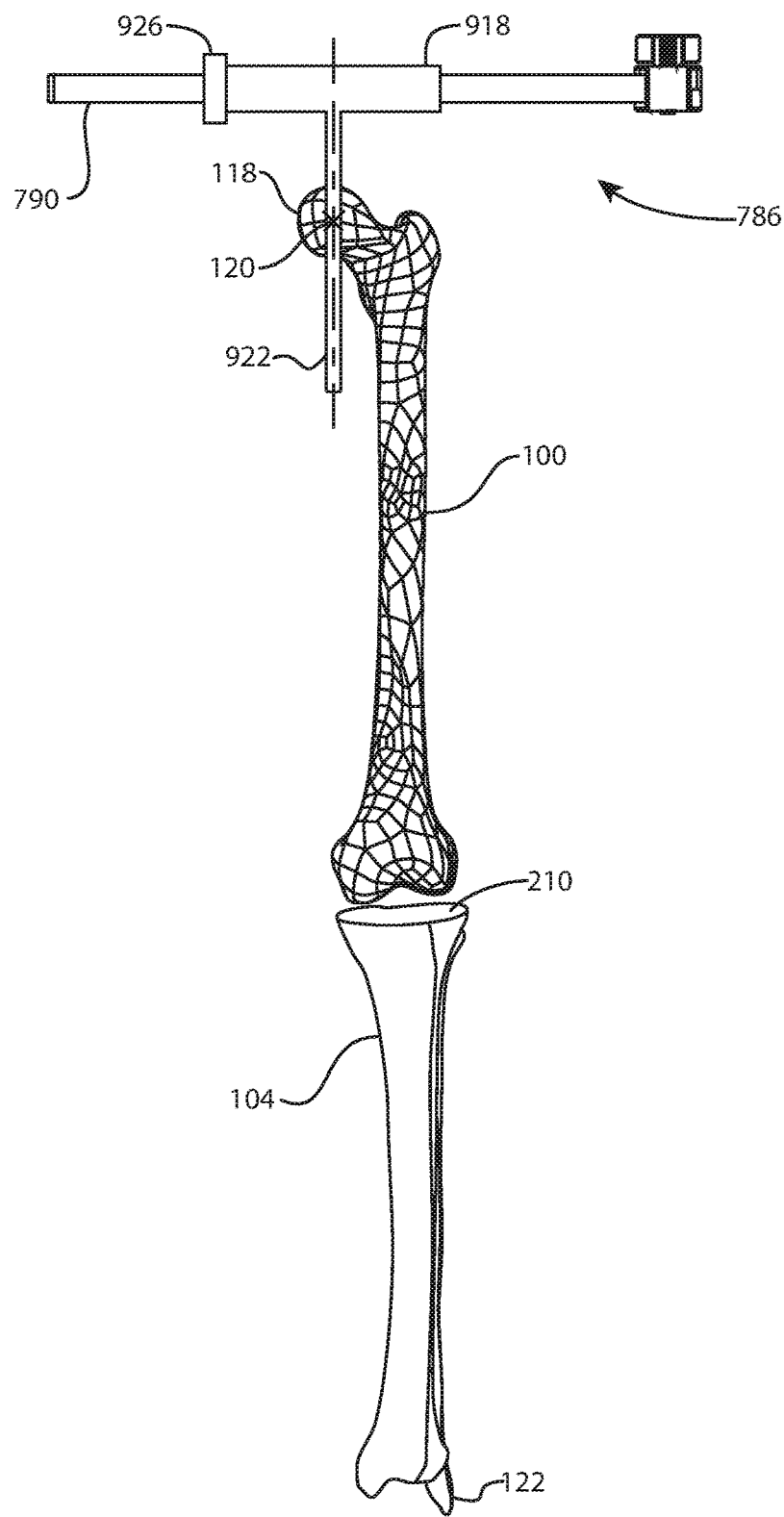
FIG. 70 is a perspective view of the femur, tibia, fibula, and femoral support arm assembly of FIG. 69 after performing a provisional proximal tibial resection.

Referring to FIG. 70, the femoral support arm assembly 786 may be positioned proximal (or distal) to the femoral head 118 so that the femoral head is exposed for radiographic or fluoroscopic imaging. Alternatively, the femoral support arm assembly 786 may be positioned directly over the center 120 of the femoral head 118, particularly if the bar 790 is radiolucent. The femoral head finder 918 has been coupled to the bar 790 and positioned along the bar so that the stem 922 extends over the center 120 of the femoral head 118. Radiographs, fluoroscopy, a C-arm, or other imaging may be used to verify that the stem 922 extends over the center 120 of the femoral head 118. The collar 926 has also been coupled to the bar 790 and positioned abutting the femoral head finder 918. After the stem 922 is positioned over the center 120 of the femoral head 118, the collar 926 may be locked to the bar 790. The femoral head finder 918 may then be removed from the bar 790. These steps shown in FIG. 70 are preferably performed before the patient is sterile draped and before the tourniquet is tightened. FIG. 70 also shows that a provisional tibial resection 210 has been made. The provisional tibial resection 210 may be made with the knee in full extension or in flexion. This step shown in FIG. 70 is performed after the patient is sterile draped and after the tourniquet is tightened.

Figure 71:
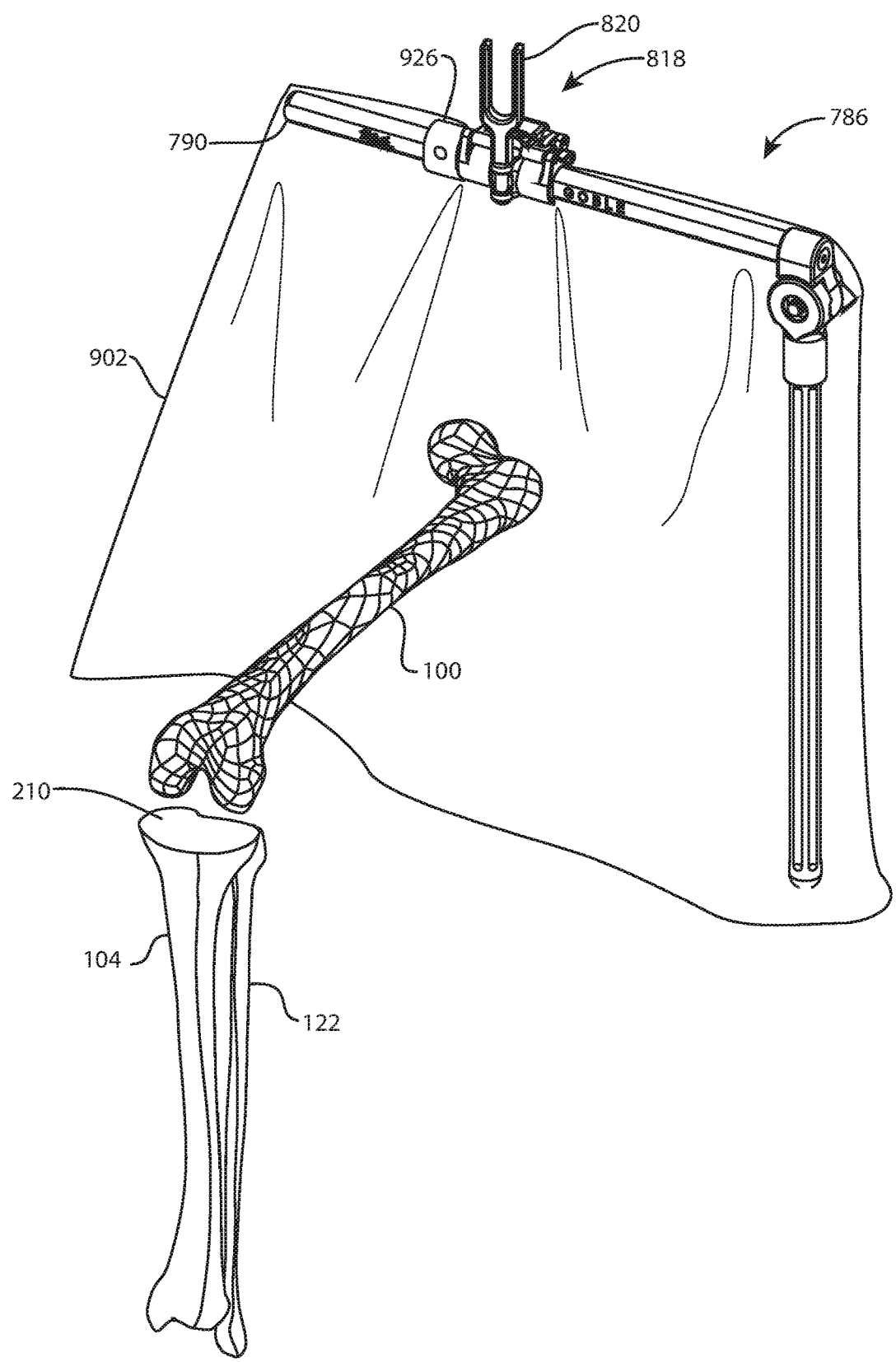
FIG. 71 is a perspective view of the femur, tibia, fibula, and femoral support arm assembly of FIG. 70, after coupling the target clamp assembly of FIG. 65A to the femoral support arm assembly.

Referring to FIG. 71, the target clamp assembly 818 has been coupled to the bar 790 of the femoral support arm assembly 786. Advantageously, this can occur after the femoral support arm assembly 786 has been covered with a drape 902, which is depicted as being sheer so that the femoral support arm assembly can be seen. The compliant, elastic, or resilient links 830 adjust to accommodate the thickness of the drape 902. The target 820 may be positioned proximal (or distal) to the femoral head 118, or directly over the center 120 of the femoral head, particularly if the target 820 is radiolucent. In this application, a target may be "over the center of the femoral head" even if the target is actually superior or inferior to the femoral head, so long as the femoral extension rod passes over the center of the femoral head when the femoral extension rod is aimed at the target. The target clamp assembly 818 has been coupled to the bar 790 directly adjacent to the collar 926. The bar 790 and the collar 926 are non-sterile and beneath the drape 902, while the target clamp assembly 818 is sterile and above the drape 902. This detail is noteworthy because the center 120 of the femoral head 118 may be objectively and precisely found in the non-sterile pre-operative phase, and transferred to the sterile operative phase by feeling the collar 926 through the sterile drape and positioning the target clamp assembly 818 next to the collar 926.

Referring to FIGS. 72A and 72B, the base 502 and femoral riser 504 have been coupled together for a left knee. The distal femoral condyle block 638 and the femoral extension rod 506 have been coupled to the femoral riser 504. The base 502 is being positioned against the anterior distal femur 102 and centered in the medial-lateral width of the distal femur 102, the paddle 642 is against the medial distal femoral condyle, and the femoral extension rod 506 is being aligned with the mechanical axis 202 of the leg (at least where it crosses the femur 100). The spool 608 is in the target 820.

Optionally, the angle block assembly 652 and the Whiteside's angle gage assembly 696 may be used during this step to assist in centering the femoral riser 504 and base 502 in the medial-lateral width of the distal femur 102, optionally using a narrow distal femoral condyle block 638, or a distal femoral condyle block that couples to the Whiteside's angle gage assembly 696. The angle block assembly 652 may be coupled to the femoral riser 504 and the Whiteside's angle gage assembly 696 may be coupled to the angle block assembly 652, with the shaft 700 of the Whiteside's angle gage assembly 696 extending within the intercondylar notch (trochlear notch), similar to the arrangement shown in FIG. 77, but without bone pins through the femoral pin guide 514. The base 502 may then be moved medial or lateral to center the shaft 700 in the intercondylar notch.

Optionally, a bone pin or screw may be driven into the distal femur 102 through a hole (not shown) that is centered between the mounting holes 584 of the femoral pin guide 514. The screw holds the femoral riser 504 and base 502 centered in the medial-lateral width of the distal femur 102 and serves as a pivot post about which the femoral riser 504, base 502, and the femoral extension rod 506 can rotate in the medial-lateral direction so that the femoral extension rod may be positioned over the center 120 of the femoral head 118.

Referring to FIG. 73, the femoral riser 504 has been pinned to the distal femur, along with the attached base 502 and femoral extension rod 506. The base 502 is under the suprapatellar fat pad 116 against the anterior distal femoral cortex and centered in the medial-lateral width of the distal femur 102, the paddle 642 is against the medial distal femoral condyle, and the femoral extension rod passes over the center 120 of the femoral head 118 and between the uprights 836 of the target 820. The bone pins extend into the distal femur in the metaphyseal, or metaphyseal equivalent, region as opposed to the diaphyseal or epiphyseal regions.

Depending upon bone quality and the configuration of any frictional elements protruding from the bone contacting surface 518 of the base 502, the bone contacting surface 518 may actually be spaced apart slightly from the anterior distal femoral cortex, rather than directly against the cortex. For example, in hard bone, the spikes 538 alone may bear against the cortex. In this situation, the three spikes 538 may be said to define a theoretical bone contacting plane. The theoretical bone contacting plane functions the same as the actual bone contacting surface 518, and is interchangeable with the actual bone contacting surface 518 in this specification.

Figure 74:
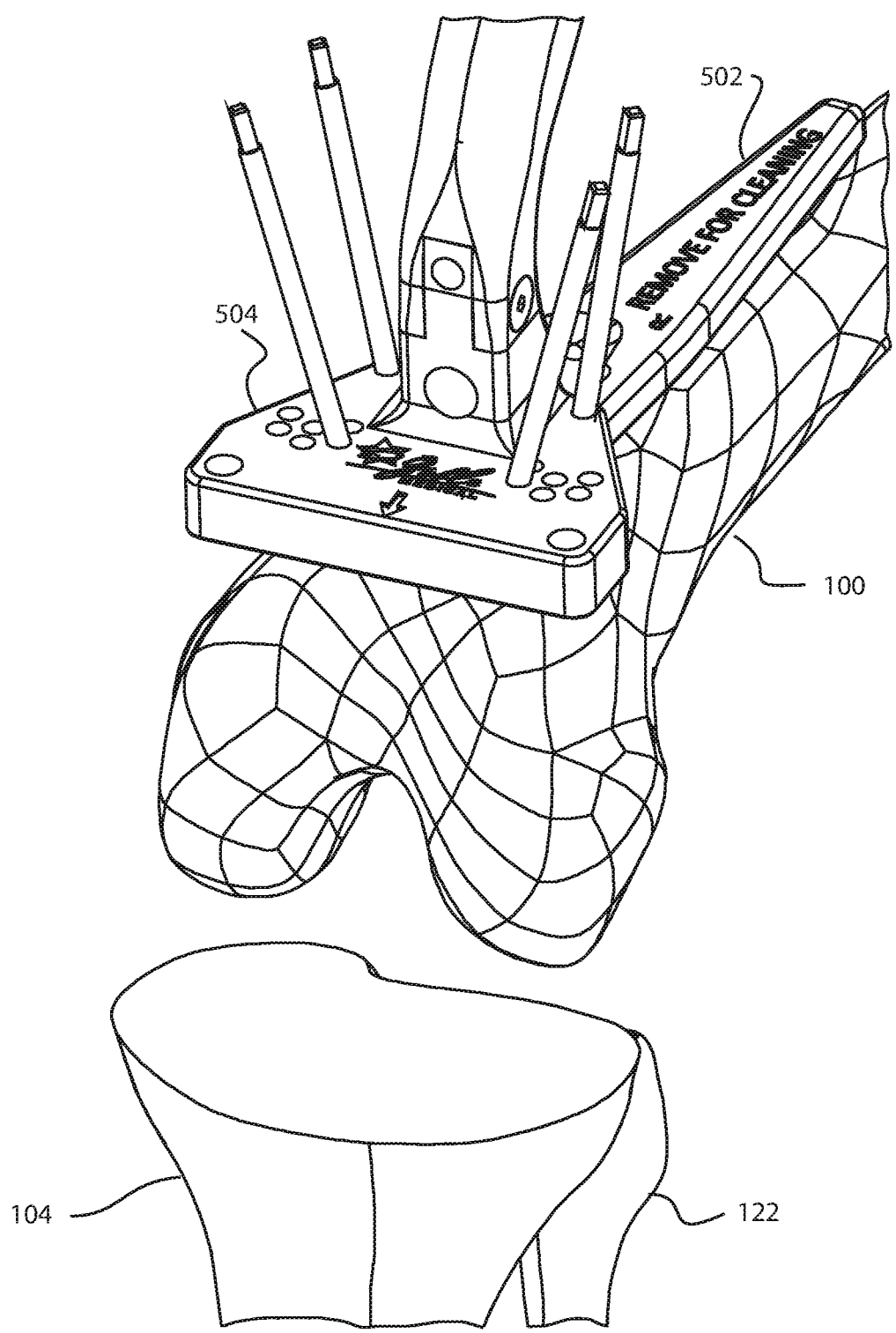
FIG. 74 is a perspective view of the femur, tibia, fibula, base, and femoral riser assembly of FIG. 73, after removing the distal femoral condyle block.

Referring to FIG. 74, the distal femoral condyle block 638 has been removed.

Referring to FIG. 75, the angle block assembly 652 has been coupled to the femoral riser 504. The clamp ring 672 has been loosened. The knee is shown in flexion in FIGS. 71-75, but may instead be in full extension during these steps.

Referring to FIG. 76, the Whiteside's angle gage assembly 696 has been coupled to the angle block assembly 652.

Referring to FIG. 77, the shaft 700 has been aligned with Whiteside's line and the clamp ring 672 has been tightened to save the orientation of the Whiteside's line in the angle block assembly 652. The knee is shown in flexion in FIGS. 76-77; this is preferable because it improves visibility of Whiteside's line.

Figure 78:
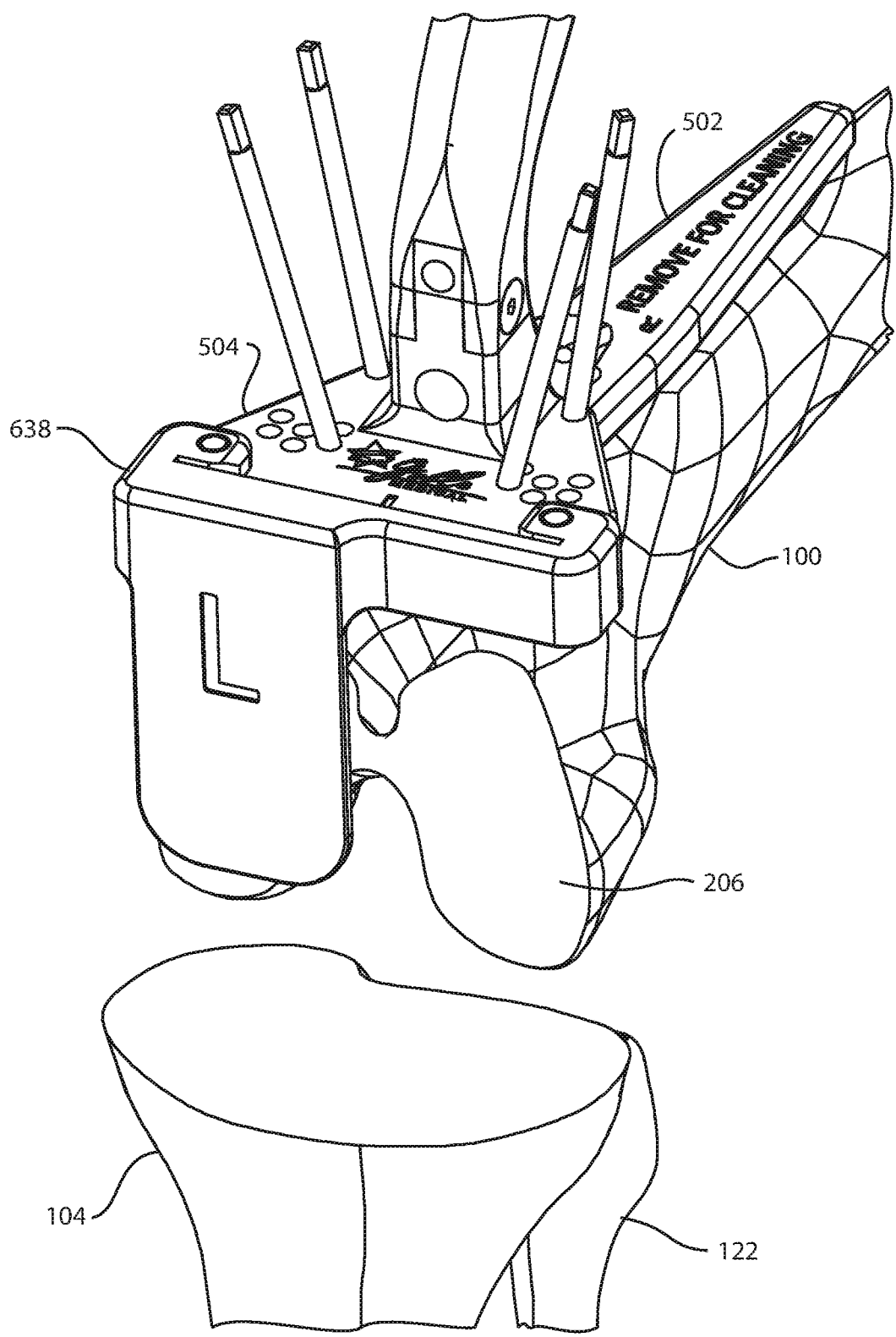
FIG. 78 is a perspective view of the femur, tibia, fibula, base, and femoral riser assembly of FIG. 77, after removing the Whiteside's line gage assembly and the angle block assembly, reattaching the distal femoral condyle block of FIG. 55A to the femoral riser assembly, and making a distal femoral resection guided by the distal femoral condyle block.

Referring to FIG. 78, the Whiteside's angle gage assembly 696 and the angle block assembly 652 have been removed from the femoral riser 504 and the distal femoral condyle block 638 has been replaced. A distal femoral resection 206 has been made, guided by the distal femoral condyle block 638. Preferably, the distal femoral resection 206 is made perpendicular to the mechanical axis 202 of the leg.

Figure 79:
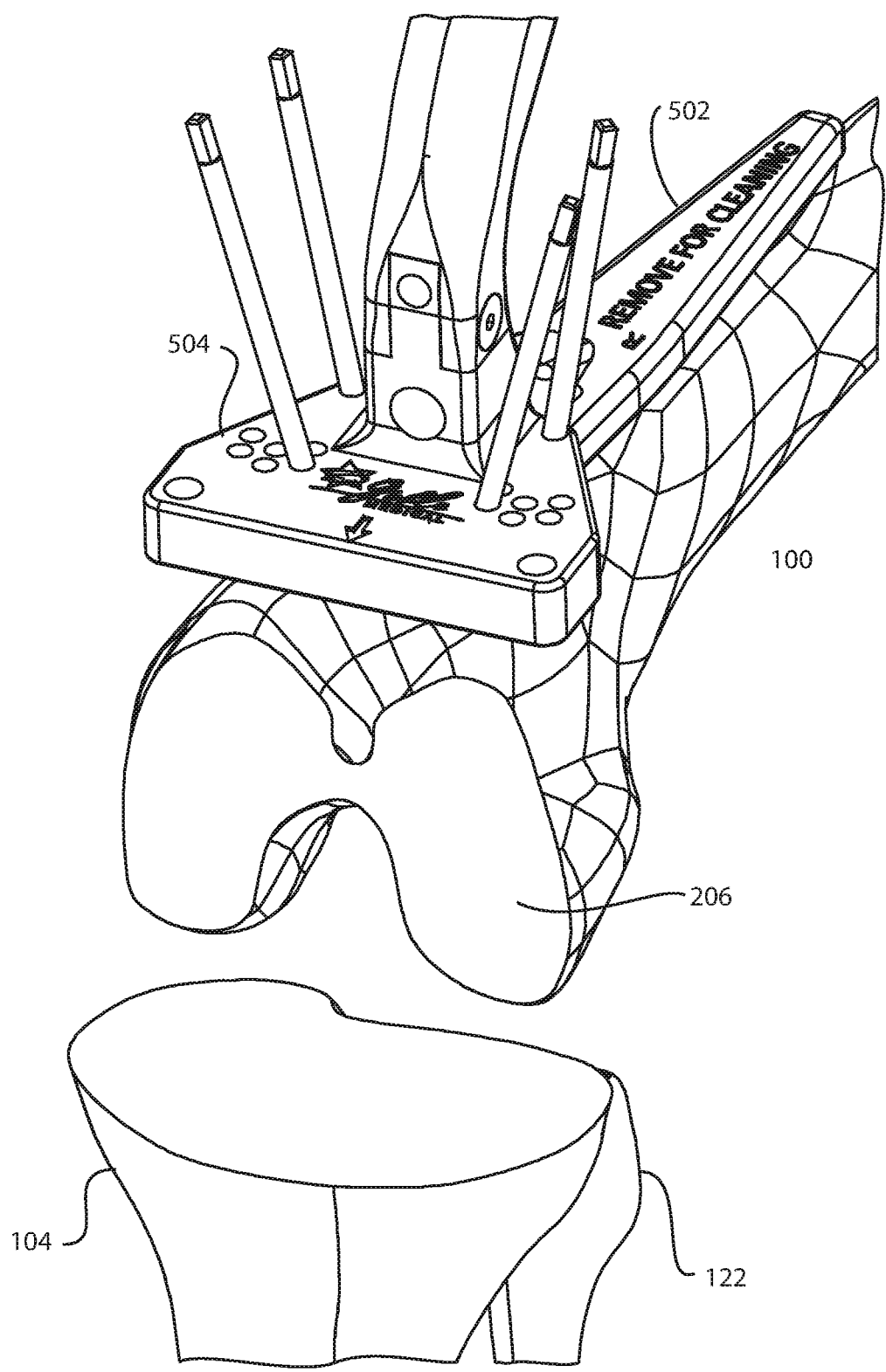
FIG. 79 is a perspective view of the femur, tibia, fibula, base, and femoral riser assembly of FIG. 78 after again removing the distal femoral condyle block.

Referring to FIG. 79, the distal femoral condyle block 638 has been removed again. The knee is shown in flexion in FIGS. 78-79, but may instead be in full extension during these steps.

Figure 80A:
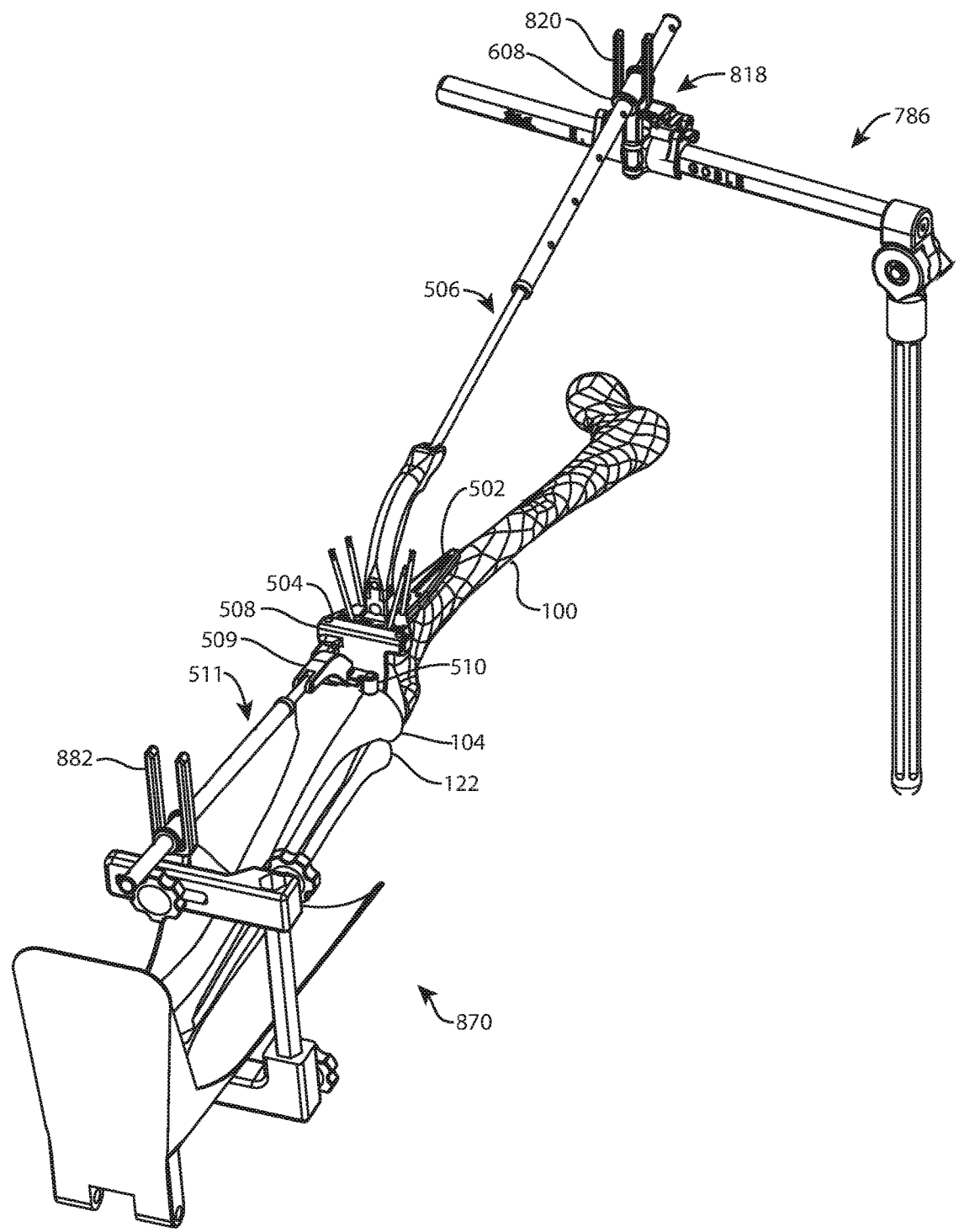
FIG. 80A is a perspective view of the femur, tibia, fibula, base, and femoral riser assembly of FIG. 79, after coupling the tibial connection block of FIG. 47A to the femoral riser assembly, coupling the tibial pin guide to the tibial connection block, placing the knee joint in full extension, and securing the foot in the foot holder assembly of FIG. 67A.
Figure 80B:
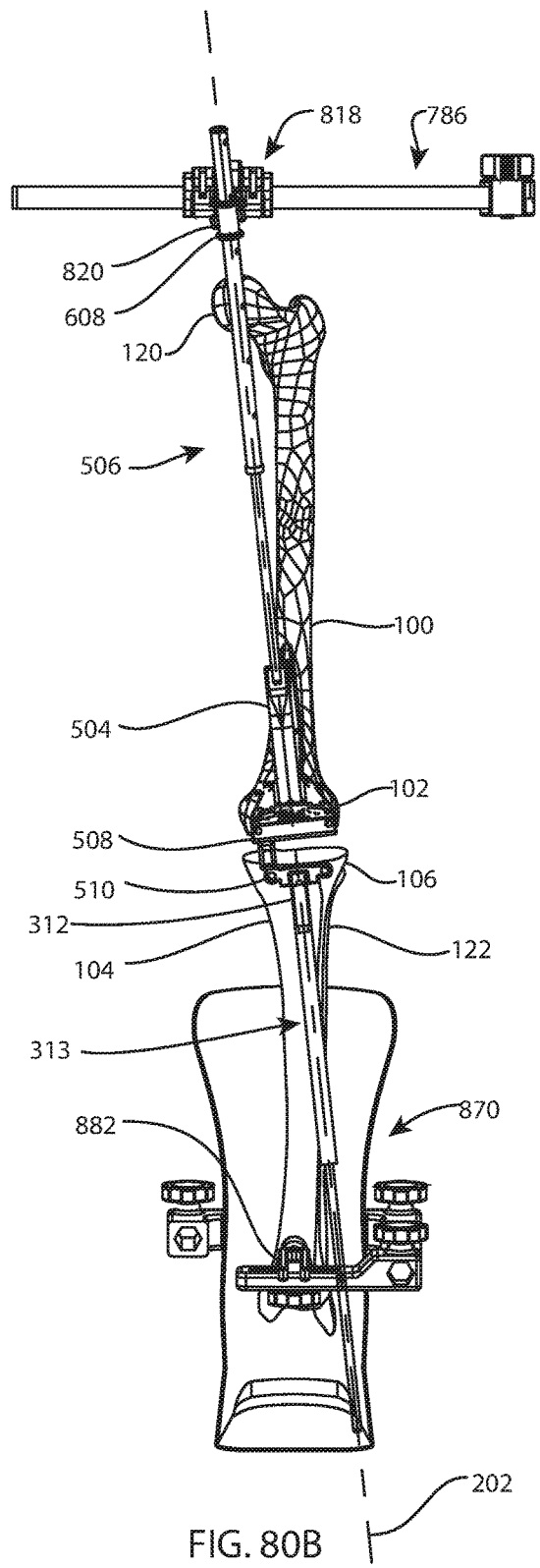
FIG. 80B is a top view of the femur, tibia, fibula, base, femoral riser assembly, tibial connection block, tibial pin guide, and foot holder assembly of FIG. 80A.

Referring to FIGS. 80A-B, the knee is in full extension, the foot has been secured within the foot holder assembly 870, the tibial connection block 508 has been coupled to the femoral riser 504, and the tibial pin guide 510 has been coupled to the tibial connection block 508 in preparation for the step of aligning the tibia to the mechanical axis 202 of the leg. In FIG. 80A, the tibial pin guide 510 is coupled to the tibial riser 509, which is coupled to the telescoping tibial extension rod 511. In FIG. 80B, the tibial pin guide 510 is shown in an alternate arrangement coupled to the tibial riser 312, which is coupled to the telescoping tibial extension rod 313. The proximal surface 774 of the tibial connection block 508 may be against the distal femoral resection 206. Other femoral resections 214, 216, 218, 220 may have been performed prior to this step. The foot holder assembly 870 is readily adaptable to hold the tibial target 882 over the anterior tibial crest or the tibial tuberosity, or any other location along the length of the tibia, ankle, or foot. Multiple tibial targets may be used, for example, one tibial target over the distal tibia/ankle and another tibial target over the tibial tuberosity.

As an alternative to a tibial target that is mounted to the foot holder assembly 870, a tibial target may be directly coupled to the tibia. For example, two bone pins may be placed in the proximal anterior tibia, one on either side of the tibial tuberosity, to serve as a proximal tibial target. The bone pins may be placed using a hand-held pin guide (not shown). The bone pins may be spaced apart so that the tibial riser 312 or 509 fits between the bone pins, is closely constrained by the bone pins to prevent medial-lateral translation, and is free to pivot in the medial-lateral direction so that the tibial extension rod 313 or 511 may be aimed at the distal tibial target.

Figure 80C:
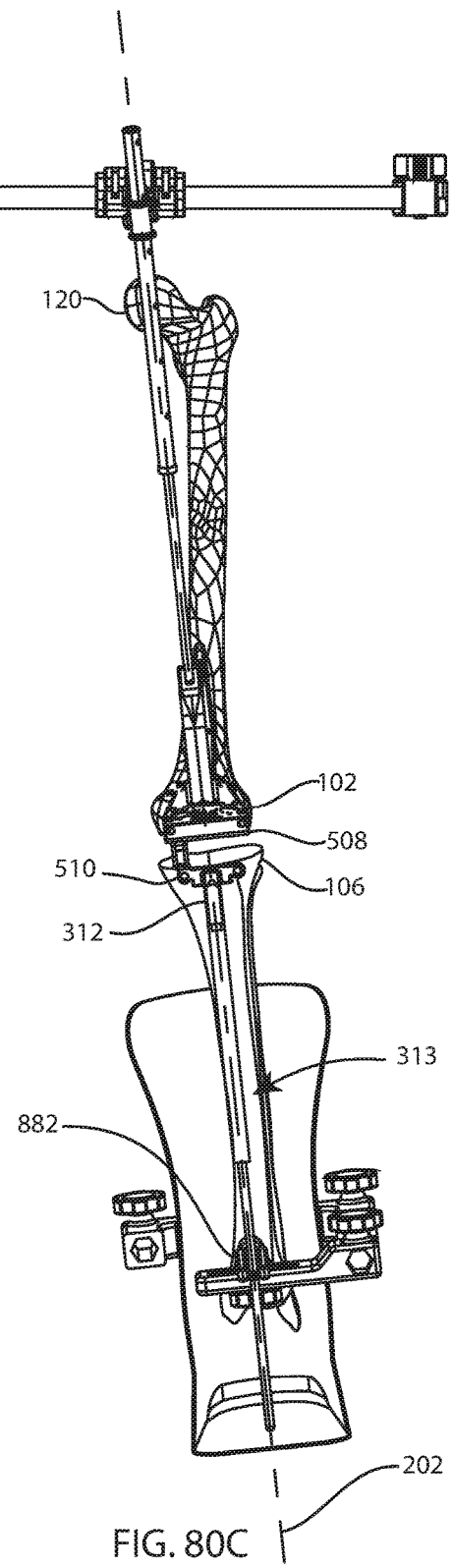
FIG. 80C is a top view of the femur, tibia, fibula, base, femoral riser assembly, tibial connection block, tibial pin guide, and foot holder assembly of FIG. 80B after aligning the tibia to the mechanical axis of the leg.

Referring to FIGS. 80B and 80C, one can appreciate that the femoral extension rod 506 and the tibial extension rod 313 or 511 are collinear in an anterior view.

Referring to FIG. 80C, the tibial pin guide 510 is shown coupled to the tibial riser 312, which is coupled to the telescoping tibial extension rod 313. Alternately, the tibial pin guide 510 may be coupled to the tibial riser 509, which is coupled to the telescoping tibial extension rod 511. The tibia 104 has been aligned to the mechanical axis 202 of the leg so that the entire leg is aligned: femoral head center 120, distal femur 102, proximal tibia 106, and, in this example, the ankle. Preferably, the knee joint is distracted to the extent permitted by the existing ligamentous structures of the knee while the tibia 104 is aligned to the mechanical axis 202. Now parallel bone pins may be inserted through the holes 782 of the tibial pin guide 510 into the tibia 104 in preparation for further surgical steps involving the tibia 104. The tibial pin guide 510 may be removed from the tibia, leaving the parallel bone pins behind. A subsequent instrument may be coupled to the tibia by sliding the instrument over the parallel bone pins. For example, the tibial cut guide 328 of FIGS. 34A-34B may be placed over the tibial bone pins, and a saw used through the tibial cut guide to make a proximal tibial resection 210.

Figure 81:
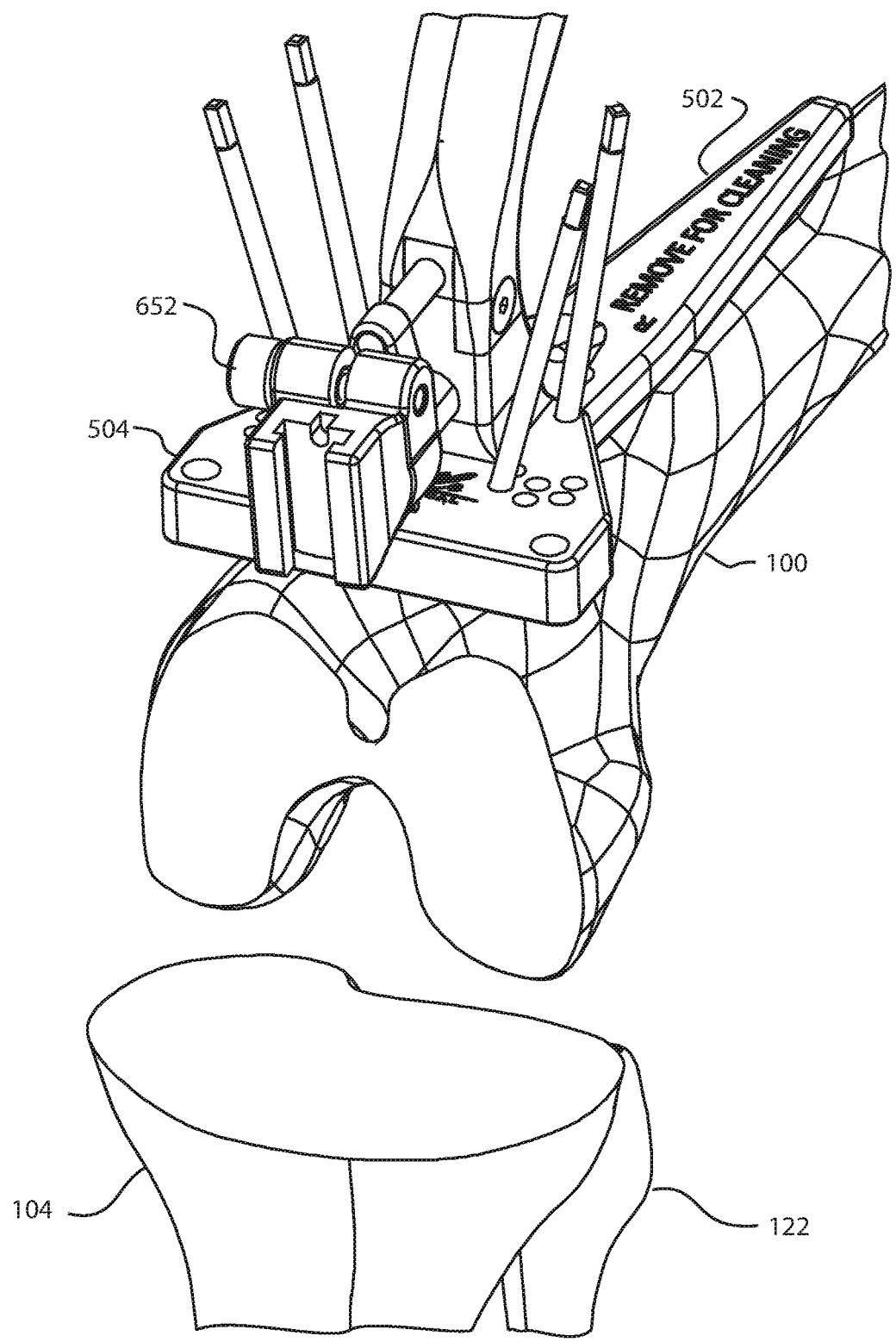
FIG. 81 is a perspective view of the femur, tibia, fibula, base, and femoral riser assembly of FIG. 80A, after removing the tibial connection block and tibial pin guide and reattaching the angle block assembly of FIG. 77 to the femoral riser assembly.

Referring to FIG. 81, the surgical procedure has turned to the femur 100. The angle block assembly 652 has been reattached to the femoral riser 504, and the clamp ring 672 remains tight, maintaining the alignment of Whiteside's line (FIG. 77) for the subsequent steps.

Figure 82:
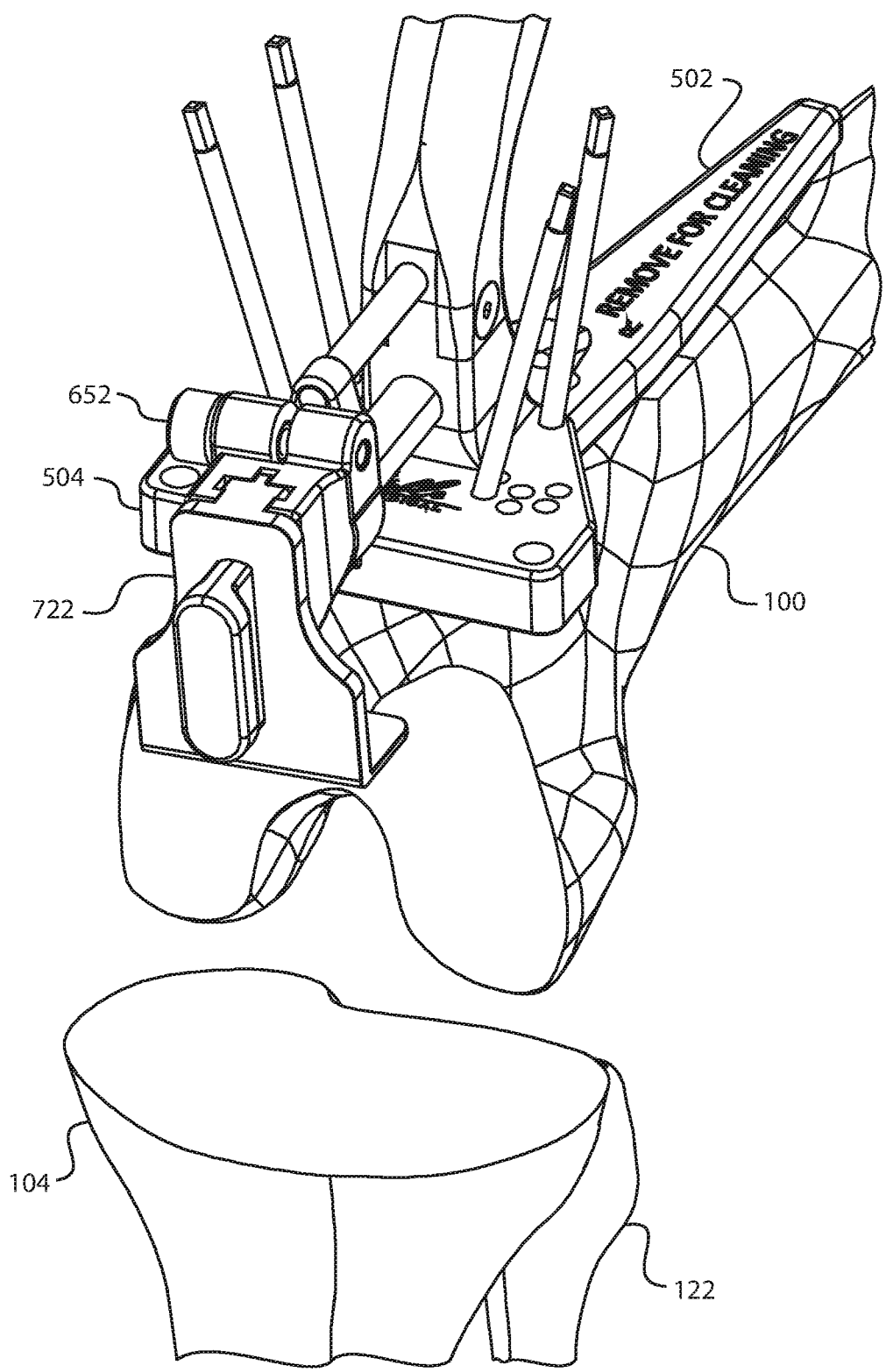
FIG. 82 is a perspective view of the femur, tibia, fibula, base, femoral riser assembly, and angle block assembly of FIG. 81, after coupling the cut guide mounting block assembly of FIG. 59A to the angle block assembly.

Referring to FIG. 82, the cut guide mounting block assembly 722 has been coupled to the angle block assembly 652.

Figure 83:
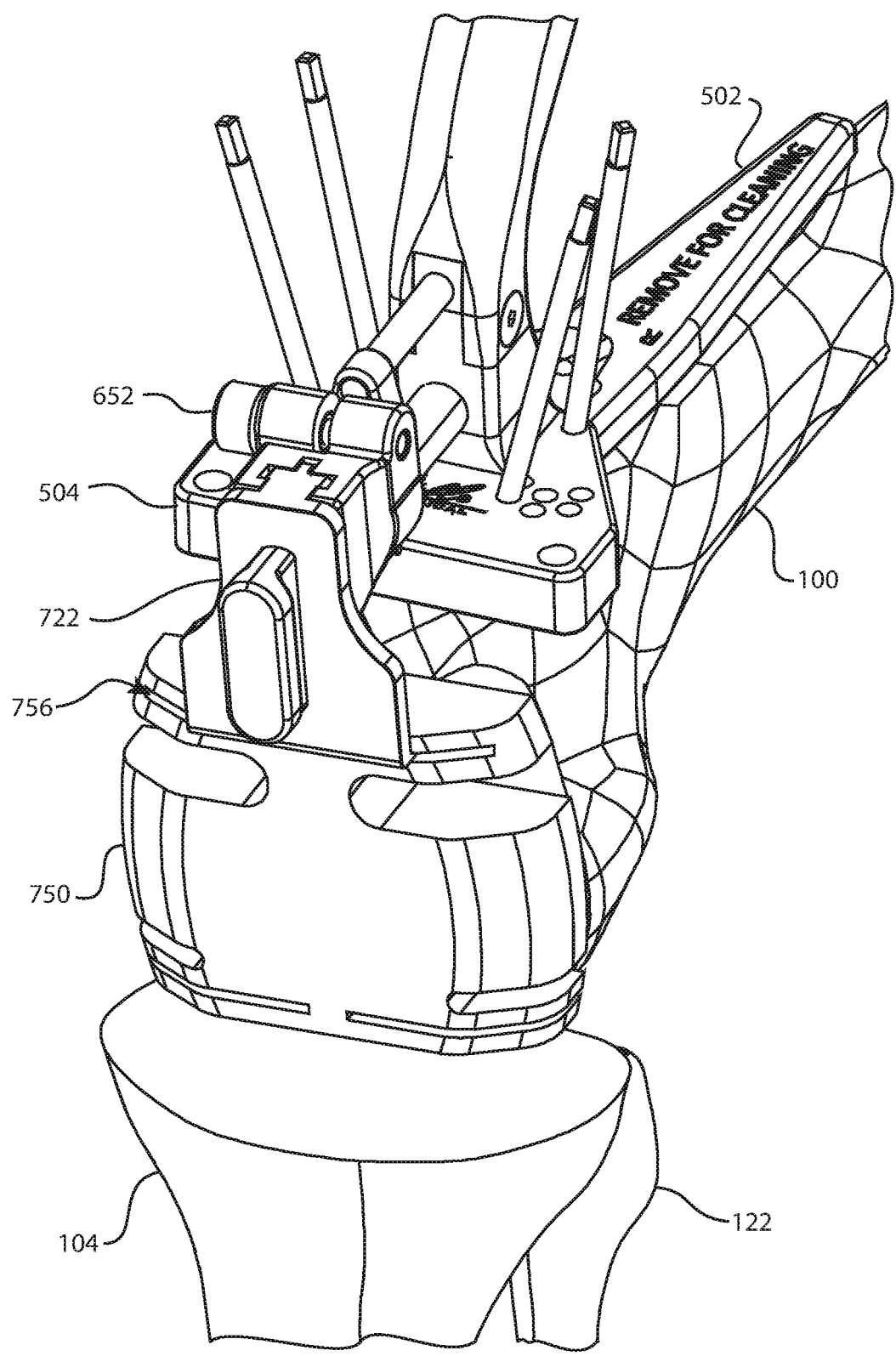
FIG. 83 is a perspective view of the femur, tibia, fibula, base, femoral riser assembly, angle block assembly, and cut guide mounting block assembly of FIG. 82, after coupling the four-in-one cut guide of FIG. 61A to the cut guide mounting block assembly.

Referring to FIG. 83, the four-in-one cut guide 750 has been coupled to the cut guide mounting block assembly 722.

Figure 84:
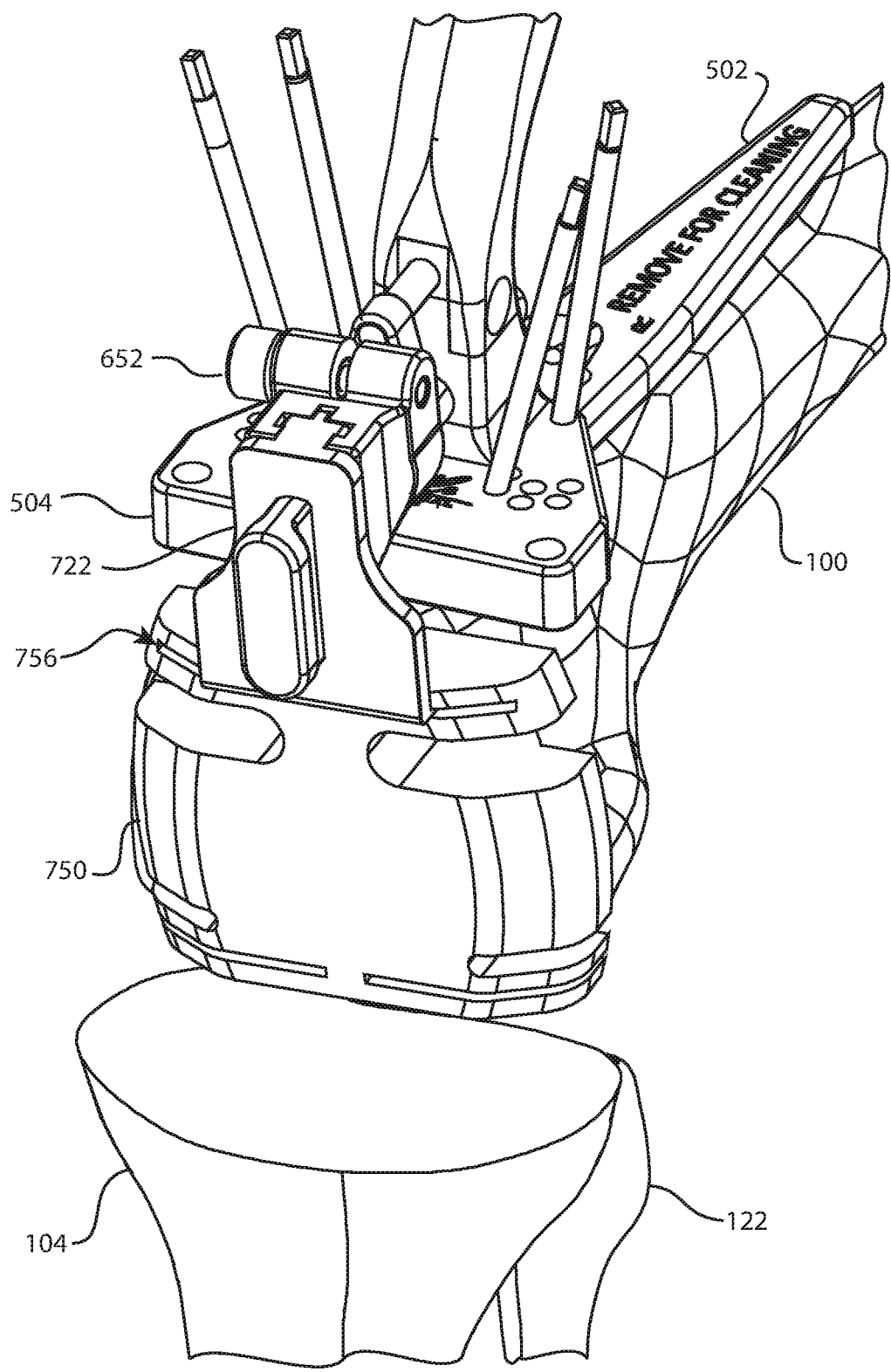
FIG. 84 is a perspective view of the femur, tibia, fibula, base, femoral riser assembly, angle block assembly, cut guide mounting block assembly, and four-in-one cut guide of FIG. 83 after aligning the four-in-one cut guide against the distal femoral resection.

Referring to FIG. 84, the four-in-one cut guide 750 has been aligned in the medial-lateral direction and positioned against the distal femoral resection 206. At this point, bone pins may be driven through medial and lateral holes (not shown) in the four-in-one cut guide 750 to secure the guide 750 to the distal femur.

Alternately, a drill bit or bone pin may be driven through a slot of the four-in-one cut guide 750 so that the drill extends in a proximal-distal direction, parallel to the bone contacting surface 518 of the base 502, at the level of the spikes 538. The drill bit or bone pin acts as a hanger for the four-in-one cut guide 750 while permitting rotational and side-to-side adjustment of the four-in-one cut guide. Rotational alignment may be provided by a block with an inclined plane, wherein the block is seated on the proximal tibial resection 210, wherein the four-in-one cut guide 750 rests on the inclined plane, wherein the plane is inclined in the medial-lateral direction and is higher under the lateral condyle. The plane may be 3 mm higher under the lateral condyle.

Figure 85:
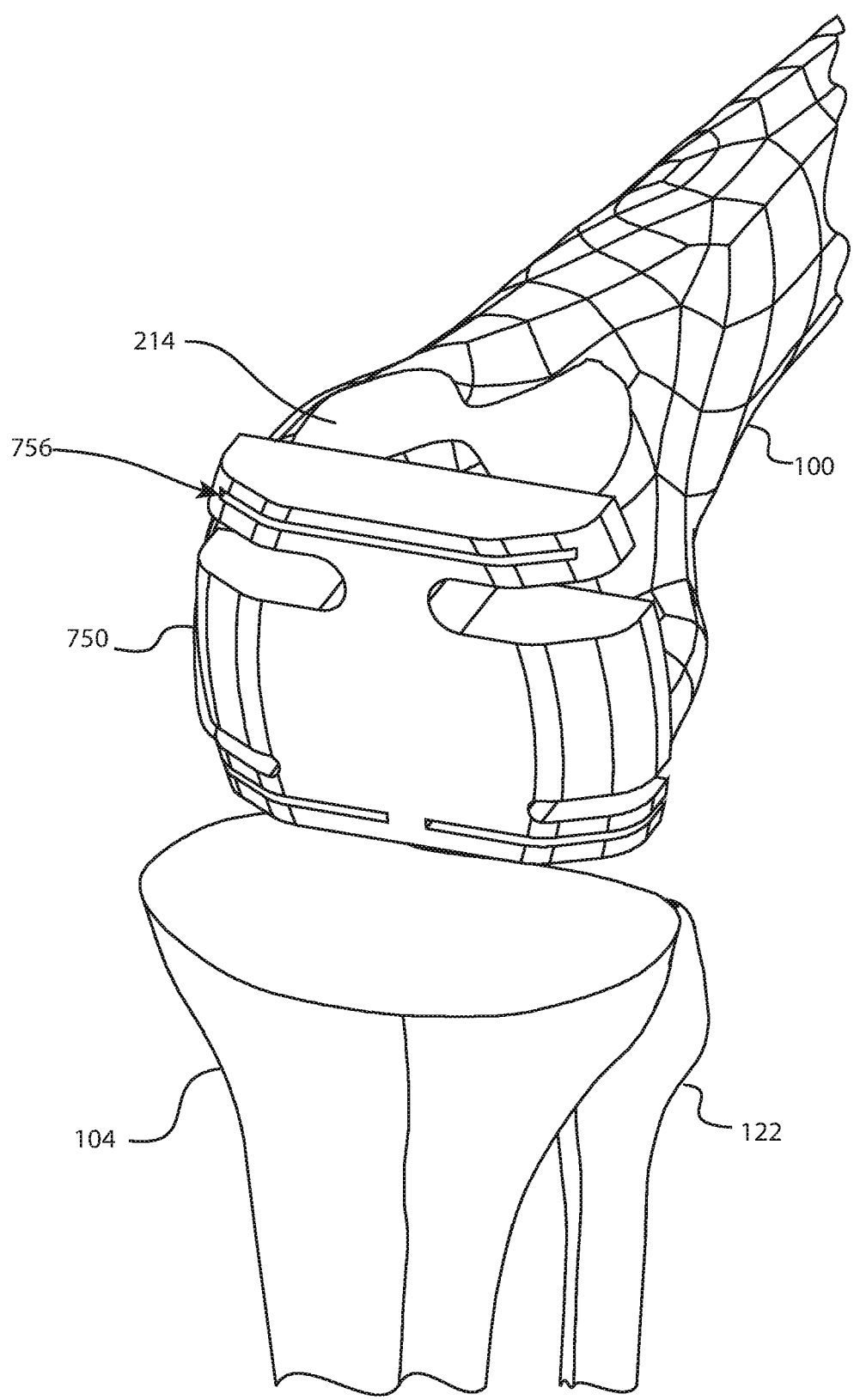
FIG. 85 is a perspective view of the femur, tibia, fibula, and four-in-one cut guide of FIG. 85, after fixing the four-in-one cut guide to the distal femoral resection, removing the base, femoral riser assembly, cut guide mounting block assembly, and angle block assembly, and making an anterior femoral resection guided by the four-in-one cut guide.

Referring to FIG. 85, the cut guide mounting block assembly 722, the angle block assembly 652, the femoral riser 504, and the base 502 have been removed from the femur 100, leaving only the four-in-one cut guide 750 secured to the femur. However, as explained above, preferably the femoral riser 504 and base 502 remain coupled to the femur 100 in this step. An anterior femoral resection 214 has been made through the slot 756. The anterior femoral resection 214 and the bone contacting surface 518 of the base 502 lie in a common plane.

After making the femoral resections 206, 214, 216, 218, and/or 220, the surgical procedure may turn to the tibia 104. The next step may be to align the tibia to the mechanical axis 202 of the leg as described for FIGS. 80A-80C. Alternately, the next steps may include coupling the tibial cut guide 328 (with the desired slope) to the proximal tibial bone pins previously placed using the tibial pin guide 510 and creating a final proximal tibial resection 210 through the tibial cut guide 328.

Figure 88:
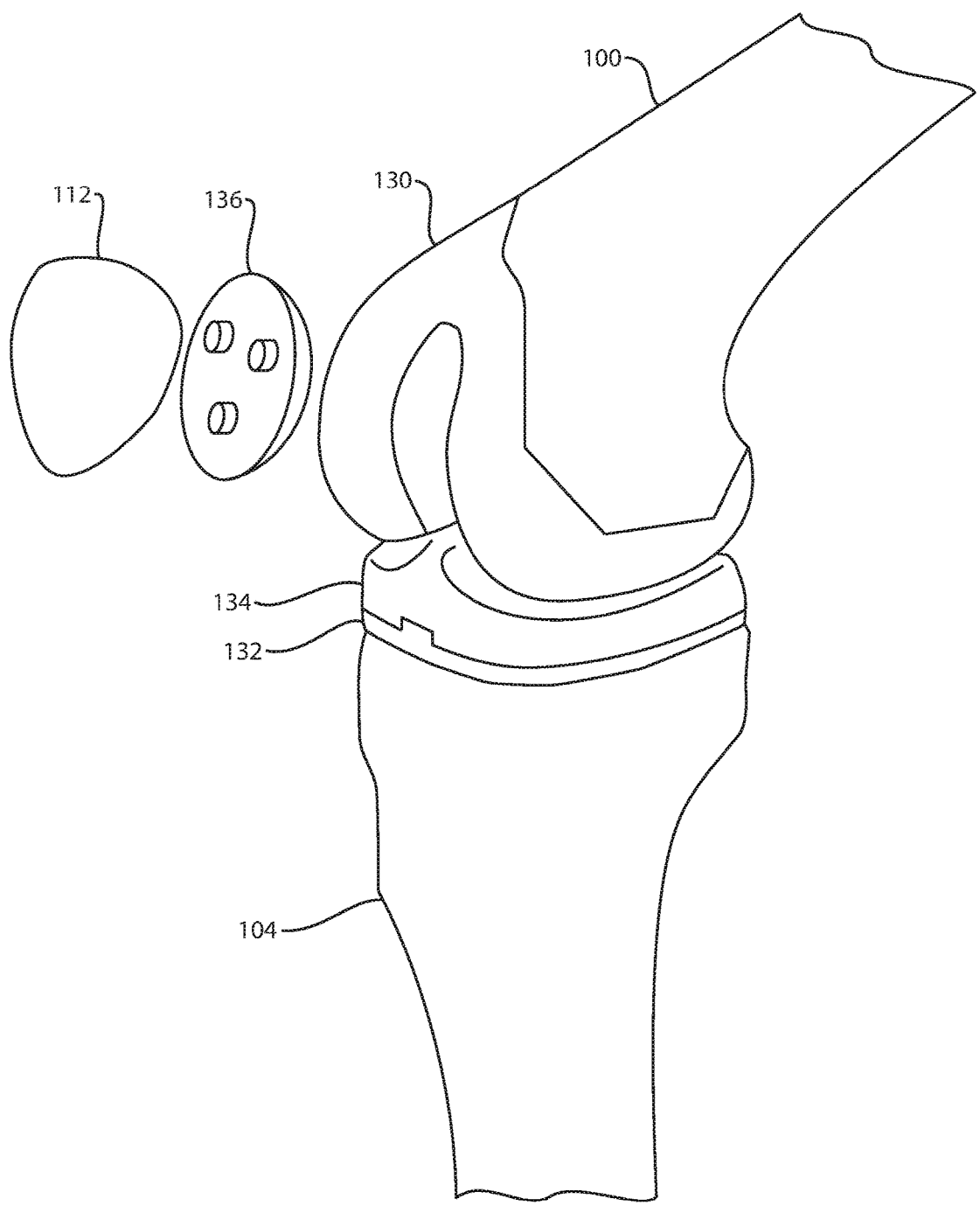
FIG. 88 is an isometric view of a knee joint with implanted femoral component, tibial component, articular insert, and patellar component, the patellar component shown exploded from the patella for clarity.

Referring to FIG. 88, after the femur 100, tibia 104, and optionally patella 112 are prepared, knee arthroplasty implants may be secured to the prepared bone surfaces. FIG. 88 is an isometric view of a knee joint with a femoral component 130, a tibial component 132, an articular insert 134, and a patellar component 136. The patellar component 136 is shown exploded from the patella for clarity, since the patellar component would otherwise be hidden by the patella in this view. Unicondylar or unicompartmental implants may be implanted instead of the total knee components shown.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the technology disclosed herein without departing from the spirit and scope of the invention as claimed.

The invention claimed is:

1. A method for cutting a femur during knee joint replacement surgery, the method comprising:
   placing an instrument base on a distal anterior surface of the femur with a posterior surface of the instrument base in contact with the distal anterior surface of the femur before making any femoral cuts, wherein the posterior surface of the instrument base has a plurality of protruding frictional elements, wherein the instrument base comprises a length and a width, wherein the length is greater than the width, and when the instrument base is mounted on the distal anterior surface of the femur, the length extends along a superior-inferior direction relative to the femur, wherein a handle protrudes anteriorly and superiorly from the instrument base, and wherein a femoral extension rod protrudes superiorly from the handle;
   securing the instrument base to the distal anterior surface of the femur with fasteners extending through the instrument base into the femur or by engaging the frictional elements in the femur while, in an anterior view of the femur, a superior portion of the femoral extension rod is centered over a center of a head of the femur and an inferior portion of the femoral extension rod is centered over a distal medial-lateral width of the femur so that the handle and the femoral extension rod are aligned with a femoral mechanical axis;
   coupling anterior and posterior femoral cut guides to the handle with an interconnection that aligns a cutter guide of the anterior femoral cut guide coplanar with the posterior surface of the instrument base and constrains the anterior and posterior femoral cut guides to slide straight along the femoral mechanical axis in the anterior view of the femur;
   sliding the anterior and posterior femoral cut guides along the femoral mechanical axis to abut an unresected distal aspect of at least one distal condyle of the femur; and
   guiding a cutter along the cutter guide of the anterior femoral cut guide to produce an anterior femoral cut coplanar with the posterior surface of the instrument base and guiding the cutter along a cutter guide of the posterior femoral cut guide to produce a posterior femoral cut offset posteriorly from the anterior femoral cut.

2. The method of claim 1, comprising adjusting the anterior and posterior femoral cut guides to vary the distance between the anterior and posterior femoral cuts to match a femoral implant interior anterior/posterior dimension.

3. The method of claim 2, comprising adjusting the anterior and posterior femoral cut guides on rails.

4. The method of claim 1, comprising fixing the anterior and posterior femoral cut guides to the femur.

5. The method of claim 1, comprising placing the knee in 90 degrees of flexion prior to making the anterior and posterior femoral cuts.

6. The method of claim 1, comprising:
   dismounting the anterior and posterior femoral cut guides from the instrument base while the instrument base is secured to the distal anterior surface of the femur;
   coupling a femoral trial component to the anterior and posterior femoral cuts while the instrument base is secured to the distal anterior surface of the femur;
   moving a tibia of the knee joint through a flexion-extension range of motion relative to the femur of the knee joint while the instrument base is secured to the distal anterior surface of the femur; and
   adjusting the anterior and posterior femoral cuts.

7. The method of claim 1, comprising centering the instrument base in a distal medial-lateral width of the femur.

8. A method for cutting a femur during knee joint replacement surgery, the method comprising:
- placing an instrument base on a distal anterior surface of the femur with a posterior surface of the instrument base in contact with the distal anterior surface of the femur before making any femoral cuts, wherein the posterior surface of the instrument base has a plurality of protruding frictional elements, wherein the instrument base comprises a length and a width, wherein the length is greater than the width, and when the instrument base is mounted on the distal anterior surface of the femur, the length extends along a superior-inferior direction relative to the femur, wherein a handle protrudes anteriorly and superiorly from the instrument base, and wherein a femoral extension rod protrudes superiorly from the handle;
- securing the instrument base to the distal anterior surface of the femur with fasteners extending through the instrument base into the femur or by engaging the frictional elements in the femur while, in an anterior view of the femur, a superior portion of the femoral extension rod is centered over a center of a head of the femur and an inferior portion of the femoral extension rod is centered over a distal medial-lateral width of the femur so that the handle and the femoral extension rod are aligned with a femoral mechanical axis;
- mounting anterior and posterior femoral cut guides to the instrument base and to abut an unresected distal aspect of at least one distal condyle, the anterior femoral cut guide having a cutter guide aligned coplanar with the posterior surface of the instrument base;
- guiding a cutter along the cutter guide of the anterior femoral cut guide to produce an anterior femoral cut coplanar with the posterior surface of the instrument base and guiding the cutter along a cutter guide of the posterior femoral cut guide to produce a posterior femoral cut offset posteriorly from the anterior femoral cut while the instrument base is secured to the distal anterior surface of the femur;
- dismounting the anterior and posterior femoral cut guides from the instrument base while the instrument base is secured to the distal anterior surface of the femur;
- coupling a femoral trial component to the anterior and posterior femoral cuts while the instrument base is secured to the distal anterior surface of the femur; and
- moving a tibia of the knee joint through a flexion-extension range of motion relative to the femur of the knee joint while the instrument base is secured to the distal anterior surface of the femur and the femoral trial component is coupled to the anterior and posterior femoral cuts.

9. The method of claim 8, comprising adjusting the anterior and posterior femoral cut guides to vary the distance between the anterior and posterior femoral cuts to match a femoral implant interior anterior/posterior dimension.

10. The method of claim 9, comprising adjusting the anterior and posterior femoral cut guides on rails.

11. The method of claim 8, comprising fixing the anterior and posterior femoral cut guides to the femur.

12. The method of claim 8, comprising placing the knee joint in 90 degrees of flexion prior to making the anterior and posterior femoral cuts.

13. The method of claim 8, comprising centering the instrument base in a distal medial-lateral width of the femur.

* * * * *